(12) United States Patent
Weber

(10) Patent No.: US 8,968,302 B2
(45) Date of Patent: Mar. 3, 2015

(54) METHODS, APPARATUS, AND SYSTEMS FOR TISSUE DISSECTION AND MODIFICATION

(71) Applicant: Paul Joseph Weber, Queenstown (NZ)

(72) Inventor: Paul Joseph Weber, Queenstown (NZ)

(73) Assignee: TDM SurgiTech, Inc., Palm Harbor, FL (US)

( * ) Notice: Subject to any disclaimer, the term of this patent is extended or adjusted under 35 U.S.C. 154(b) by 275 days.

(21) Appl. No.: 13/760,042

(22) Filed: Feb. 5, 2013

(65) Prior Publication Data
US 2014/0188111 A1 Jul. 3, 2014

Related U.S. Application Data

(60) Provisional application No. 61/748,037, filed on Dec. 31, 2012, provisional application No. 61/751,239, filed on Jan. 10, 2013.

(51) Int. Cl.
*A61B 18/18* (2006.01)
*A61B 18/08* (2006.01)
(Continued)

(52) U.S. Cl.
CPC ........... *A61B 18/082* (2013.01); *A61B 18/1482* (2013.01); *A61B 18/149* (2013.01); *A61B 19/2203* (2013.01); *A61B 18/1402* (2013.01); *A61B 18/148* (2013.01); *A61B 2017/00106* (2013.01); *A61B 2018/00023* (2013.01); *A61B 2018/00791* (2013.01); *A61B 2018/00875* (2013.01); *A61B 2019/448* (2013.01); *A61N 2007/0047* (2013.01); *A61B 2018/00863* (2013.01); *A61N 7/00* (2013.01); *A61B 18/1815* (2013.01); *A61B 18/201* (2013.01); *A61B 19/5244* (2013.01); *A61B 2017/00221* (2013.01); *A61B 2018/00303* (2013.01); *A61B 2018/00589* (2013.01); *A61B 2018/00601* (2013.01); *A61B 2018/00619* (2013.01);
(Continued)

(58) Field of Classification Search
USPC ........................................................ 606/45
See application file for complete search history.

(56) References Cited

U.S. PATENT DOCUMENTS

| 4,221,997 A | 9/1980 | Flemming |
| 4,259,876 A | 4/1981 | Belyanin et al. |

(Continued)

OTHER PUBLICATIONS

Miniaturized Ultrasound Arrays for Interstitial Ablation and Imaging (Makin, Mast, Faidi, et al.; Ultrasound Med Biol 2005;31(11)1539-50.).

(Continued)

*Primary Examiner* — Robert N Wieland

(57) ABSTRACT

Methods, apparatus and systems for tissue dissection and modification are disclosed herein. A method for tissue dissection and modification may comprise inserting a tissue dissecting and modifying wand (TDM) through an incision in a patient's body. The TDM may comprise a tip having a plurality of protrusions with lysing segments positioned between the protrusions to dissect and/or modify tissue. The TDM may also comprise an energy window positioned on top of the TDM that is configured to deliver energy to modify tissues. After separating tissue using the lysing segment(s) to define a target region, the energy window may be activated and moved around within the target region to modify tissues. In some implementations, the energy window may be activated prior to and/or during dissection of the tissue such that the tissue is separated while tissue is modified within the target region.

53 Claims, 16 Drawing Sheets

(51) Int. Cl.
A61B 18/14 (2006.01)
A61B 19/00 (2006.01)
A61B 17/00 (2006.01)
A61B 18/00 (2006.01)
A61N 7/00 (2006.01)
A61B 18/20 (2006.01)
A61B 18/22 (2006.01)

(52) U.S. Cl.
CPC ............... A61B 2018/00642 (2013.01); A61B 2018/0066 (2013.01); A61B 2018/00666 (2013.01); A61B 2018/00708 (2013.01); A61B 2018/00714 (2013.01); A61B 2018/0072 (2013.01); A61B 2018/00761 (2013.01); A61B 2018/00797 (2013.01); A61B 2018/00815 (2013.01); A61B 2018/00821 (2013.01); A61B 2018/00898 (2013.01); A61B 2018/00982 (2013.01); A61B 2018/1807 (2013.01); A61B 2018/2211 (2013.01); A61B 2019/5445 (2013.01); A61B 2019/5475 (2013.01); A61B 2218/002 (2013.01); A61B 2218/007 (2013.01)
USPC .......................................................... 606/45

(56) References Cited

U.S. PATENT DOCUMENTS

| | | |
|---|---|---|
| 4,462,748 A | 7/1984 | Inaba et al. |
| 4,494,417 A | 1/1985 | Larson et al. |
| 4,582,057 A | 4/1986 | Auth et al. |
| 4,631,689 A | 12/1986 | Arimura et al. |
| 4,806,066 A | 2/1989 | Rhodes et al. |
| 4,862,890 A | 9/1989 | Stasz |
| 5,244,462 A | 9/1993 | Delahuerga |
| 5,395,363 A | 3/1995 | Billings et al. |
| 5,647,867 A | 7/1997 | Neuberger et al. |
| 5,693,043 A | 12/1997 | Kittrell et al. |
| 5,695,510 A | 12/1997 | Hood |
| 5,755,753 A | 5/1998 | Knowlton |
| 5,776,092 A | 7/1998 | Farin et al. |
| 5,791,231 A | 8/1998 | Cohn et al. |
| 5,827,267 A | 10/1998 | Savage et al. |
| 5,860,976 A | 1/1999 | Billings et al. |
| 5,871,524 A | 2/1999 | Knowlton |
| 5,873,855 A | 2/1999 | Eggers |
| 5,919,219 A | 7/1999 | Knowlton |
| 5,935,143 A | 8/1999 | Hood |
| 5,948,011 A | 9/1999 | Knowlton |
| 5,951,550 A | 9/1999 | Shirley et al. |
| 5,984,915 A | 11/1999 | Loeb et al. |
| 6,033,398 A | 3/2000 | Farley et al. |
| 6,135,999 A | 10/2000 | Fanton et al. |
| 6,176,854 B1 | 1/2001 | Cone |
| 6,203,540 B1 | 3/2001 | Weber |
| 6,241,753 B1 | 6/2001 | Knowlton |
| 6,277,116 B1 | 8/2001 | Utley et al. |
| 6,311,090 B1 | 10/2001 | Knowlton |
| 6,346,105 B1 | 2/2002 | Tu et al. |
| 6,391,023 B1 | 5/2002 | Weber et al. |
| 6,432,101 B1 | 8/2002 | Weber et al. |
| 6,440,121 B1 | 8/2002 | Weber et al. |
| 6,974,450 B2 | 12/2005 | Weber et al. |
| 7,199,545 B2 | 4/2007 | Oleynikov et al. |
| 7,316,681 B2 | 1/2008 | Madhani et al. |
| 7,494,488 B2 * | 2/2009 | Weber ............................ 606/2 |
| 7,959,633 B2 | 6/2011 | Sartor et al. |
| 8,182,418 B2 | 5/2012 | Durant et al. |
| 8,224,485 B2 | 7/2012 | Unsworth |
| 2007/0225550 A1 | 9/2007 | Gattani et al. |
| 2009/0281419 A1 | 11/2009 | Troesken et al. |

OTHER PUBLICATIONS

Design and Preliminary Results of an Ultrasound Applicator for Interstitial Thermal Coagulation (Lafon, Chapelon, Prat, et al.; Ultrasound Med Biol 1998;24(1):113-22.).

Optimizing the Shape of Ultrasound Transducers for Interstitial Thermal Ablation (Lafon, Theillere, et al.; Med Phys 2002;29(3):290-7.).

Rapid Skin Permeablization by the Simultaneous Application of Dual Frequency, High-Intensity Ultrasound (Schoelhammer, Polat, Mendenhall, Langer, et al; Journal of Controlled Release, 2012, 163(2):154-160.).

Interstitial Devices for Minimally Invasive Thermal Ablation by High Intensity Ultrasound (Lafon, Melodelima, Salomir, Chaelon; Int J. Hyperther 2007; 23(2):153-63.).

Theoretical Comparison of Two Interstitial Ultrasound Applicators Designed to Induce Cylindrical Zones of Tissue Ablation (Lafon, Chavrier, Prat, et al.; Med Biol Eng Comput 1999;37(3):298-303.).

Feasibility of Linear Arrays for Interstitial Ultrasound Thermal Therapy (Chopra, Bronskill, Foster; Med Phys 2000;27(6):1281-6.).

Development of an Interstitial Ultrasound Applicator for Endoscopic Procedures: Animal Experimentation (Lafon, Theillere, Prat, et al.; Ultrasound Med Biol 2000;26(4):669-75.).

Multisectored Interstitial Ultrasound Applicators for Dynamic Angular Control of Thermal Therapy (Kinsey, Diederich, Tyreus, et al.; Med Phys 2006;33(5)1352-63).

Evaluation of Multielement catheter-cooled interstitial ultrasound applicators for high-temperature thermal therapy (Nau, Diederich, Burdette; Med Phys 2001;28(7)1525-34.).

Feasibility of Ultrasound Hyperthermia with Waveguide Interstitial Applicator (Jarosz; IEEE Trans Biomed Eng 1996;43(11):1106-15.).

Transurethral Ultrasound Array for Prostate Thermal Therapy: Initial Studies (Diederich, Burdette; IEEE Trans Ultrason Ferroelectr Freq Control 1996;43(6):1011-22.).

* cited by examiner

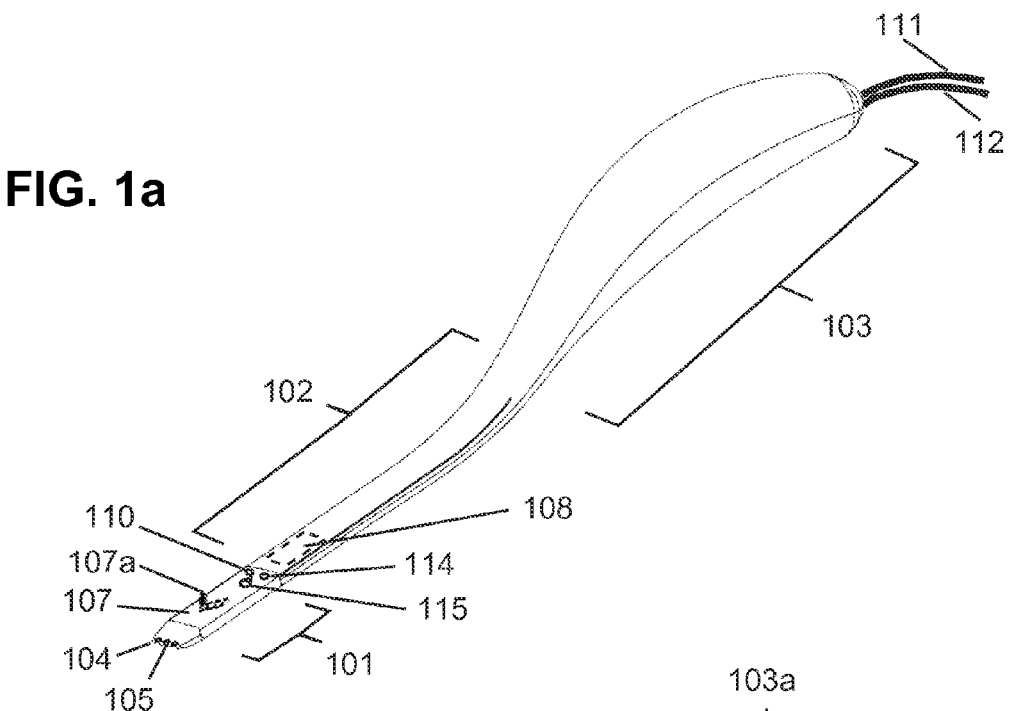
FIG. 1a
FIG. 1b
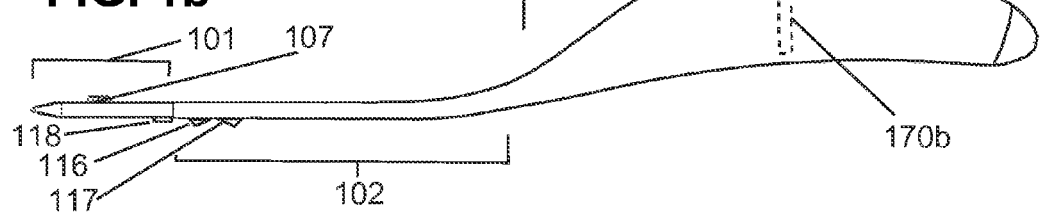
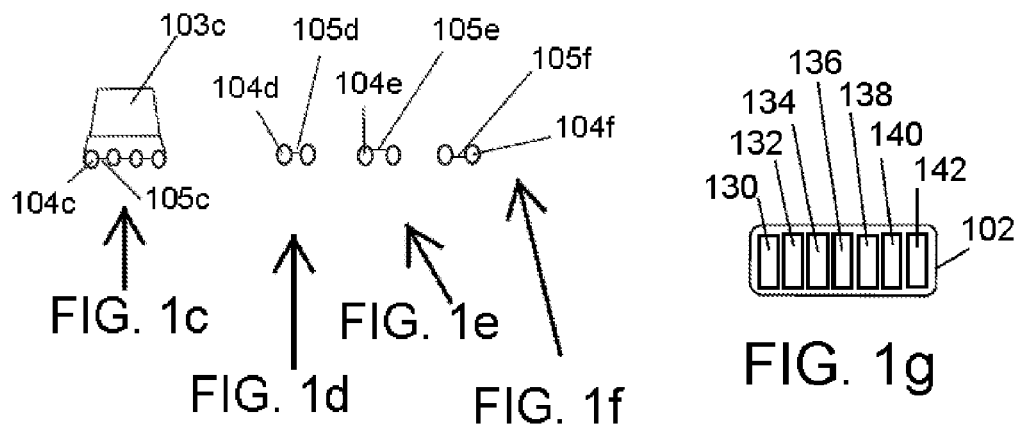
FIG. 1c  FIG. 1d  FIG. 1e  FIG. 1f  FIG. 1g

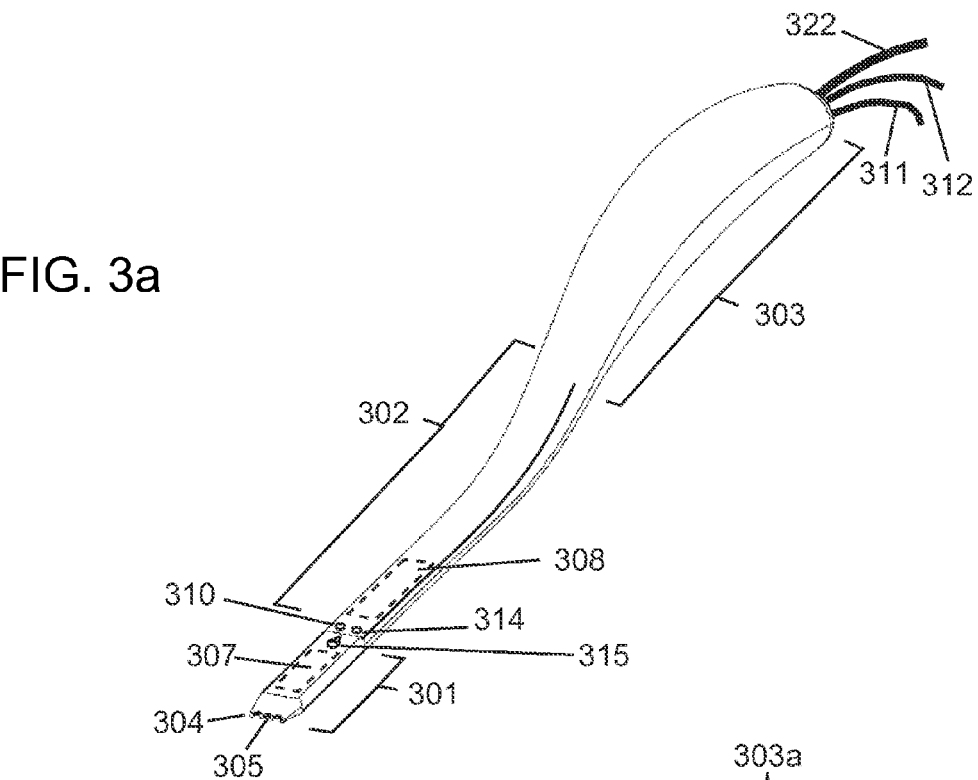
FIG. 3a
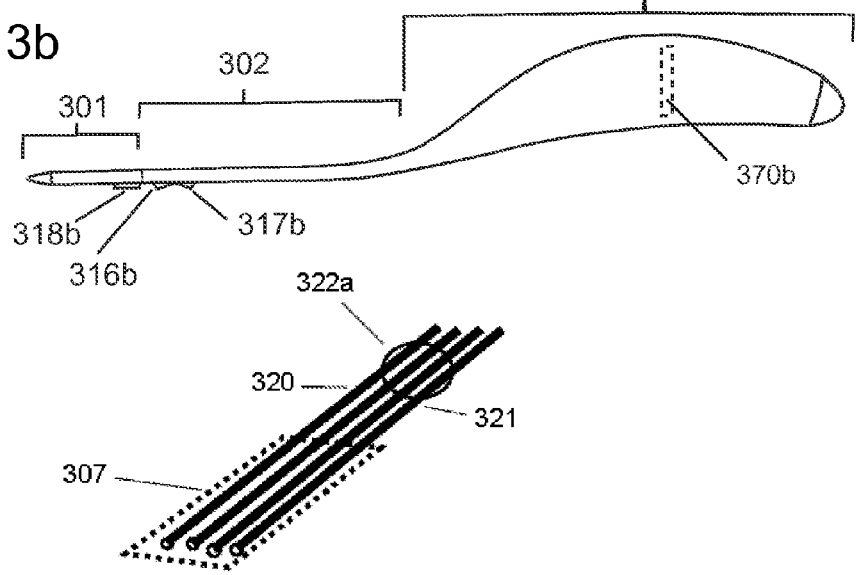
FIG. 3b
FIG. 3c

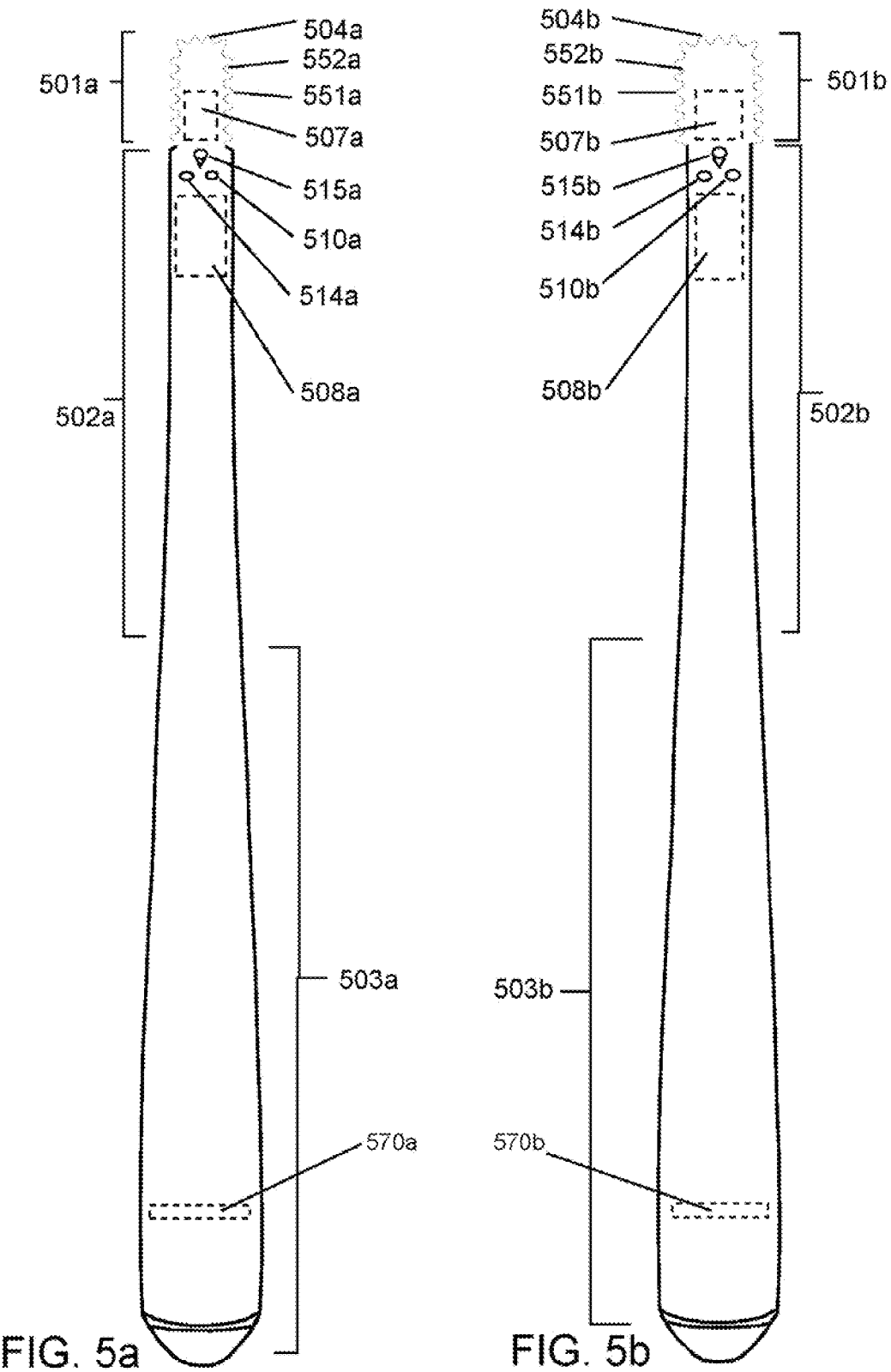

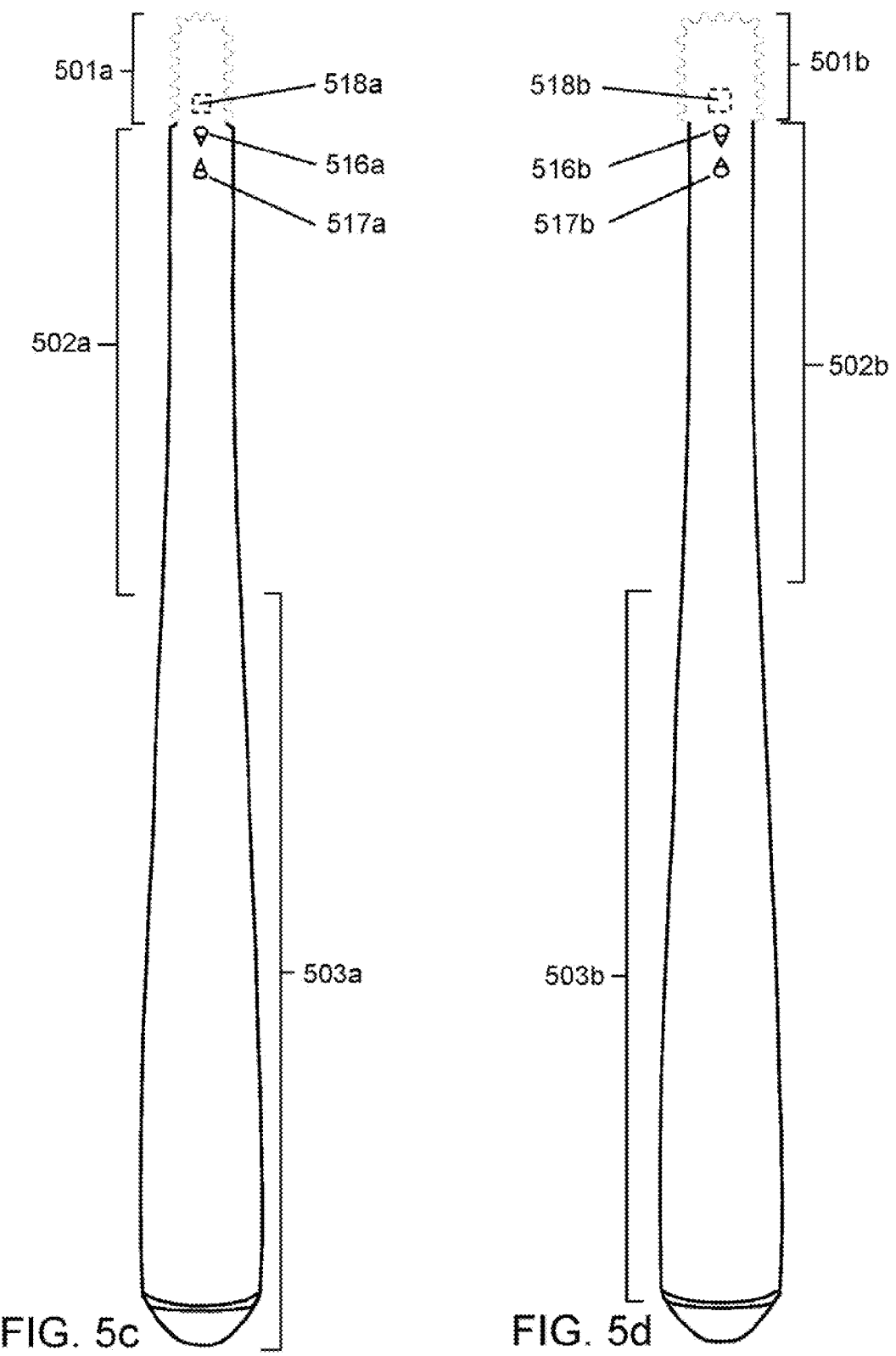

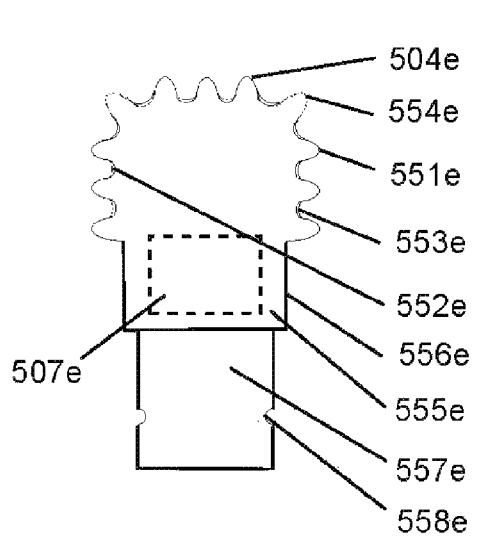
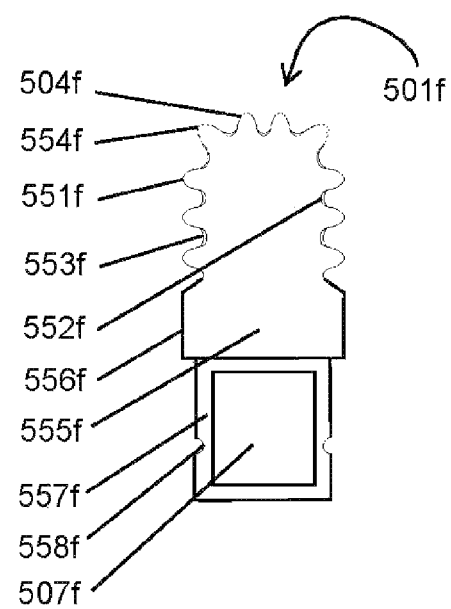
FIG. 5e
FIG. 5f
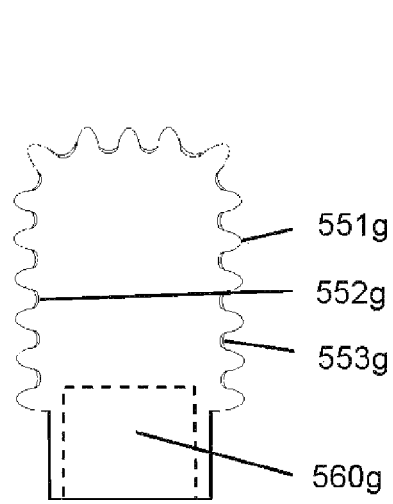
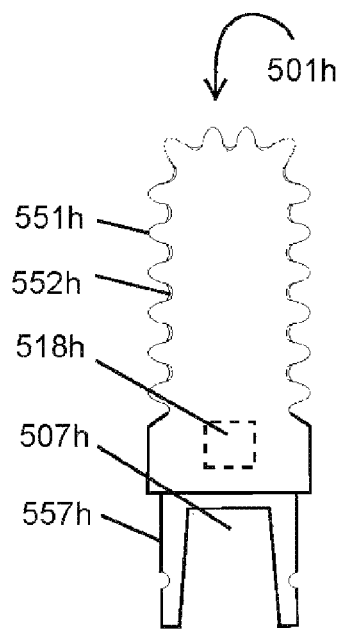
FIG. 5g
FIG. 5h

METHODS, APPARATUS, AND SYSTEMS FOR TISSUE DISSECTION AND MODIFICATION

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1a is a perspective view of an embodiment of a tissue dissector and modifier with an energy window on the upper side of the device.

FIG. 1b is a side elevation view of the embodiment previously depicted in FIG. 1a.

FIG. 1c is a front elevation view of the embodiment previously depicted in FIG. 1a.

FIG. 1d is a front elevation view illustrating the protrusions and lysing segment of an alternative embodiment of a tissue dissector and modifier wherein the lysing segment connecting the two protrusions is centered substantially midway between the upper and lower portions of the protrusions.

FIG. 1e is a front elevation view illustrating the protrusions and lysing segment of an alternative embodiment of a tissue dissector and modifier, wherein the lysing segment connecting the two protrusions is positioned above the midline between the upper and lower portions of the protrusions.

FIG. 1f is a front elevation view illustrating the protrusions and lysing segment of an alternative embodiment of a tissue dissector and modifier, wherein the lysing segment connecting the two protrusions is positioned below the midline between the upper and lower portions of the protrusions.

FIG. 1g is a cross-sectional view of an embodiment of a TDM illustrating some examples of some of the canals that may be used with the device.

FIG. 2b is a side elevation view of the embodiment previously depicted in FIG. 2a.

FIG. 3a is a perspective view of an embodiment of a tissue dissector and modifier with a target-tissue-impedance-matched-microwave-based energy window on the upper side of the device.

FIG. 3b is a side elevation view of the embodiment previously depicted in FIG. 3a.

FIG. 3c is a front elevation view of some target-tissue-impedance-matched-microwave-based energy window components of an embodiment previously depicted in FIG. 3a.

FIG. 4b is a side elevation view of the embodiment previously depicted in FIG. 4a.

FIG. 5a is an upper plan view illustrating the protrusions and lysing segments of an embodiment of a tissue dissector and modifier, wherein some of the protrusions and lysing segments are oriented in a non-axial direction and the non-axial protrusions do not extend beyond the width of the distal shaft.

FIG. 5b is an upper plan view illustrating the protrusions and lysing segments of an alternative embodiment of a tissue dissector and modifier, wherein some of the protrusions and lysing segments are oriented in a non-axial direction and some of the non-axial protrusions extend beyond the width of the distal shaft.

FIG. 5c is a lower plan view of the embodiment of FIG. 5a illustrating the protrusions and lysing segments of a tissue dissector and modifier, wherein some of the protrusions and lysing segments are oriented in a non-axial direction and the non-axial protrusions do not extend beyond the width of the distal shaft.

FIG. 5d is a lower plan view of the embodiment of FIG. 5b illustrating the protrusions and lysing segments of a tissue dissector and modifier, wherein some of the protrusions and lysing segments are oriented in a non-axial direction and some of the non-axial protrusions extend beyond the width of the distal shaft.

FIG. 5e is an upper plan view illustrating the protrusions and lysing segments of an embodiment of a tip area of a tissue dissector and modifier.

FIG. 5f is an upper plan view illustrating the protrusions and lysing segments of an alternative embodiment of a tip area of a tissue dissector and modifier.

FIG. 5g is an upper plan view illustrating the protrusions and lysing segments of an alternative embodiment of a tip area of a tissue dissector and modifier.

FIG. 5h is a lower plan view illustrating the protrusions and lysing segments of an alternative embodiment of a tip area of a tissue dissector and modifier.

DETAILED DESCRIPTION

Figure 2A:
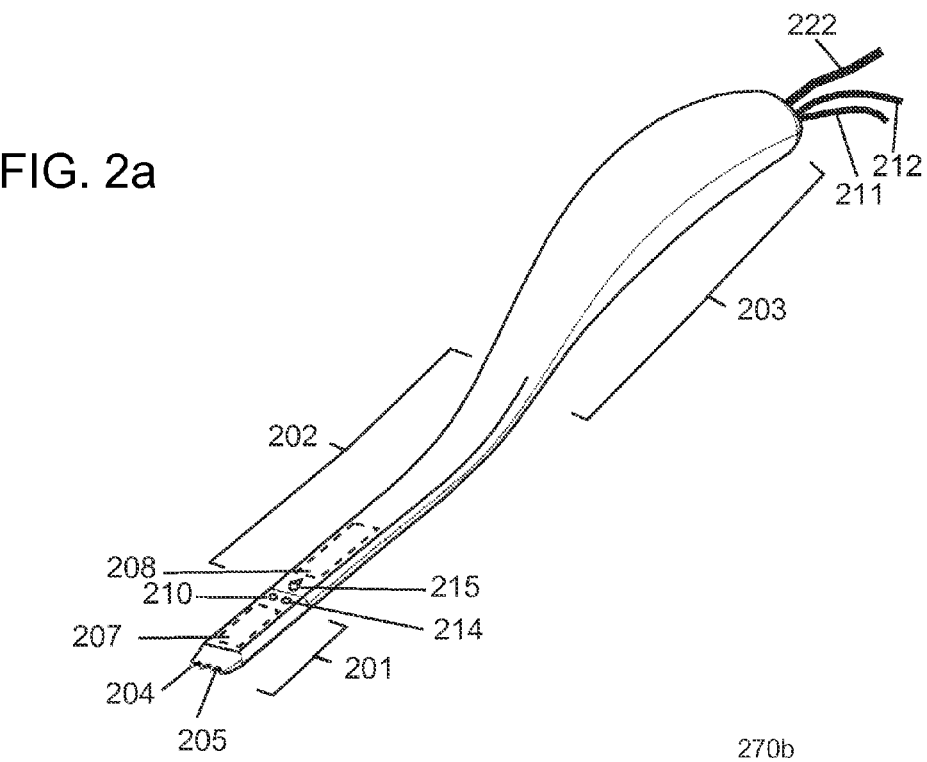
FIG. 2a is a perspective view of an embodiment of a tissue dissector and modifier with a ultrasound-based energy window on the upper side of the device.

The term dissection may indicate the separation of tissues or of one tissue plane from another (ref: Free Online Medical Dictionary). Some also consider dissection to comprise separation of a single tissue into portions. Much of the bodies of animals and humans are formed from embryonic fusion planes. Many of the organs of the human body are categorized from the embryonic fusion planes from whence they came.

The interfaces between organs may often be referred to as 'tissue planes.' Such planes may be considered substantially planar depending upon the size of a comparative planar living or inanimate object (such as a surgical instrument). As an example, a lobe of a human liver has a radius of curvature of about 5 cm; however, compared to a surgical instrument of about 1 cm in width capable of separating tissue in a plane, the curvilinear plane comprising the liver lobe may be 'substantially' planar and thus amenable to a tool capable of separating tissues in a 'substantially planar' fashion. Various vessels or ducts may also traverse within a given organ thus providing for areas of 'substantially planar' boundaries even within a given organ. Depending on the forces applied and/or available paths of least resistance, the TDM may divide what may appear to be isodense tissues. An example of separating isodense tissues may be separating one lobe of liver from another lobe within that liver. Depending on the density of a certain tumor, separation from the involved organ may also be an isodense dissection/separation. The TDM may perform the functions of sharp dissection, blunt dissection and electrosurgical cutting and/or coagulation without a surgeon having to switch instruments. Sharp dissection has been referred to by some as separation of tissues by means of the sharp edge of a knife or scalpel or with the inner sharp edge of scissors. Blunt dissection has been defined by Webster as surgical separation of tissue layers by means of an instrument without a cutting edge or by the fingers. The term 'Loose connective tissue' has been used to refer to a category of connective tissue which includes areolar tissue, reticular tissue, and adipose tissue. Loose connective tissue is the most common type of connective tissue in vertebrates. Loose connective tissue holds organs in place and attaches epithelial tissue to other underlying tissues; it also surrounds the blood vessels and nerves. Fibroblast cells are widely dispersed in this tissue; they are irregular branching cells that secrete strong fibrous proteins and proteoglycans as an extracellular matrix. The cells of this type of tissue are generally separated by quite some distance by a gel-like gelatinous substance primarily made up of collagenous and elastic fibers. Loose connective tissue is named based on the "weave" and type of its constituent fibers. There are three main types: Collagenous fibers: collagenous fibers are made of collagen and consist of bundles of fibrils that are coils of collagen molecules. Elastic fibers: elastic fibers are made of elastin and are "stretchable." Reticular fibers: reticular fibers consist of one or more types of very thin collagen fibers; these fibers join connective tissues to other tissues. (Reference: Wikipedia). Areolar tissue (Latin for a little open space) is a common type of connective tissue, and may also be referred to as "loose connective tissue". It is strong enough to bind different tissue types together, yet soft enough to provide flexibility and cushioning. It exhibits interlacing loosely organized fibers, abundant blood vessels, and significant low density space. Areolar tissue fibers run in random directions and are mostly collagenous, but elastic and reticular fibers are also present. Areolar tissue is highly variable in appearance. In many serous membranes, it appears as a loose arrangement of collagenous and elastic fibers, scattered cells of various types, abundant ground substance, and numerous blood vessels. In the skin and mucous membranes, areolar tissue may be more compact and sometimes difficult to distinguish from dense irregular connective tissue. Areolar tissue is the most widely distributed connective tissue type in vertebrates. It is sometimes equated with "loose connective tissue". In other cases, "loose connective tissue" is considered a parent category that includes mucous connective tissue, reticular connective tissue and adipose tissue. It may be found in tissue sections from almost every part of the body. It surrounds blood vessels and nerves and penetrates with them even into the small spaces of muscles, tendons, and other tissues. (wiki). Dr. Michael Kendrick, Surgeon at Mayo Clinic, Rochester, says many Mayo surgeons today simply refer to loose connective tissues between or within organs as areolar tissue.

The term 'minimally invasive surgery' has been used to describe a procedure (surgical or otherwise) that is less invasive than open surgery used for the same purpose. Some minimally invasive procedures typically involve use of laparoscopic devices and remote-control manipulation of instruments with indirect observation of the surgical field through an endoscope or similar device, and are carried out through the skin or through a body cavity or anatomical opening. This may result in shorter hospital stays, or allow outpatient treatment (reference: Wikipedia).

Various implementations of methods are disclosed herein for dissecting and modifying various living tissues. The term 'modifying' in this context may refer to or may encompass application of energy to tissue using one or more lysing segments as discussed herein. The term 'modifying' in this context may also refer to application of energy to tissue by way of an energy window as also described herein. Such methods may be performed using a Tissue Dissecting and Modifying Wand ("TDM"). Examples of various embodiments of such wands may be found in U.S. Pat. No. 6,203,540 titled "Ultrasound and Laser Face-Lift and Bulbous Lysing Device," U.S. Pat. No. 6,391,023 titled "Thermal Radiation Facelift Device," U.S. Pat. No. 6,432,101 titled "Surgical Device for Performing Face-Lifting Using Electromagnetic Radiation," U.S. Pat. No. 6,440,121 titled "Surgical Device For Performing Face-Lifting Surgery Using Radiofrequency Energy," U.S. Pat. No. 6,974,450 titled "Face-Lifting Device," and U.S. Pat. No. 7,494,488 titled "Facial Tissue Strengthening and Tightening Device and Methods." The "Detailed Description of the Invention" section of each of these patents is hereby incorporated herein by specific reference. With respect to U.S. Pat. No. 6,203,540 titled "Ultrasound and Laser Face-Lift and Bulbous Lysing Device," the section titled "Description of the Preferred Embodiments" is hereby incorporated herein by specific reference.

Tissues or organs or tumors treated with the TDM may also undergo post traumatic collagen deposition or scarring. Thermal damage to collagen is likely brought about by hydrolysis of cross-linked collagen molecules and reformation of hydrogen bonds resulting in loss of portions or all of the characteristic collagen triple-helix. New collagen formed as the result of trauma and some diseases is technically scar tissue. The encroachment of post traumatically derived collagen may influence already traumatized dissected tissue.

Some tissues of the body are of varying sensitivity to electrosurgical energy. Modulation and feedback may be helpful for such tissues. For example, some liver tumors or tissues may allow heating to temperature ranges higher than temperatures that typically be involved in facial rejuvenation procedures In some implementations, liver tumors or tissues may be operated upon by heating the tissue to a temperature range of about 72-85° C.

The TDM may dissect tissue planes of dissimilar density as well as isodense tissue planes. The TDM may also dissect different types of tissues from one another as well as dissect within an organ. It is possible that the cutting segments alone may traumatize or lyse portions of tissues sufficiently to carry out a given surgical method or procedure. It is also possible that when electrically energized with electro-cutting current, the TDM may possess a plasma field that may traumatize certain tumor cells in a potentially lethal fashion. The TDM may be "energized" by various forms of energy in its top side energy window, as described in greater detail below. Such energy absorptions may result in the formation of heat which may, in turn, damage tumor or other tissue cells themselves, and/or their surrounding environment in order to achieve a desired effect of a surgical method or procedure.

In some embodiments, energy may be delivered from one or more energy windows so as to heat tissue to a temperature of about 72° C. to about 80° C. Various methods may therefore be implemented in which the amount of energy and/or the delivery time may be adjusted so as to heat the tissue to within a desired temperature range. Temperature sensors may therefore be incorporated on or near the energy windows to allow a surgeon to heat the tissue to a desired temperature or within a desired temperature range. In some embodiments, the sensor may be configured to provide an average temperature over a particular period of time and or over a particular range of distances within the tissue. Systems consistent with the disclosure provided herein may be configured to prevent or to shut down or otherwise limit energy transfer if a particular tissue temperature were beyond a threshold or alternatively if an average temperature threshold is reached.

Temperature sensors that may be useful in connection with embodiments disclosed herein include, but are not limited to, resistance temperature sensors, such as carbon resistors, film thermometers, wire-wound thermometers, or coil elements. Some embodiments may comprise thermocouples, pyrometers, or non-contact temperature sensors, such as total radiation or photoelectric sensors. In some embodiments, one or more temperature sensors may be coupled with a processor and/or a monitor to allow a surgeon to better visualize or otherwise control the delivery of energy to selected areas of target tissue. For example, some embodiments may be configured such that a surgeon can visualize the temperature of tissue positioned adjacent to one or more locations along the TDM to ensure that such temperatures are within a desired temperature range. Some embodiments may alternatively, or additionally, be configured such that one or more temperature sensors are coupled with a processor in a feedback loop such that energy delivery may be automatically adjusted by the system in response to temperature data. For example, when temperatures exceed a particular threshold, such as somewhere between about 65° C. and about 90° C., the system may be configured to shut down or otherwise limit further energy delivery. In some such embodiments, the threshold may be between about 68° C. and about 75° C.

Some embodiments may comprise a feedback means, such as a visual, audible, or tactile feedback means, to provide information to a user to avoid excess energy delivery to tissues. In some embodiments, the feedback means may be configured to notify the surgeon when the temperature has reached a particular threshold. In some embodiments, the feedback means may be configured to notify the surgeon when the TDM has been positioned in a particular location within the target region for a particular time period. Examples of visual feedback means include LED lights, LASERS, visual light source, display screen, etc. Examples of audible feedback means include speakers, alarms, audible vibration, etc., Examples of tactile feedback means include vibration, minimal electrical shock, heat, etc., The feedback means may be configured with multiple thresholds with different feedback at each threshold. For example, at a first threshold, the TDM may be configured to deliver a first noise and at a second threshold the TDM may be configured to deliver a second noise. The second noise may be louder than the first noise to indicate a greater urgency for changing the energy delivery and/or moving the TDM from its current location within a patient's body. In some embodiments, an antenna(s) may be present on the shaft or tip of the TDM. In some embodiments, a camera or fiberoptic may gather optical data to allow the surgeon knowledge of the placement of the TDM.

In some implementations of methods according to the present disclosure, the TDM may be used to induce post-surgical collagen deposition and/or an inflammatory tissue reaction in the target zone. Some procedures intended to increase post-surgical collagen deposition, for example, around a mesh implant, using the TDM are done by delivering energies of about 20 $J/cm^2$. By contrast, in certain preferred implementations of methods for increasing post-surgical collagen deposition using the TDM, a higher energy delivery may be employed than 20 $J/cm^2$. For example, some implementations for increasing post-surgical collagen deposition may be performed by delivering energy at a level 20% or more than 20 $J/cm^2$.

Further details regarding various embodiments will now be provided with reference to the drawings.

FIG. 1a is a perspective view of an embodiment of a TDM with an electrosurgically energized energy window 107 on the upper side of the device. It should be noted that the term "energy window" is intended to encompass what is referred to as a planar-tissue-altering-window/zone in U.S. Pat. No. 7,494,488 and, as described later, need not be electrosurgically energized in all embodiments. In some embodiments, the "energy window" may comprise a variety of other energy emitting devices, including radiofrequency, intense pulsed light, LASER, thermal, microwave and ultrasound. It should also be understood that the term "energy window" does not necessarily imply that energy is delivered uniformly throughout the region comprising the energy window. Instead, some energy window implementations may comprise a series of termini or other regions within which energy is delivered with interspersed regions within which no energy, or less energy, is delivered. This configuration may be useful for some implementations to allow for alteration of certain tissue areas with interspersed areas within which tissue is not altered, or at least is less altered. This may have some advantages for certain applications due to the way in which such tissue heals. It is contemplated that in alternative embodiments, electronically energized energy window 107 may be omitted.

FIG. 1a is a perspective view of an embodiment of a TDM comprising a tip 101, a shaft 102 and a handle 103.

Electro-coagulation and electro-cutting energy arrives in electrical conduits 111 and/or 112 and may travel by wiring through the handle and shaft to termini 107a, which are part of energy window 107. Electro-cutting and electro-coagulation currents may be controlled outside the TDM at an electrosurgical generator, such as the Bovie Aaron 1250™ or Bovie Icon GP™.

In the depicted embodiment, energy window 107 comprises an electrosurgical energy window. In the depicted embodiment, energy window 107 comprises one or more electrosurgical elements. In the depicted embodiment, energy window 107 comprises one or more hollow protruding ceramic termini 107a atop a nonconductive ceramic plate; one or more conductive metal pins pass may through the hollow termini and may be electrically connected to electrical leads which may pass through said conduits. In the depicted embodiment, the metal pins, of termini 107a, comprise surgical stainless steel pins. In an alternative embodiment, the metal pins comprise an electroconductive coating such as for example, Silverglide® coating (from Stryker, Silverglide® Surgical, Kalamazoo, Mich., USA) and/or gold and/or titanium nitride (Strem Chemicals Inc., Newburyport, Mass., USA). Such electroconductive coats may reduce carbonized debris build up and enhance electrical transmission into target tissues. In the depicted embodiment, nonconductive hollow ceramic termini 107a protrude about 2 mm above the plane of energy window 107, which is flush with the plane of tip 101 and shaft 102. In some embodiments, energy window 107 may protrude above the plane of tip 101 and/or shaft 102. In an embodiment energy window 107 may measure about 10 mm×15 mm. In some embodiments, energy window 107 may lie below the plane of tip 101 and/or shaft 102. In contemplated embodiments, nonconductive hollow ceramic termini 107a may protrude a range of about 0.5 mm-20 mm above the plane of the energy window. In the depicted embodiment, one or more holes in termini 107a measure about 1.5 mm in diameter and/or conductive pins measure 1.2 mm in diameter. In the depicted embodiments, electrocoagulation current reaches metallic termini of tips 107a from a standard hospital electrosurgical generator. Such standard electrosurgical generators, which may be used to power an electrosurgical energy window, may include those manufactured by Bovie Medical, i.e. Model Aaron1250 and IconGP (Clearwater, Fla., USA) and/or Valleylab/Covidian Model Surgistat 2 (Boulder, Colo.) and/or Erbe Electrosurgical (Tubingen, Germany) etc. Such electrosurgical generators may have a maximal output power that may range from about 80 W to 120 W. In some implementations for electrosurgical energy window settings, said electrosurgical generators are operated on a 'Coag/Coagulation' power setting of 20-80% of maximal output while the TDM is motionless and/or moved by the surgeon. In some implementations, the TDM is moved at about 1 cm per second by the surgeon. In some implementations the electrocoagulation energy reaching electrosurgical energy window is pulsed at a rate ranging from about 20 cycle per second to 50 cycles per second. In some implementations the electrocoagulation energy reaching electrosurgical energy window is pulsed at rates ranging from about 1 cycle per second to 200 cycles per second. In some embodiments, the electrosurgically energized window current can be further pulsed at varying rates, by interpolating gating circuitry at some point external to the electrosurgical generator by standard mechanisms known in the art. In some embodiments, the electrosurgically energized window current can be further pulsed at varying rates by gating circuitry within the electrosurgical generator by standard mechanisms known in the art.

In some embodiments, the electrosurgical energy window 107 may be located on shaft 102. In alternative contemplated embodiments, the electrosurgical energy window 107 comprises an electroconductive plate with termini, encased by an electrical insulator coat except at one or more points on termini. In some embodiments termini are pressed into the electroconductive plate. In some embodiments the electroconductive plate comprises a metal plate and/or a cermet. In an embodiment, the metal plate comprises surgical stainless steel. In some embodiments, the electroconductive plate and/or termini may be directly coated with an electroconductive coating such as for example, Silverglide® coating (from Stryker, Silverglide® Surgical, Kalamazoo, Mich., USA) and/or gold and/or titanium nitride (Strem Chemicals Inc., Newburyport, Mass., USA). In some embodiments the electroconductive plate may be coated with an electrically insulating coat. In some embodiments, an electroconductive coat is placed upon the electroconductive plate before an insulating coat. In some embodiments, the electrical insulator comprises a nonconductive anti-stick polymer such as polytetrafluoroethylene. In some embodiments a nonconductive coating may cover an electroconductive place ranging from about 90% coverage to 98% coverage. In other embodiments coverage may range from about 5% to about 90%. In another embodiment, the insulated electroconductive plate may be substantially planar and may comprise one or more defects in the insulating surface coating which may allow one or more exit points for electrons (electrosurgical energy). In some embodiments, the geometry of one or more of such defects is circular and/or square and/or triangular and/or geometric in shape. In some embodiments, the diameter of the geometric defect in the insulating layer covering may range from about 1 mm to about 20 mm In some embodiments, the defects may form a pattern.

In an embodiment, the tip may measure about 1 cm in width and about 1-2 mm in thickness. Sizes of about one-fifth to about five times these dimensions may also have possible uses. In some veterinary embodiments, tip sizes of about one-tenth to 20 times the aforementioned dimensions may also have possible uses. In some embodiments, the tip can be a separate piece that is secured to shaft by a variety of methods such as a snap mechanism, mating grooves, plastic sonic welding, etc. Alternatively, in some other embodiments, the tip can be integral or a continuation of shaft made of similar metal or materials. In some embodiments, the tip may also be constructed of materials that are both electrically non-conductive and of low thermal conductivity; such materials might comprise, for example, porcelain, ceramics, glass-ceramics, plastics, varieties of polytetrafluoroethylene, carbon, graphite, and graphite-fiberglass composites.

In some embodiments, the tip may be constructed of a support matrix of an insulating material (e.g., ceramic or glass material such as alumina, zirconia). External conduits 111 and/or 112 may connect to electrically conductive elements to bring RF electrosurgical energy from an electrosurgical generator down the shaft 102 to electrically conductive lysing elements 105 mounted in the recessions in between the protrusions 104. In some embodiments, the protrusions may comprise bulbous protrusions. The tip shown in this embodiment has four relative protrusions and three relative recessions and provides for a monopolar tip conductive element. All of the axes of the relative protrusions of the tip depicted in this embodiment extend at least substantially parallel to the axis of the shaft of the TDM (as viewed from Top). In embodiments of tips of such axial placement of protrusions and or relative recessions, surgeons may use methods of defining and or dissecting a target area by entering through an incision and then moving the TDM tip in a primarily axial direction forward and backward and reorienting the TDM after the backstroke in a spokewheel pattern the TDM to access tissues adjacent to earlier strokes.

In the depicted embodiment, the tip 101 may alternatively be made partially or completely of concentrically laminated or annealed-in wafer layers of materials that may include plastics, silicon, glass, glass/ceramics, cermets or ceramics. Lysing elements 105 may also be made partially or completely of a cermet material. Alternatively, in a further embodiment the tip may be constructed of insulation covered metals or electroconductive materials. In some embodiments, the shaft may be flat, rectangular or geometric in cross-section or substantially flattened. In some embodiments, smoothing of the edges of the shaft may reduce friction on the skin surrounding the entrance wound. In some further embodiments, the shaft may be made of metal or plastic or other material with a completely occupied or hollow interior that can contain insulated wires, electrical conductors, fluid/gas pumping or suctioning conduits, fiber-optics, or insulation. In some embodiments the shaft may have a length of about 10-20 cm. In some embodiments the handle may have a length of about 8-18 cm.

In some embodiments, shaft plastics, such as polytetrafluoroethylene may act as insulation about wire or electrically conductive elements. In some embodiments, the shaft may alternatively be made partially or completely of concentrically laminated or annealed-in wafer layers of materials that may include plastics, silicon, glass, glass/ceramics, ceramics carbon, graphite, graphite-fiberglass composites. Depending upon the intended uses for the device, an electrically conductive element internal to shaft may be provided to conduct electrical impulses or RF signals from an external power/control unit (such as a Valleylab™ electrosurgical generator) to another energy window 108. In some embodiments, energy windows 107 and/or 108 may only be substantially planar, or may take on other cross-sectional shapes that may correspond with a portion of the shape of the shaft, such as arced, stair-step, or other geometric shapes/curvatures. In the embodiments depicted in FIGS. 1a & 1b, energy window 107 is adjacent to protrusions 104, however other embodiments are contemplated in which an energy window may be positioned elsewhere on the shaft 102 or tip 101 of the wand, and still be considered adjacent to protrusions 104. For example, in an embodiment lacking energy window 107, but still comprising energy window 108, energy window 108 would still be considered adjacent to protrusion 104. However, if an energy window was placed on handle 103, such an energy window would not be considered adjacent to the protrusions 104.

The conduit may also contain electrical control wires to aid in device operation. Partially hidden from direct view in FIGS. 1a & 1b, and located in the grooves defined by protrusions 104 are electrically conductive tissue lysing elements 105, which, when powered by an electrosurgical generator, effects lysing of tissue planes on forward motion of the device. The lysing segments may be located at the termini of conductive elements. In some embodiments, one or more sensors such as for example sensors 110 and 114 may be positioned on the device. The sensors 110 and 114 may comprise any of the sensors described in the specification herein. Other embodiments may comprise one or more sensors on any other suitable location on the TDM, including but not limited to on the protrusions or otherwise on the tip, and on the shaft. Sensors that may be useful include thermal sensors, photoelectric or photo optic sensors, cameras, etc. In some embodiments, one or more sensors may be used to monitor the local post passage electrical impedance or thermal conditions that may exist near the distal tip of the shaft or on the tip. Some embodiments may also comprise one or more sensors incorporating MEMS (Micro Electro-Mechanical Systems) technology, such as MEMS gyroscopes, accelerometers, and the like. Such sensors may be positioned at any number of locations on the TDM, including within the handle in some embodiments. In some embodiments, sensor 114 may comprise fiberoptic elements. In an embodiment, the sensor can be configured to sense a temperature of tissue adjacent to the apparatus. The temperature sensor may alternatively be configured or sense a temperature of one or more fluids adjacent to the apparatus such as for example tissue fluids and/or fluids introduced by the surgeon.

Temperature and impedance values may be tracked on a display screen or directly linked to a microprocessor capable of signaling control electronics to alter the energy delivered to the tip when preset values are approached or exceeded. Typical instrumentation paths are widely known, such as thermal sensing thermistors, and may feed to analog amplifiers which, in turn, feed analog digital converters leading to a microprocessor. In some embodiments, internal or external ultrasound measurements may also provide information which may be incorporated into a feedback circuit. In an embodiment, an optional mid and low frequency ultrasound transducer may also be activated to transmit energy to the tip and provide additional heating and may additionally improve lysing. In some embodiments, a flashing visible light source, for example, an LED, can be mounted on the tip may show through the tissues and/or organs to identify the location of the device.

In some embodiments, one or more electromagnetic delivery elements 115 may be positioned on tip or shaft. Other embodiments may comprise one or more electromagnetic delivery elements on any other suitable location on the TDM, including but not limited to on the protrusions or otherwise on the tip, and on the shaft. Electromagnetic delivery elements that may be useful include: LEDs, LASERs, fiberoptics, filaments, photoelectric materials, infrared emitters, etc.

Some embodiments may comprise a low cost, disposable, and one-time-use device. However, in some embodiments intended for multiple uses, the tip's electrically conductive tissue lysing elements be protected or coated with materials that include, but are not limited to, Silverglide™ non-stick surgical coating, platinum, palladium, gold and rhodium. Varying the amount of protective coating allows for embodiments of varying potential for obsolescence capable of either prolonging or shortening instrument life.

In some embodiments, the electrically conductive lysing element portion of the tip may arise from a plane or plate of varying shapes derived from the aforementioned materials by methods known in the manufacturing art, including but not limited to additive manufacturing, cutting, stamping, pouring, molding, filing and sanding. In some embodiments, the electrically conductive lysing element 105 may comprise an insert attached to a conductive element in the shaft or continuous with a formed conductive element coursing all or part of the shaft. In some embodiments, one or more electrically conductive elements or wiring in conduit 111 and/or 112 brings RF electrosurgical energy down the shaft to electrically conductive lysing elements 105 associated in part with the recessions. In an embodiment, the electrosurgical energy via conduit 111 is predominately electro-cutting and/or a blend.

In some embodiments, the electrically conductive element or wiring may be bifurcated to employ hand switching if an optional finger switch is located on handle. The electrically conductive element or wiring leading from the shaft into the handle may be bundled with other electrical conduits or energy delivering cables, wiring and the like and may exit the proximal handle as insulated general wiring to various generators (including electrosurgical), central processing units, lasers and other sources as have been described herein. In some embodiments, the plate making up lysing segments 105 may be sharpened or scalloped or made to slightly extend outwardly from the tip recessions into which the plate will fit.

Alternatively, in some embodiments, since cutting or electrical current may cause an effect at a distance without direct contact, the lysing element may be recessed into the relative recessions or grooves defined by the protrusions 104 or, alternatively, may be flush with protrusions 104. In some further adjustable embodiments, locations of the electrically conductive lysing elements with respect to the protrusions may be adjusted by diminutive screws or ratchets. In some further adjustable embodiments, locations of the electrically conductive lysing elements with respect to the protrusions may be adjusted by MEMS or microelectronics. The plate, which in some embodiments is between 0.01 mm and 1 mm thick, can be sharpened to varying degrees on its forward facing surface. It is possible that plate sharpness may increase the efficiency with which electricity will pass from the edge cutting the target tissue. Sometimes, however, proper function even when variably dull or unsharpened may be unhampered since electrosurgical cutting current may cut beyond the electroconductive edge by a distance of over 1 mm. In some embodiments, the plate thickness may vary from 0.001 mm to 3 mm thick.

In some embodiments, the electrically conductive lysing element may also exist in the shape of a simple wire of 0.1 mm and 1 mm 0.01 mm to 3 mm. In some embodiments, the wire may measure between 0.01 mm to 3 mm. Such a wire may be singly or doubly insulated as was described for the plate and may have the same electrical continuities as was discussed for the planar (plate) version. In some embodiments, an electrosurgical current for the electrically conductive lysing element is of the monopolar "cutting" variety and setting and may be delivered to the tip lysing conductor in a continuous fashion or, alternatively, a pulsed fashion. The surgeon can control the presence of current by a foot pedal control of the electrosurgical generator or by button control on the shaft (forward facing button). The amount of cutting current may be modified by standard interfaces or dials on the electrosurgical generator. For some embodiments, the electrically conductive lysing element is a monopolar tip in contact with conductive elements in the shaft leading to external surgical cable leading to an electrosurgical generator from which emanates a grounding or dispersive plate which may be placed elsewhere in contact with the patient's body, such as the thigh. Such circuitry may be controlled and gated/wired from the cutting current delivery system of the electro surgical generator. In an embodiment, the tip may also be manufactured from multilayer wafer substrates comprised of bonded conductive strips and ceramics. Suitable conductive materials include but are not limited to those already described for tip manufacture.

In alternative embodiments, the electrically conductive lysing elements may be bifurcated or divided into even numbers at the relative recessions, insulated and energized by wiring to an even number of electrical conduits in a bipolar fashion and connected to the bipolar outlets of the aforementioned electrosurgical generators. Rings partly or completely encircling the shaft of the hand unit can be linked to a partner bipolar electrode at the tip or on the energy window. Such bipolar versions may decrease the available power necessary to electrically modify certain tissues, especially thicker tissues. In alternative embodiments, the lysing elements may be divided into odd numbers yet still allow for bipolar flow between two or more elements as those of ordinary skill in the art would appreciate.

FIG. 1b is a side elevation view of the embodiment previously depicted in FIG. 1a. In the depicted embodiment, tip 101 may be made of materials that are both electrically non-conductive and of low thermal conductivity such as porcelain, epoxies, ceramics, glass-ceramics, plastics, or varieties of polytetrafluoroethylene. Alternatively, the tip may be made from metals or electroconductive materials that are completely or partially insulated. Note the relative protrusions and relative recessions are not completely visible from this viewing angle. In some embodiments, the relative recessions of the tip is the electrically conductive tissue lysing element 105 (usually hidden from view at most angles) which may have any geometric shape including a thin cylindrical wire; the electrically conductive lysing element can be in the shape of a plate or plane or wire and made of any metal or alloy that does not melt under operating conditions or give off toxic residua. Optimal materials may include but are not limited to steel, nickel, alloys, palladium, gold, tungsten, silver, copper, and platinum. Metals may become oxidized thus impeding electrical flow and function. In alternative embodiments the geometry of the tip area may comprise protrusions that are not oriented along the axis of the shaft (as seen from a top view); some of these alternative embodiments for tip area geometries are depicted in FIGS. 5a,b,c,d,e,f,g,h and FIGS. 6a,b,c,d. Some embodiments may be configured to be modular and/or comprise disposable tips such that a surgeon can place an appropriate tip for a particular surgery on the shaft. Alternatively or additionally one or more of the tips may be disposable such that a surgeon may dispose of the tip after performing surgery and install a new tip for subsequent surgeries or a continuation of the current surgery with a new tip.

In some embodiments, one or more suction/vacuum ports 117 may be provided on or about the tip or distal shaft. The port(s) may be fluidly coupled with a vacuum; the vacuum may comprise a pump or a negative pressure chamber or a syringe at the end of a fluid conduit. Other embodiments may comprise one or more suction/vacuum ports on any other suitable location on the TDM, including but not limited to on the protrusions or otherwise on the tip, and on the shaft. In some embodiments, a fluid delivery port 116 may be provided. In some embodiments the fluid delivery port may be coupled with a pump or high pressure fluid. In some embodiments the port may be perpetually open such that fluid may be delivered therethrough upon actuation of a pump or fluid pressure system. In other embodiments the port may be closed and selectively opened to deliver fluid therethrough. Other embodiments may comprise one or more fluid ports on any other suitable location on the TDM, including but not limited to on the protrusions or otherwise on the tip, and on the shaft. Fluid ports that may be useful may comprise channels within the TDM, polymer lines, hoses, etc. Fluids that may emanate from the outlet may comprise ionic fluids such as saline, medicines (including but not limited to antibiotics, anesthetics, antineoplastic agents, bacteriostatic agents, etc.), non-ionic fluids, and or gasses (including but not limited to nitrogen, argon, air, etc.). In some embodiments fluids may be under higher pressures or sprayed. It should be understood that although these elements (116 & 117) are not depicted in every one of the other figures, any of the embodiments described herein may include one or more such elements.

In some embodiments, a vibration means 170b may be positioned in the handle. Other embodiments may comprise one or more vibration means on any other suitable location on the TDM, including but not limited to on the protrusions or otherwise on the tip, and on the shaft. Examples of suitable vibration means may include piezoelectric materials, ultrasonic motors with stators, piezoelectric actuators, vibration motor such as an off-center weight mounted on a gear, etc. Some vibration means may be configured to emit ultrasound in the 20-40 kHz range. Yet other vibration means may include electromagnet drivers with a frequency of operation in the range of 150-400 Hz. In some embodiments, one or more vibration means may be used to provide additional forces which may facilitate passage of the TDM. In some embodiments, one or more vibration means may be used to reduce debris on the electrosurgical or other components of the TDM. In a further embodiment, a vibration means may be directly or indirectly connected to one or more of the lysing segments. Some vibration means may help to decrease and/or remove debris. In some embodiments use of a vibration means may, also or alternatively, be used to assist in migrating the TDM through tissue during the procedure. In some such embodiments, it is thought that use of a vibration means having a lower frequency may be particularly useful for assisting in such migration. In addition, positioning the vibration means closer to a handle of the TDM may facilitate such migration as well. By contrast, positioning the vibration means on or near the tip, and/or using a higher frequency vibrations means may be particularly useful for preventing buildup of debris on the tip.

In the depicted embodiment, 118 represents an antenna configured to deliver a signal to a receiver unit. In some embodiments, antenna 118 may comprise a radiofrequency identification (RFID) TAG. In some embodiments the RFID tag may comprise an RFID transponder. In other embodiments the RFID tag may comprise a passive tag. It should be understood that antenna 118 is not depicted in every one of the other figures, any of the embodiments described herein may comprise one or more such elements. Other embodiments may comprise one or more antenna on any other suitable location on the TDM, including but not limited to on the protrusions or otherwise on the tip, and on the shaft. In embodiments in which antenna 118 comprises an RFID transponder, the RFID transponder may comprise a microchip, such as a microchip having a rewritable memory. In some embodiments, the tag may measure less than a few millimeters. In some embodiments a reader may generate an alternating electromagnetic field which activates the RFID transponder and data may be sent via frequency modulation. In an embodiment, the position of the RFID tag or other antenna may be determined by an alternating electromagnetic field in the ultra-high frequency range. The position may be related to a 3 dimensional mapping of the subject. In an embodiment the reader may generate an alternating electromagnetic field. In some such embodiments, the alternating electromagnetic field may be in the shortwave (13.56 MHz) or UHF (865-869 MHz) frequency. Examples of potentially useful systems and methods for mapping/tracking a surgical instrument in relation to a patient's body may be found in U.S. Patent Application Publication No. 2007/0225550 titled "System and Method for 3-D Tracking of Surgical Instrument in Relation to Patient Body, which is hereby incorporated by reference in its entirety.

In some embodiments, a transmission unit may be provided that may generate a high-frequency electromagnetic field configured to be received by an antenna of the RFID tag or another antenna. The antenna may be configured to create an inductive current from the electromagnetic field. This current may activate a circuit of the tag, which may result in transmission of electromagnetic radiation from the tag. In some embodiments, this may be accomplished by modulation of the field created by the transmission unit. The frequency of the electromagnetic radiation emitted by the tag may be distinct from the radiation emitted from the transmission unit. In this manner, it may be possible to identify and distinguish the two signals. In some embodiments, the frequency of the signal from the tag may lie within a side range of the frequency of the radiation emitted from the transmission unit. Additional details regarding RFID technology that may be useful in connection with one or more embodiments discussed herein may be found in, for example, U.S. Patent Application Publication No. 2009/0281419 titled "System for Determining the Position of a Medical Instrument," the entire contents of which are incorporated herein by specific reference.

In other embodiments, antenna 118 may comprise a Bluetooth antenna. In such embodiments, multiple corresponding Bluetooth receivers at known locations may be configured to sense signal strengths from the Bluetooth antenna 118 and triangulate such data in order to localize the signal from the Bluetooth antenna 118 and thereby locate the TDM within a patient's body. Other embodiments may be configured to use angle-based, electronic localization techniques and equipment in order to locate the antenna 118. Some such embodiments may comprise use of directional antennas, which may be useful to increase the accuracy of the localization. Still other embodiments may comprise use of other types of hardware and/or signals that may be useful for localization, such as WIFI and cellular signals, for example.

One or more receiver units may be set up to receive the signal from the tag. By evaluating, for example, the strength of the signal at various receiver units, the distances from the various receiver units may be determined. By so determining such distances, a precise location of the TDM relative to a patient and/or a particular organ or other surgical site on the patient may be determined. In some embodiments, a display screen with appropriate software may be coupled with the RFID or other localization technology to allow a surgeon to visualize at least an approximate location of the tag/antenna, and therefore TDM, relative to the patient's body.

Some embodiments may be further configured such that data from the antenna(s) may be used in connection with sensor data from the TDM. For example, some embodiments of TDMs comprising one or more sensors may be further configured with one or more RFID tags. As such, data from the one or more sensors may be paired or otherwise used in connection with data from the one or more RFID tags or other antennas. For example, some embodiments may be configured to provide information to a surgeon regarding one or more locations on the body from which one or more sensor readings were obtained. To further illustrate using another example, information regarding tissue temperature may be combined with a location from which such tissue temperature(s) were taken. In this manner, a surgeon may be provided with specific information regarding which locations within a patient's body have already been treated in an effective manner and thus which locations need not receive further treatment using the TDM.

In some such embodiments, a visual display may be provided comprising an image of the patient's body and/or one or more selected regions of a patient's body. Such a system may be configured so as to provide a visual indication for one or more regions within the image corresponding to regions of the patient's tissue that have been sufficiently treated. For example, a display of a patient's liver may change colors at locations on the display that correspond with regions of the liver that have experienced a sufficient degree of fibrosis or other treatment. Such regions may, in some embodiments, be configured such that pixels corresponding to particular regions only light up after the corresponding tissue in that region reaches a particular threshold temperature.

Such sensors 110 and/or 114, 210 and/or 214, 310 and/or 314, 410 and/or 414, 510a and/or 514a, 510b and/or 514b, 610a and/or 614a, 610b and/or 614b, may be coupled with an antenna, which may send and/or receive one or more signals to/from a processing unit. Alternatively, or additionally, data from such sensors resulting from tissue and/or fluid analysis using such sensors may be stored locally and transmitted later. As yet another alternative, such a signal may be transmitted following surgery. In such implementations, the signals need not necessarily be transmitted wirelessly. In fact, some embodiments may be configured to store data locally, after which a data module, such as a memory stick, may be removed from the TDM and uploaded to a separate computer for analysis.

In some embodiments tip 101 may be attached to a robotic arm. In some embodiments, tip 101 and portion of shaft 102 may be attached to a robotic arm. In some embodiments tip 101 and/or a portion of shaft 102 and/or a portion shaft and/or portion of handle 103 may be attached to a robotic arm. In some embodiments, the robotic arm may comprise one or more motors such as a screw-drive motor, gear motor, hydraulic motors, etc. In some embodiments the robotic arm system may comprise worm gearheads, video cameras, motor control circuits, monitors, remote control devices, illumination sources, tactile interface, etc.

FIG. 1c is a front elevation view of an embodiment of the embodiment previously depicted in FIG. 1a. In this depicted embodiment, there are 4 protrusions and 3 lysing segment recessions 105c; the vertical height of a protrusion may be about 3 mm and the horizontal width may be about 2 mm. In this depicted embodiment, the relatively oval protrusions 104c may be shaped similarly to a commercial jetliner nose cone in order to reduce drag and lower resistance to facilitate tissue passage. In some embodiments, tip protrusion shapes may take on a wide variety of geometric shapes including, but not limited to, stacked rectangles or tapered thin rectangles as discussed elsewhere. In some further embodiments the relative projection shapes that may include, but should not be limited to: spheroid, sphere, sphere on cylinder, sphere on pyramid, sphere on cone, cone, cylinder, pyramid, and polyhedron.

FIG. 1d is a front elevation view of an alternative embodiment having two protrusions 104d and one lysing segment (recession) wherein the lysing segment 105d connecting the two protrusions is substantially centered midway between the upper and lower portions of the protrusions. In the depicted embodiment, the vertical height of the protrusions may be about 3 mm and the horizontal width may be about 2 mm. Thus, the lysing segment may be placed about 1.5 mm from the upper portion of the protrusion. FIG. 1e is a front elevation view of another embodiment having two protrusions and one lysing segment 105e wherein the lysing segment connecting the two protrusions 104e is substantially centered in the upper third of the way (on the upper side) between the upper and lower portions of the protrusions. In the depicted embodiment, the vertical height of the protrusions may be about 3 mm and the horizontal width may be about 2 mm. Thus, the lysing segment may be placed about 1 mm from the upper portion of the protrusion.

FIG. 1f is a front elevation view of another embodiment having two protrusions and one lysing segment wherein the lysing segment 105f connecting the two protrusions 104f is substantially centered in the lower third (on the lower side) between the upper and lower portions of the protrusions. In the depicted embodiment, the vertical height of the protrusions may be about 3 mm and the horizontal width may be about 2 mm. Thus, the lysing segment may be placed about 2 mm from the upper portion of the protrusion. As discussed above, some embodiments may be configured such that the position of the lysing segment(s) relative to the protrusions is adjustable, such as adjustable between the embodiments shown in FIGS. 1d-1f.

FIG. 1g is a cross-sectional view of an embodiment of a TDM illustrating some examples of some of the canals that may be used with the device. For example, canal 130 may comprise an electrode canal for delivering electrical energy to one or more of the lysing segments and/or the energy window(s). Canal 132 may comprise an optics canal for delivering and/or receiving optical signals or energy, such as a LASER, fiber optics, intense pulse light, or for receiving an optical sensor. Canal 134 may comprise a vacuum tube for sucking fluids away from the surgical site, such as bodily fluids and/or fluids introduced by the TDM during the surgery. One or more of these canals may be configured for delivering one or more fluids using the TDM. For example, canal 136 may comprise a fluid delivery canal for delivering an ionic fluid, such as a saline solution. Canal 136 may be configured to deliver a fluid that is both ionic and an anesthetic, such as a tumescent anesthesia. In some embodiments, canal 136 may be configured to deliver a fluid containing multiple individual fluids, such as a Klein Formula. Canal 138 may serve as a coaxial cable canal, such as for delivering a microwave signal to the energy window, for example. Canals 140 and 142 may comprise duplicates of any one of the foregoing canals 130-138. One or more of the canals 130-142 may be coated with copper or another conductive metal to insulate the signals from those within other canals. It should be understood that although these canals are not depicted in other figures, any of the embodiments described herein may comprise one or more such canals configured for any of the uses described herein. It should also be understood that although the canals shown in FIG. 1g are shown as having rectangular cross sections, any other cross sectional shape, including but not limited to circular cross sections, may be used.

FIG. 2a is a perspective view of an embodiment of a TDM with an alternative energy window 207 on the upper side of the device configured to emit ultrasonic energy. It should be noted that the term "energy window" is intended to encompass what is referred to as a planar-tissue-altering-window/zone in U.S. Pat. No. 7,494,488 and, as described herein, need not contain an ultrasonic energy emitter in all embodiments. In some embodiments, the "energy window" may comprise a variety of other energy emitting devices, including radiofrequency, intense pulsed light, LASER, thermal, microwave and ultrasonic. It should also be understood that the term "energy window" does not necessarily imply that energy is delivered uniformly throughout the region comprising the energy window. Instead, some energy window implementations may comprise a series of termini or other regions within which energy is delivered with interspersed regions within which no energy, or less energy, is delivered. This configuration may be useful for some implementations to allow for alteration of certain tissue areas with interspersed areas within which tissue is not altered, or at least is less altered. This may have some advantages for certain applications due to the way in which such tissue heals. In some embodiments, certain components of an energy window, such as the electroconductive components of the energy window, could comprise a cermet. It is contemplated that in alternative embodiments, ultrasound containing energy window 207 may be omitted.

FIG. 2a is a perspective view of an embodiment of a TDM comprising a tip 201, a shaft 202 and a handle 203. Electrical energy may be delivered in conduit 222 through the handle and shaft to energy window 207, which may comprise an ultrasonic energy emitter. A second energy window 208 may also be included in some embodiments, and may comprise yet another ultrasonic energy emitter or another variety of energy emitting device. An ultrasonically energized energy window 207 may be present on the upper side of the device. It is contemplated that in alternative embodiments, energy window 207 may be omitted. It should be noted that the term "energy window" is intended to encompass what is referred to as a planar-tissue-altering-window/zone in U.S. Pat. No. 7,494,488 and, as described later, need not be ultrasonically energized in all embodiments. In some embodiments, the "energy window" may comprise a variety of other energy emitting devices, including radiofrequency, intense pulsed light, LASER, thermal, microwave and electrical. It should also be understood that the term "energy window" does not necessarily imply that energy is delivered uniformly throughout the region comprising the energy window. Instead, some energy window implementations may comprise a series of energy delivering elements or other regions within which energy is delivered with interspersed regions within which no energy, or less energy, is delivered. An ultrasonic energy window configuration may be useful for some implementations, depending upon piezoelectric component and/or energy applied to less aggressively disrupt tissues (in order to possibly increase the concentration of target chemicals and/or biological compounds) at the cellular level to increase the availability of biological and/or chemical components to be sensed/analyzed and/or (may be at higher energy levels) to allow for alteration and/or damage to targeted tissues and/or heating for treatment. A second energy window may also be included in some embodiments, and may comprise a microwave emission device or another variety of energy emitting device. Energy window 207 may only be at least substantially planar, or may take on other cross-sectional shapes that may correspond with a portion of the shape of the shaft, such as arced, stair-step, or other geometric shapes/curvatures.

Ultrasonic Energy Window 207 may be configured to heat target tissues and/or fluids. In the depicted embodiment, Ultrasonic Energy Window 207 comprises a piezoelectric ceramic. In an embodiment the piezoelectric ceramic may measure about 20 mm×8 mm×3 mm. In some embodiments, the piezoelectric ceramic may measure up to about 50 mm in diameter. It is contemplated that in alternative embodiments, Ultrasonic Energy Window 207 may be omitted. In some embodiments the piezoelectric ceramic is made from lead zirconate titanate piezoelectric ceramic (which may be sold as PZT8 or PZT4 by Micromechatronics, State College, Pa.). In some embodiments the piezoelectric may comprise quartz and/or barium titanate and/or film polymer polyvinylidene fluoride. In some embodiments the ultrasonic energy window measures between 1 mm and 50 mm in any dimension. Some embodiments may comprise a plurality of ultrasonic energy windows. Depending upon the composition of a piezoelectric and/or the surrounding environment and/or the structure(s) in which the piezo is mounted, a given mounted piezoelectric ceramic may have one or more harmonic frequencies. Increasing the contact of the Ultrasonic Energy Window 207 to the tissues, possibly by pressing on the TD, may reduce intervening tissue fluids and/or water between the Ultrasonic Energy Window and the target tissues and thus increase coupling between the energy window and the target tissue which may increase the efficiency of ultrasonic energy delivery. In some implementations, ultrasonic energy window 207 may be used to heat and/or treat and/or damage target tissues by applying an ultrasonic frequency range such as a frequency range in excess of 40 kiloHertz. In some implementations, window 307 may be used to heat and/or treat and/or damage target tissues by applying an energy level with energy parameters that may range to about 10-20 Watts and/or 30-50 Volts.

In some embodiments, an ultrasonic energy window may be provided that is configured to allow for selective adjustment of one or more such parameters, including power, voltage, and/or frequency, as described above.

Examples of ultrasound technology that may be useful for some of the embodiments disclosed herein such as for ultrasonic energy windows 207 and/or 208 may be found in miniaturized Ultrasound Arrays for Interstitial Ablation and Imaging (Makin, Mast, Faidi, et al.; Ultrasound Med Biol 2005; 31(11):1539-50.) and/or Design and Preliminary Results of an Ultrasound Applicator for Interstitial Thermal Coagulation (Lafon, Chapelon, Prat, et al.; Ultrasound Med Biol 1998; 24(1):113-22.) and/or Optimizing the Shape of Ultrasound Transducers for Interstitial Thermal Ablation (Lafon, Theillere, et al.; Med Phys 2002; 29(3):290-7.) and/or Rapid Skin Permeablization by the Simultaneous Application of Dual Frequency, High-Intensity Ultrasound (Schoelhammer, Polat, Mendenhall, Langer, et al; Journal of Controlled Release, 2012, 163(2):154-160.) and/or Interstitial Ddevices for Minimally Invasive Thermal Ablation by High Intensity Ultrasound (Lafon, Melodelima, Salomir, Chaelon; Int J. Hyperther 2007; 23(2):153-63.) and/or Theoretical Comparison of Two Interstitial Ultrasound Applicators Designed to Induce Cylindrical Zones of Tissue Ablation (Lafon, Chavrier, Prat, et al.; Med Biol Eng Comput 1999; 37(3):298-303.) and/or Feasibility of Linear Arrays for Interstitial Ultrasound Thermal Therapy (Chopra, Bronskill, Foster; Med Phys 2000; 27(6):1281-6.) and/or Development of an Interstitial Ultrasound Applicator for Endoscopic Procedures: Animal Experimentation (Lafon, Theillere, Prat, et al.; Ultrasound Med Biol 2000; 26(4):669-75.) and/or Multisectored Interstitial Ultrasound Applicators for Dynamic Angular Control of Thermal Therapy (Kinsey, Diederich, Tyreus, et al.; Med Phys 2006; 33(5):1352-63.) and/or Evaluation of Multielement catheter-cooled interstitial ultrasound applicators for high-temperature thermal therapy (Nau, Diederich, Burdette; Med Phys 2001; 28(7):1525-34.) and/or Feasibility of Ultrasound Hyperthermia with Waveguide Interstitial Applicator (Jarosz; IEEE Trans Biomed Eng 1996; 43(11): 1106-15.) and/or Transurethral Ultrasound Array for Prostate Thermal Therapy: Initial Studies (Diederich, Burdette; IEEE Trans Ultrason Ferroelectr Freq Control 1996; 43(6):1011-22.) which are hereby incorporated by reference in its entirety.

Electro-cutting and electro-coagulation currents may be controlled outside the TDM at an electrosurgical generator, such as the Bovie Aaron 1250™ or Bovie Icon GP™. In some embodiments, the tip may measure about 1 cm in width and about 1-2 mm in thickness. Sizes of about one-fifth to about five times these dimensions may also have possible uses. In some veterinary embodiments, tip sizes of about one-tenth to 20 times the aforementioned dimensions may also have possible uses. In some embodiments, the tip can be a separate piece that may be secured to a shaft by a variety of methods, such as a snap mechanism, mating grooves, plastic sonic welding, etc. Alternatively, in some other embodiments, the tip can be integral or a continuation of a shaft made of similar metal(s) or material(s). In some embodiments, the tip may also be constructed of materials that are both electrically non-conductive and of low thermal conductivity; such materials might comprise, for example, porcelain, ceramics, glass-ceramics, plastics, varieties of polytetrafluoroethylene, carbon, graphite, and graphite-fiberglass composites.

In some embodiments, the tip may be constructed of a support matrix of an insulating material (e.g., ceramic or glass material such as alumina, zirconia). Conduits 211 and/or 212 may connect to electrically conductive elements to bring RF electrosurgical energy from an electrosurgical generator down the shaft 202 to electrically conductive lysing elements 205 mounted in the recessions in between protrusions 204. In some embodiments, the protrusions may comprise bulbous protrusions. The tip shown in this embodiment has four relative protrusions and three relative recessions and provides for a monopolar tip conductive element. All of the axes of the relative protrusions of the tip depicted in this embodiment extend at least substantially parallel to the axis of the shaft of the TDM (as viewed from Top). In embodiments of tips of such axial placement of protrusions and or relative recessions, surgeons may use methods of defining and or dissecting a target area by entering through an incision and then moving the TDM tip in a primarily axial direction forward and backward and reorienting the TDM after the backstroke in a spokewheel pattern the TDM to access tissues adjacent to earlier strokes. In the depicted embodiment, the tip 201 may alternatively be made partially or completely of concentrically laminated or annealed-in wafer layers of materials that may include plastics, silicon, glass, glass/ceramics or ceramics. Lysing elements 205 may also be made partially or completely of a cermet material. Alternatively, in a further embodiment, the tip may be constructed of insulation covered metals or electroconductive materials. In some embodiments, the shaft may be flat, rectangular, or geometric in cross-section, or may be substantially flattened. In some embodiments, smoothing of the edges of the shaft may reduce friction on the tissues surrounding the entrance wound. In some further embodiments, the shaft may be made of metal or plastic or other material with a completely occupied or hollow interior that can contain insulated wires, electrical conductors, fluid/gas pumping or suctioning conduits, fiber-optics, or insulation.

In some embodiments, shaft plastics, such as polytetrafluoroethylene, may act as insulation about wire or electrically conductive elements. In some embodiments, the shaft may alternatively be made partially or completely of concentrically laminated or annealed-in wafer layers of materials that may include plastics, silicon, glass, glass/ceramics, ceramics carbon, graphite, and/or graphite-fiberglass composites. Depending upon the intended uses for the device, an electrically conductive element internal to the shaft may be provided to conduct electrical impulses or RF signals from an external power/control unit (such as a Valleylab™ electrosurgical generator) to another energy window 208. In some embodiments, energy windows 207 and/or 208 may only be substantially planar, or may take on other cross-sectional shapes that may correspond with a portion of the shape of the shaft, such as arced, stair-step, or other geometric shapes/curvatures. In some embodiments, energy window 208 may comprise another ultrasonic energy window. In the embodiments depicted in FIGS. 2a & 2b, energy window 207 is adjacent to protrusions 204, however other embodiments are contemplated in which an energy window may be positioned elsewhere on the shaft 202 or tip 201 of the wand, and still be considered adjacent to protrusions 204. For example, in an embodiment lacking energy window 207, but still comprising energy window 208, energy window 208 would still be considered adjacent to protrusion 204. However, if an energy window was placed on handle 203, such an energy window would not be considered adjacent to protrusions 204.

The conduit(s) may also contain electrical control wires to aid in device operation. Partially hidden from direct view in FIGS. 2a & 2b, and located in the recessions defined by protrusions 204, are electrically conductive tissue lysing elements 205, which, when powered by an electrosurgical generator, effects lysing of tissue planes on forward motion of the device. The lysing segments may be located at the termini of conductive elements. In some embodiments, one or more sensors such as for example sensors 210 and 214 may be positioned on the device. The sensors 210 and 214 may comprise any of the sensors described in the specification herein. Other embodiments may comprise one or more sensors on any other suitable location on the TDM, including but not limited to on the protrusions or otherwise on the tip, and on the shaft. Sensors that may be useful include thermal sensors, photoelectric or photo optic sensors, cameras, etc. In some embodiments, one or more sensors may be used to monitor the local post passage electrical impedance or thermal conditions that may exist near the distal tip of the shaft or on the tip. Some embodiments may also comprise one or more sensors incorporating MEMS (Micro Electro-Mechanical Systems) technology, such as MEMS gyroscopes, accelerometers, and the like. Such sensors may be positioned at any number of locations on the TDM, including within the handle in some embodiments. In some embodiments, sensor 214 may comprise fiberoptic elements. In an embodiment, the sensor can be configured to sense a temperature of tissue adjacent to the apparatus. The temperature sensor may alternatively be configured or sense a temperature of one or more fluids adjacent to the apparatus such as for example tissue fluids and/or fluids introduced by the surgeon.

Temperature and impedance values may be tracked on a display screen or directly linked to a microprocessor capable of signaling control electronics to alter the energy delivered to the tip when preset values are approached or exceeded. Typical instrumentation paths are widely known, such as thermal sensing thermistors, and may feed to analog amplifiers which, in turn, feed analog digital converters leading to a microprocessor. In some embodiments, internal or external ultrasound measurements may also provide information which may be incorporated into a feedback circuit. In an embodiment, an optional mid and low frequency ultrasound transducer may also be activated to transmit energy to the tip and provide additional heating and may additionally improve lysing. In some embodiments, a flashing visible light source, for example, an LED, can be mounted on the tip may show through the tissues and/or organs to identify the location of the device.

In some embodiments, one or more electromagnetic delivery elements 215 may be positioned on tip or shaft. Other embodiments may comprise one or more electromagnetic delivery elements on any other suitable location on the TDM, including but not limited to on the protrusions or otherwise on the tip, and on the shaft. Electromagnetic delivery elements that may be useful include: LEDs, LASERs, fiberoptics, filaments, photoelectric materials, infrared emitters, etc.

Figure 2B:
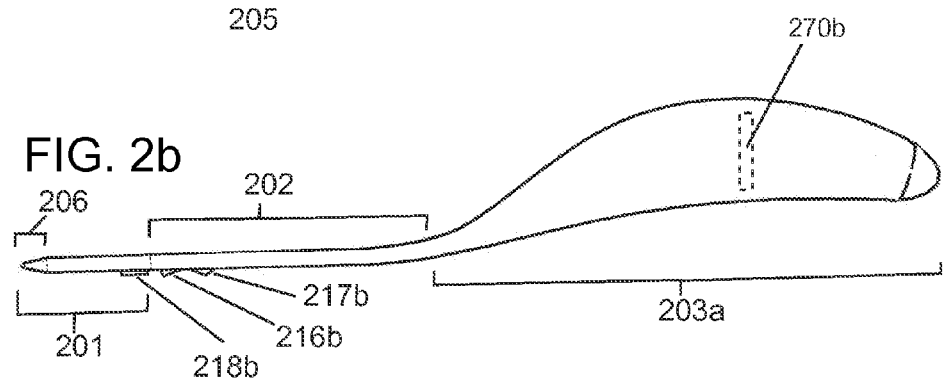

FIG. 2b is a side elevation view of the embodiment previously depicted in FIG. 2a. In the depicted embodiment, tip 201 which terminates in protrusions 206 may be made of materials that are both electrically non-conductive and of low thermal conductivity such as porcelain, epoxies, ceramics, glass-ceramics, plastics, or varieties of polytetrafluoroethylene. Alternatively, the tip may be made from metals or electroconductive materials that are completely or partially insulated. Note the relative protrusions and relative recessions are not completely visible from this viewing angle. The tip shown in this embodiment has four relative protrusions and three relative recessions and provides for a monopolar tip conductive element. In some embodiments, the electrically conductive tissue lysing element(s) 205 (usually hidden from view at most angles), which may have any geometric shape including a thin cylindrical wire, may be positioned within the relative recessions of the tip. The electrically conductive lysing element can be in the shape of a plate or plane or wire and made of any metal or alloy that does not melt under operating conditions or give off toxic residua. Optimal materials may include but are not limited to steel, nickel, alloys, palladium, gold, tungsten, silver, copper, and platinum. Metals may become oxidized thus impeding electrical flow and function. In some further adjustable embodiments, locations of the electrically conductive lysing elements with respect to the protrusions may be adjusted by MEMS or microelectronics.

Figure 6A:
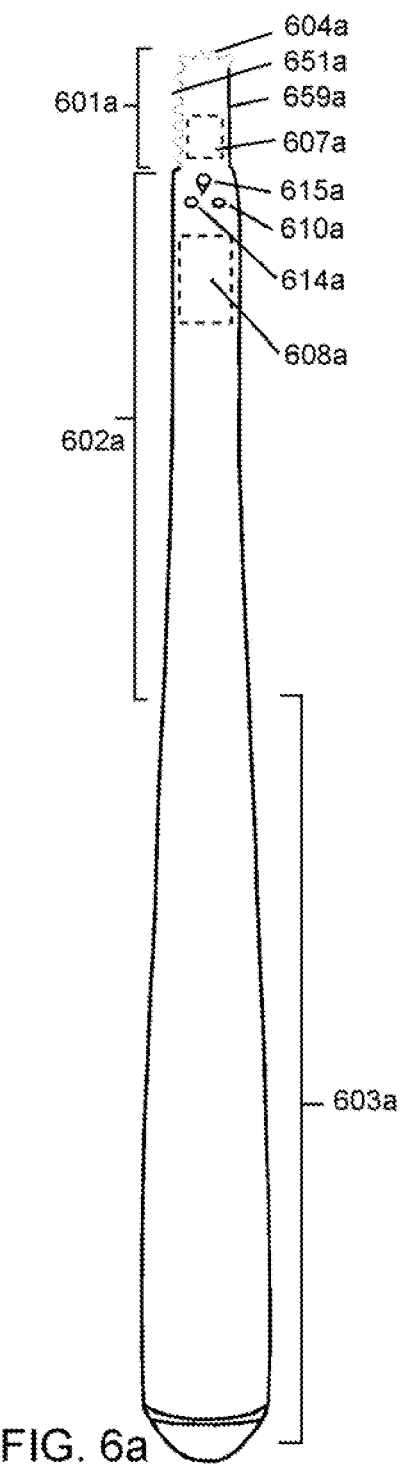
FIG. 6a is an upper plan view illustrating an embodiment of a tissue dissector and modifier with an asymmetrical tip area, wherein some of the protrusions and lysing segments are oriented in a non-axial direction and the non-axial protrusions do not extend beyond the width of the distal shaft.

In alternative embodiments the geometry of the tip area may comprise protrusions that are not oriented along the axis of the shaft (as seen from a top view); some of these alternative embodiments for tip area geometries are depicted in FIGS. 5a,b,c,d,e,f,g,h and FIGS. 6a,b,c,d. Some embodiments may be configured to be modular and/or comprise disposable tips such that a surgeon can place an appropriate tip for a particular surgery on the shaft. Alternatively or additionally one or more of the tips may be disposable such that a surgeon may dispose of the tip after performing surgery and install a new tip for subsequent surgeries or a continuation of the current surgery with a new tip.

In some embodiments, one or more suction/vacuum ports 217b may be provided on or about the tip or distal shaft. The port(s) may be fluidly coupled with a vacuum; the vacuum may comprise a pump or a negative pressure chamber or a syringe at the end of a fluid conduit. Other embodiments may comprise one or more suction/vacuum ports on any other suitable location on the TDM, including but not limited to on the protrusions or otherwise on the tip, and on the shaft. In some embodiments, a fluid delivery port 216b may be provided. In some embodiments the fluid delivery port may be coupled with a pump or high pressure fluid. In some embodiments the port may be perpetually open such that fluid may be delivered therethrough upon actuation of a pump or fluid pressure system. In other embodiments the port may be closed and selectively opened to deliver fluid therethrough. Other embodiments may comprise one or more fluid ports on any other suitable location on the TDM, including but not limited to on the protrusions or otherwise on the tip, and on the shaft. Fluid ports that may be useful may comprise channels within the TDM, polymer lines, hoses, etc. Fluids that may emanate from the outlet may comprise ionic fluids such as saline, medicines (including but not limited to antibiotics, anesthetics, antineoplastic agents, bacteriostatic agents, etc.), non-ionic fluids, and or gasses (including but not limited to nitrogen, argon, air, etc.). In some embodiments fluids may be under higher pressures or sprayed. It should be understood that although these elements (216b & 217b) are not depicted in every one of the other figures, any of the embodiments described herein may include one or more such elements.

In some embodiments, a vibration means 270b may be positioned in the handle. Other embodiments may comprise one or more vibration means on any other suitable location on the TDM, including but not limited to on the protrusions or otherwise on the tip, and on the shaft. Examples of suitable vibration means may include piezoelectric materials, ultrasonic motors with stators, piezoelectric actuators, vibration motor such as an off-center weight mounted on a gear, etc. Some vibration means may be configured to emit ultrasound in the 20-40 kHz range. Yet other vibration means may include electromagnet drivers with a frequency of operation in the range of 150-400 Hz. In some embodiments, one or more vibration means may be used to provide additional forces which may facilitate passage of the TDM. In some embodiments, one or more vibration means may be used to reduce debris on the electrosurgical or other components of the TDM. In a further embodiment, a vibration means may be directly or indirectly connected to one or more of the lysing segments.

In the depicted embodiment, 218b represents an antenna, such as an RFID TAG or Bluetooth antenna. In embodiments in which antenna 218b comprises an RFID tag, the RFID tag may comprise an RFID transponder. In other embodiments the RFID tag may comprise a passive tag. It should be understood that antenna 218b is not depicted in every one of the other figures, any of the embodiments described herein may comprise one or more such elements. Other embodiments may comprise one or more antennas on any other suitable location on the TDM, including but not limited to on the protrusions or otherwise on the tip, and on the shaft. In some embodiments an RFID transponder or another antenna may comprise a microchip, such as a microchip having a rewritable memory. In some embodiments, the tag may measure less than a few millimeters. In some embodiments a reader may generate an alternating electromagnetic field which activates the antenna/RFID transponder and data may be sent via frequency modulation. In an embodiment, the position of the RFID tag or other antenna may be determined by an alternating electromagnetic field in the ultra-high frequency range. The position may be related to a 3 dimensional mapping of the subject. In an embodiment the reader may generate an alternating electromagnetic field. In some such embodiments, the alternating electromagnetic field may be in the shortwave (13.56 MHz) or UHF (865-869 MHz) frequency.

In some embodiments tip 201 may be attached to a robotic arm. In some embodiments, tip 201 and portion of shaft 202 may be attached to a robotic arm. In some embodiments tip 201 and/or a portion of shaft 202 and/or a portion shaft and/or portion of handle 203 may be attached to a robotic arm. In some embodiments, the robotic arm may comprise one or more motors such as a screw-drive motor, gear motor, hydraulic motors, etc. In some embodiments the robotic arm system may comprise worm gearheads, video cameras, motor control circuits, monitors, remote control devices, illumination sources, tactile interface, etc.

FIG. 3a is a perspective view of an embodiment of a tissue dissector and modifier with a target-tissue-impedance-matched-microwave-based energy window on the upper side of the device. A target-tissue-impedance-matched-microwave emission system (TTIMMES) may be advantageous over previously available microwave based medical treatment systems because it is difficult to model tissue against water because the dielectric associated with water differs from that of blood, which differs from that of tissue, and so on, especially after coagulum formation. Both non-impedance-matched-microwave and radiofrequency treatments may suffer from this concern. Beneficially for microwaves there is limited coagulum formation, and deeper penetration of energy into the tissues. With impedance matching, energy is not reflected back from the tissues into the microwave emitting antennae as the energy proceeds uni-directionally through the coaxial cable and into the target tissue. A controllable solid state source (e.g., MicroBlate™) of a super-high frequency (SHF) microwave emission band of 14.5 GHz system that is impedance matched has been shown to produce a depth of penetration of about 1.6 mm using coaxial antennae measuring just 2.2 mm (*Int'l Journal of Hyperthermia* 28: 43-54, 2012).

FIG. 3a is a perspective view of an embodiment of a TDM with an alternative energy window 307 on the upper side of the device configured to hold an array of impedance-matched-microwave emitting antennae. It should be noted that the term "energy window" is intended to encompass what is referred to as a planar-tissue-altering-window/zone in U.S. Pat. No. 7,494,488 and, as described herein, need not contain a microwave emitter in all embodiments. Additionally, the "energy window" may comprise a variety of other energy emitting devices, including radiofrequency, intense pulsed light, LASER, thermal, and ultrasonic. It should also be understood that the term "energy window" does not necessarily imply that energy is delivered uniformly throughout the region comprising the energy window. Instead, some energy window implementations may comprise a series of termini or other regions within which energy is delivered with interspersed regions within which no energy, or less energy, is delivered. This configuration may be useful for some implementations to allow for alteration of certain tissue areas with interspersed areas within which tissue is not altered, or at least is less altered. This may have some advantages for certain applications due to the way in which such tissue heals. It is contemplated that in alternative embodiments, impedance-matched-microwave energy window 307 may be omitted.

FIG. 3a is a perspective view of an embodiment of a TDM comprising a tip 301, a shaft 302 and a handle 303. Electrosurgical energy may be delivered in conduits 311 and/or 312, whereas gigahertz microwave energy may be delivered by coaxial cable bundle 322 through the handle and shaft to energy window 307, which may comprise four antennae termini. Some embodiments comprise between 1 and 10 antennae. Some embodiments may comprise a flat microwave emitting device. A second energy window 308 may also be included in some embodiments, and may comprise yet another microwave emitter or another variety of energy emitting device. Electro-cutting and electro-coagulation currents may be controlled outside the TDM at an electrosurgical generator, such as the Bovie Aaron 1250™ or Bovie Icon GP™. In some embodiments, the tip may measure about 1 cm in width and about 1-2 mm in thickness. Sizes of about one-fifth to about five times these dimensions may also have possible uses. In some veterinary embodiments, tip sizes of about one-tenth to 20 times the aforementioned dimensions may also have possible uses.

In some embodiments, the tip can be a separate piece that may be secured to a shaft by a variety of methods, such as a snap mechanism, mating grooves, plastic sonic welding, etc. Alternatively, in some other embodiments, the tip can be integral or a continuation of a shaft made of similar metal(s) or material(s). In some embodiments, the tip may also be constructed of materials that are both electrically non-conductive and of low thermal conductivity; such materials might comprise, for example, porcelain, ceramics, glass-ceramics, plastics, varieties of polytetrafluoroethylene, carbon, graphite, and graphite-fiberglass composites.

In some embodiments, the tip may be constructed of a support matrix of an insulating material (e.g., ceramic or glass material such as alumina, zirconia). Conduit 311 may connect to electrically conductive elements to bring RF electrosurgical energy from an electrosurgical generator down the shaft 302 to electrically conductive lysing elements 305 mounted in the recessions in between protrusions 304. In some embodiments, the protrusions may comprise bulbous protrusions. In the depicted embodiment, the tip 301 may alternatively be made partially or completely of concentrically laminated or annealed-in wafer layers of materials that may include plastics, silicon, glass, glass/ceramics or ceramics. Alternatively, in a further embodiment, the tip may be constructed of insulation covered metals or electroconductive materials. In some embodiments, the shaft may be flat, rectangular, or geometric in cross-section, or may be substantially flattened. In some embodiments, smoothing of the edges of the shaft may reduce friction on the tissues surrounding the entrance wound. In some further embodiments, the shaft may be made of metal or plastic or other material with a completely occupied or hollow interior that can contain insulated wires, electrical conductors, fluid/gas pumping or suctioning conduits, fiber-optics, or insulation.

In some embodiments, shaft plastics, such as polytetrafluoroethylene may act as insulation about wire or electrically conductive elements. In some embodiments, the shaft may alternatively be made partially or completely of concentrically laminated or annealed-in wafer layers of materials that may include plastics, silicon, glass, glass/ceramics, ceramics carbon, graphite, graphite-fiberglass composites. Depending upon the intended uses for the device, an electrically conductive element internal to shaft may be provided to conduct electrical impulses or RF signals from an external power/control unit (such as a Valleylab™ electrosurgical generator) to another energy window 308. In some embodiments, energy windows 307 and/or 308 may only be substantially planar, or may take on other cross-sectional shapes that may correspond with a portion of the shape of the shaft, such as arced, stairstep, or other geometric shapes/curvatures. In some embodiments, energy window 308 may comprise another microwave emitter. In the embodiments depicted in FIGS. 3a & 3b, energy window 307 is adjacent to protrusions 304, however other embodiments are contemplated in which an energy window may be positioned elsewhere on the shaft 302 or tip 301 of the wand, and still be considered adjacent to protrusions 304. For example, in an embodiment lacking energy window 307, but still comprising energy window 308, energy window 308 would still be considered adjacent to protrusion 304. However, if an energy window was placed on handle 303, such an energy window would not be considered adjacent to the protrusions 304.

The conduit(s) may also contain electrical control wires to aid in device operation. Partially hidden from direct view in FIGS. 3a & 3b, and located in the recessions defined by protrusions 304, are electrically conductive tissue lysing elements 305, which, when powered by an electrosurgical generator, effects lysing of tissue planes on forward motion of the device. The lysing segments may be located at the termini of conductive elements.

In some embodiments, one or more sensors such as for example sensors 310 and 314 may be positioned on the device. The sensors 310 and 314 may comprise any of the sensors described in the specification herein. Other embodiments may comprise one or more sensors on any other suitable location on the TDM, including but not limited to on the protrusions or otherwise on the tip, and on the shaft. Sensors that may be useful include thermal sensors, photoelectric or photo optic sensors, cameras, etc. In some embodiments, one or more sensors may be used to monitor the local post passage electrical impedance or thermal conditions that may exist near the distal tip of the shaft or on the tip. Some embodiments may also comprise one or more sensors incorporating MEMS (Micro Electro-Mechanical Systems) technology, such as MEMS gyroscopes, accelerometers, and the like. Such sensors may be positioned at any number of locations on the TDM, including within the handle in some embodiments. In some embodiments, sensor 314 may comprise fiberoptic elements. In an embodiment, the sensor can be configured to sense a temperature of tissue adjacent to the apparatus during one or methods described herein. The temperature sensor may alternatively be configured or sense a temperature of one or more fluids adjacent to the apparatus such as for example tissue fluids and/or fluids introduced by the surgeon.

Temperature and impedance values may be tracked on a display screen or directly linked to a microprocessor capable of signaling control electronics to alter the energy delivered to the tip when preset values are approached or exceeded. Typical instrumentation paths are widely known, such as thermal sensing thermistors, and may feed to analog amplifiers which, in turn, feed analog digital converters leading to a microprocessor. In some embodiments, internal or external ultrasound measurements may also provide information which may be incorporated into a feedback circuit. In an embodiment, an optional mid and low frequency ultrasound transducer may also be activated to transmit energy to the tip and provide additional heating and may additionally improve lysing. In some embodiments, a flashing visible light source, for example, an LED, can be mounted on the tip may show through the tissues and/or organs to identify the location of the device.

In some embodiments, one or more electromagnetic delivery elements 315 may be positioned on tip or shaft. Other embodiments may comprise one or more electromagnetic delivery elements on any other suitable location on the TDM, including but not limited to on the protrusions or otherwise on the tip, and on the shaft. Electromagnetic delivery elements that may be useful include: LEDs, LASERs, fiberoptics, filaments, photoelectric materials, infrared emitters, etc.

Alternatively, in some embodiments, since cutting or electrical current may cause an effect at a distance without direct contact, the lysing element may be recessed into the relative recessions or grooves defined by the protrusions 304 or, alternatively, may be flush with protrusions 304. In some further adjustable embodiments, locations of the electrically conductive lysing elements with respect to the protrusions may be adjusted by diminutive screws or ratchets. In some further adjustable embodiments, locations of the electrically conductive lysing elements with respect to the protrusions may be adjusted by MEMS or microelectronics.

In some embodiments, the electrically conductive lysing element may also exist in the shape of a simple wire of 0.1 mm and 1 mm 0.01 mm to 3 mm. In some embodiments, the wire may measure between 0.01 mm to 3 mm. Such a wire may be singly or doubly insulated as was described for the plate and may have the same electrical continuities as was discussed for the planar (plate) version. In some embodiments, an electrosurgical current for the electrically conductive lysing element is of the monopolar "cutting" variety and setting and may be delivered to the tip lysing conductor in a continuous fashion or, alternatively, a pulsed fashion. The surgeon can control the presence of current by a foot pedal control of the electrosurgical generator or by button control on the shaft (forward facing button). The amount of cutting current may be modified by standard interfaces or dials on the electrosurgical generator. In some embodiments, the electrosurgically energized tip current can be further pulsed at varying rates, by interpolating gating circuitry at some point external to the electrosurgical generator by standard mechanisms known in the art, that may range from about 1 per second to about 60 per second. In some embodiments, the rate may vary from about 1 per second to about 150 per second. In some embodiments, the electrosurgically energized tip current can be further pulsed at varying rates by gating circuitry within the electrosurgical generator by standard mechanisms known in the art.

In alternative embodiments the geometry of the tip area may comprise protrusions that are not oriented along the axis of the shaft (as seen from a top view); some of these alternative embodiments for tip area geometries are depicted in FIGS. 5a,b,c,d,e,f,g,h and FIGS. 6a,b,c,d. Some embodiments may be configured to be modular and/or comprise disposable tips such that a surgeon can place an appropriate tip for a particular surgery on the shaft. Alternatively or additionally one or more of the tips may be disposable such that a surgeon may dispose of the tip after performing surgery and install a new tip for subsequent surgeries or a continuation of the current surgery with a new tip.

In some embodiments, one or more suction/vacuum ports 317b may be provided on or about the tip or distal shaft. The port(s) may be fluidly coupled with a vacuum; the vacuum may comprise a pump or a negative pressure chamber or a syringe at the end of a fluid conduit. Other embodiments may comprise one or more suction/vacuum ports on any other suitable location on the TDM, including but not limited to on the protrusions or otherwise on the tip, and on the shaft. In some embodiments, a fluid delivery port 316b may be provided. In some embodiments the fluid delivery port may be coupled with a pump or high pressure fluid. In some embodiments the port may be perpetually open such that fluid may be delivered therethrough upon actuation of a pump or fluid pressure system. In other embodiments the port may be closed and selectively opened to deliver fluid therethrough. Other embodiments may comprise one or more fluid ports on any other suitable location on the TDM, including but not limited to on the protrusions or otherwise on the tip, and on the shaft. Fluid ports that may be useful may comprise channels within the TDM, polymer lines, hoses, etc. Fluids that may emanate from the outlet may comprise ionic fluids such as saline, medicines (including but not limited to antibiotics, anesthetics, antineoplastic agents, bacteriostatic agents, etc.), non-ionic fluids, and or gasses (including but not limited to nitrogen, argon, air, etc.). In some embodiments fluids may be under higher pressures or sprayed. It should be understood that although these elements (316b & 317b) are not depicted in every one of the other figures, any of the embodiments described herein may include one or more such elements.

In some embodiments, a vibration means 370b may be positioned in the handle. Other embodiments may comprise one or more vibration means on any other suitable location on the TDM, including but not limited to on the protrusions or otherwise on the tip, and on the shaft. Examples of suitable vibration means may include piezoelectric materials, ultrasonic motors with stators, piezoelectric actuators, vibration motor such as an off-center weight mounted on a gear, etc. Some vibration means may be configured to emit ultrasound in the 20-40 kHz range. Yet other vibration means may include electromagnet drivers with a frequency of operation in the range of 150-400 Hz. In some embodiments, one or more vibration means may be used to provide additional forces which may facilitate passage of the TDM. In some embodiments, one or more vibration means may be used to reduce debris on the electrosurgical or other components of the TDM. In a further embodiment, a vibration means may be directly or indirectly connected to one or more of the lysing segments.

In the depicted embodiment, 318b represents an antenna, such as an RFID TAG. In embodiments in which antenna 318b comprises an RFID tag, the RFID tag may comprise an RFID transponder. In other embodiments the RFID tag may comprise a passive tag. It should be understood that antenna 318b is not depicted in every one of the other figures, any of the embodiments described herein may comprise one or more such elements. Other embodiments may comprise one or more antennas on any other suitable location on the TDM, including but not limited to on the protrusions or otherwise on the tip, and on the shaft. In some embodiments an RFID transponder or another antenna may comprise a microchip, such as a microchip having a rewritable memory. In some embodiments, the tag may measure less than a few millimeters. In some embodiments a reader may generate an alternating electromagnetic field which activates the RFID transponder/antenna and data may be sent via frequency modulation. In an embodiment, the position of the RFID tag/antenna may be determined by an alternating electromagnetic field in the ultra-high frequency range. The position may be related to a 3 dimensional mapping of the subject. In an embodiment the reader may generate an alternating electromagnetic field. In some such embodiments, the alternating electromagnetic field may be in the shortwave (13.56 MHz) or UHF (865-869 MHz) frequency.

In some embodiments tip 301 may be attached to a robotic arm. In some embodiments, tip 301 and portion of shaft 302 may be attached to a robotic arm. In some embodiments tip 301 and/or a portion of shaft 302 and/or a portion shaft and/or portion of handle 303 may be attached to a robotic arm. In some embodiments, the robotic arm may comprise one or more motors such as a screw-drive motor, gear motor, hydraulic motors, etc. In some embodiments the robotic arm system may comprise worm gearheads, video cameras, motor control circuits, monitors, remote control devices, illumination sources, tactile interface, etc.

FIG. 3c depicts an embodiment of the target-tissue-impedance-matched-microwave-based emission system (TTIMMES) previously depicted in FIG. 3a. This depicted embodiment includes energy window 307, which is configured to comprise a bundle of microwave antennae 322a further comprising singular antennae, such as 320 and 321. Coaxial cable bundle 322 carries gigahertz microwave energy derived from a super high frequency (SHF) generator, into and through the handle, down the shaft and into the coaxial antennae. In some embodiments, a flat microwave emitter may be placed in energy window 307. In some embodiments, flat microwave emission devices are comprised of a "microstrip" in which an antenna is printed on a circuitboard. In some embodiments, the circuitboard may be coated with polytetrafluoroethylene, and may be seated on an alumina substrate.

In some embodiments, a controllable solid state source (N5183A MXG Microwave Analog Signal Generator from Agilent Technologies™) of a super-high frequency (SHF) microwave emission band of 36 GHz system that is impedance matched drives the coaxial cables to emit microwaves.

Additionally, an "energy window" may comprise a variety of other energy emitting devices, including radiofrequency, microwave, filament, light, intense pulsed light, LASER, thermal, and ultrasonic. A second energy window 308 may also be included in some embodiments, and may comprise yet another microwave or another variety of energy emitting device.

Some embodiments of the energy window may also comprise one or more LASERs that may also be used through the fiberoptic and may be controlled at the electromagnetic energy source by a footswitch. In some embodiments, the planar tissue-altering-window/zone may be an optical window that allows laser light to exit the shaft and irradiate nearby target tissue. In some embodiments, a light delivery means, which can be a hollow waveguide or single or multiple optical fibers (such as metal coated plastic manufactured by Polymicro Technologies™ Inc. of Phoenix, Ariz.) may be contained in an external conduit. The external conduit may comprise, for example an articulating arm as is commonly used in surgical laser systems. Additional control wires and power may be delivered to the handpiece via the external conduit. However, using foot-pedal control from an electromagnetic energy radiation source or control interface, dial, or panel will likely be less cumbersome for the surgeon and reduce the expense of handpiece finger-control manufacture.

Some embodiments may use an energy window comprising Germanium, which may allow for egress of laser light and collection of data by thermal sensors, and such energy window may be of varying size. In another embodiment, a multiplicity of optical fibers may terminate at specific or random places within the energy window. Such bare or coated fiberoptic termini may protrude from, be flush with, or be recessed into, other materials comprising the energy window. Such bare or coated fiberoptic termini may protrude from, be flush with or be recessed into other materials comprising the energy window. In some embodiments, bare fiberoptics comprising ethylene oxide sterilizable may be seated in a thermally nonconductive background, preferably at uniform 90 degree angles, but variable angles between 0 and 180 degrees may also be efficacious. The preferred light delivery means may depend on the wavelength of the laser used. Infrared light emitted by the heated tissue can also be collected through the window and sensed by an infrared detector to measure the tissue temperature. For $CO_2$ laser irradiance, reliable sources include standard operating room units, such as the Encore Ultrapulse® from Lumenis Corp. of Santa Clara, Calif., which is capable of providing continuous $CO_2$ laser energy outputs of 2-22 mJoules at 1-60 Watts. Older models of the Coherent Ultrapulse™ may also be suitable (Coherent™ now owned by Lumenis™).

In some embodiments, a hollow section of shaft may act as a waveguide or may contain a metal-coated plastic fiberoptic or waveguide to allow laser light to pass through and exit from window near tip. The window may allow egress for laser light delivered to apparatus. In some embodiments, Lasers may include both pulsed and continuous wave lasers, such as $CO_2$, erbium YAG, Nd:YAG and Yf:YAG. The beam diameter may be changed as desired, as those skilled in the art will appreciate. However, this list is not intended to be self-limiting and other wavelength lasers may be used.

Some embodiments of the energy window may comprise an intense, pulsed, non-coherent, non-LASER, such as a filtered flashlamp that emits a broadband of visible light. The flashlamp, such as a smaller version of that used by ESC/Sharplan™, Norwood, Mass. (500-1200 nm emission range; 50 J/sqcm fluence; 4 ms pulse; 550 nm filter) may occupy the handle or window/zone of the embodiment. In some embodiments, a flashlamp may emit optical and thermal radiation that can directly exit the energy window, or may be reflected off a reflector to exit through the window. In an embodiment, a reflector may have a parabolic shape to effectively collect radiation emitted away from the window, which may be made of a wide variety of glass that transmits optical, near infrared, and infrared light (e.g., quartz, fused silica and germanium.) Emission spectra may be filtered to achieve the desired effects. Thermal emissions or visible radiation absorption may locally heat the dermis to alter collagen. Thermal sensors may also be used to control or reduce overheating. In order to eliminate excessive heating of the shaft and the surrounding facial tissue, the flashlamp and reflector may be thermally isolated by low thermal conductivity materials or cold nitrogen gas that may be pumped through a hollow or recessed portion of the shaft and/or handle. In an embodiment, the handle can be an alternative location for the flashlamp so that emitted radiation may be reflected by a mirror through the window/zone.

In some embodiments, direct piezoelectric versions of the energy window may impart vibrational energy to water molecules contained in target tissues passing adjacent to the piezo material(s). Temperature elevations may cause collagenous change and cell wall damage, however, ultrasonic energy application may have disruptive effects at the subcellular level as well. Energy output for piezoelectric window/zones may typically range from about 1-30 J; in an embodiment, an energy output range of about 1-6 J may occur in a surgical device moving about 1 cm/second. In an embodiment, temperature and impedance sensors may provide intraoperative real-time data can modulate energy input into the piezoelectric, which may be energized by one or more conductive elements in the shaft in further connection with the control unit and/or power supply. In some embodiments, the energy window for a thermally energized embodiment may allow thermal energy to escape from within the shaft, and wherein the tip can be integral or a continuation of shaft made of similar metal or materials. The tip may also be constructed of materials that are both electrically non-conductive and of low thermal conductivity; such materials might be porcelain, ceramics or plastics. Portions of the tip and shaft may be covered with Teflon® to facilitate smooth movement.

Teflon® may also be used to coat portions of an antenna, such as a microwave antenna, such that the energy is delivered in a more uniform fashion.

In some embodiments, a filament may be fixedly attached to the shaft. The hot filament may emit optical and thermal radiation that can directly exit the energy window or be reflected off a reflector to also exit through window. The reflector may have a parabolic shape to effectively collect all optical and thermal radiation emitted away from the window. In some embodiments, a hot filament can be a tungsten carbide filament similar to those used in high power light bulbs. The wavelength may be adjusted and controlled by adjusting the filament temperature/current. In some embodiments, the window may be selected from a wide variety of glass that transmits optical, near infrared and infrared light (e.g., quartz, fused silica and germanium.) The tissue penetration depth may depend on the wavelength of the light (e.g., 1 μm may penetrate through about 10 mm, 10 μm may penetrate through about 0.02 mm). In an embodiment, the broad emission spectrum from the hot filament may be filtered to achieve the desired tissue effect. In some embodiments, thermal sensors connected to the control unit by electrical wire may be used to monitor the temperature of tissue that is in contact with the shaft. In order to eliminate excessive heating of the shaft and the surrounding facial tissue, the heating element and/or reflector may be thermally isolated by low thermal conductivity materials. The heating element may be isolated by reducing contact with the shaft, whereas the reflector may have an isolating layer where it attaches to the shaft. In an embodiment, cold nitrogen gas may be injected through tube and pumped out through the hollow shaft to cool the tip and shaft.

In some embodiments, the hot filament may be placed in the handle while emitted optical and thermal radiation is reflected off a mirror through the window. An alternative embodiment may allow for tissue heating to be achieved by direct contact with a hot surface where electric current flowing through wires heats a resistive load made of single or multiple elements to a user selected temperature. The resistive load could be a thin film resistor and the film temperature could be estimated from the measured resistance. In some embodiments, separate thermal sensors placed close to the heating element may be used to measure temperatures, which may be sent to a control unit to control the current through the resistive load. Cold gas or liquid(s) can be injected through tubes and pumped out through the shaft. In an embodiment, the heating element could be the hot side of a Peltier thermoelectric cooler which advantageously cools the opposite surface below ambient temperature with differences of up to about 40° C. In some thermal embodiments, heat may be derived via magnetic or frictional methods to bring about similar tissue alterations.

It has been discovered that some embodiments may also be effective without means for and energy window. For example, in some embodiments lacking an energy window, energy delivered by or otherwise at the lysing elements may be sufficient to at least partially induce fibrosis within a target region as the tissue is separated. In some embodiments and implementations it may therefore be useful to provide a higher energy such a higher level of electrosurgical energy (for example current flow). In some embodiments and implementations, the energy at the lysing elements may be increased beyond what would otherwise be needed just to separate tissue into planes. Although in some embodiments, one may be able to induce target tissue fibrosis by using only the requisite energy needed to separate tissue. In other embodiments, energy may be increased (such as an increase of 5% to 500%) to increase the probability of inducing target tissue fibrosis without the use of an energy window. In other embodiments, energy may be increased (such as an increase of 5% to 150%) to increase the probability of target tissue fibrosis without the use of an energy window In other embodiments, energy may be increased (such as an increase of 10% to 30%) to increase the probability of target tissue fibrosis without the use of an energy window.

Figure 4A:
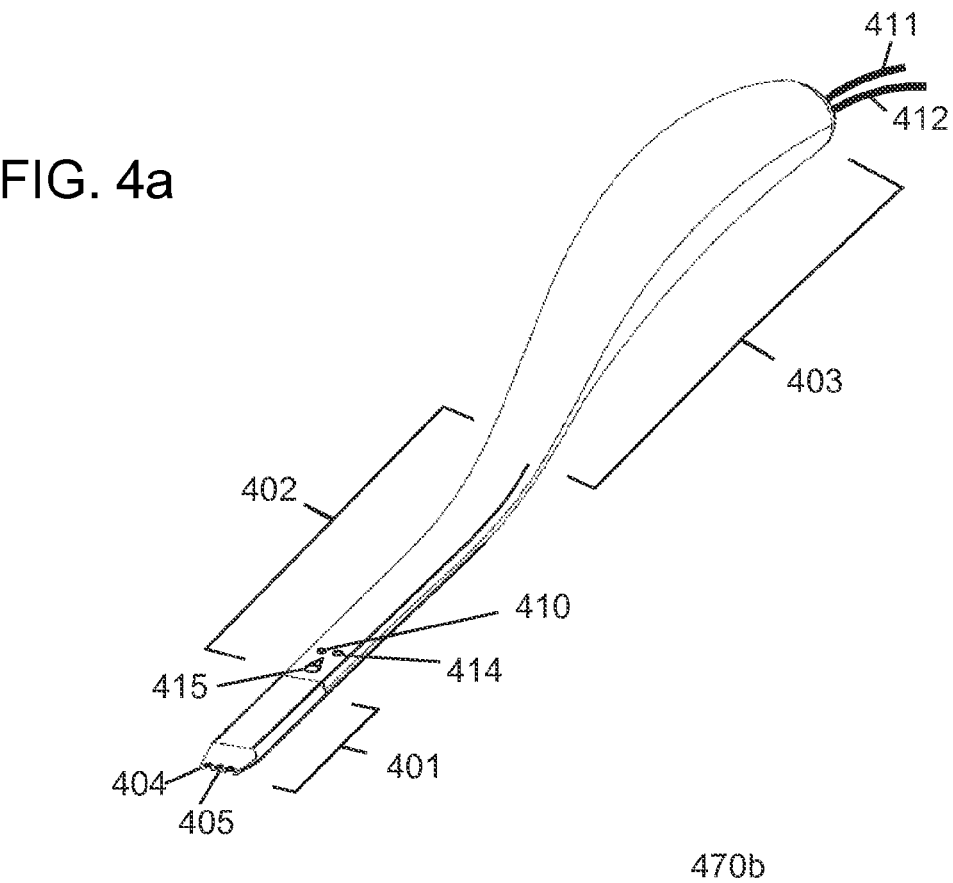
FIG. 4a is a perspective view of an embodiment of a tissue dissector and modifier without an energy window.

FIG. 4a is a perspective view of an embodiment of a TDM comprising a tip 401, a shaft 402 and a handle 403. The embodiment depicted in FIG. 4a is a TDM without an electrosurgically energized energy window. Electro-coagulation and electro-cutting energy arrives in conduits 411 and/or 412 and may travel by wiring through the handle and shaft 402 to electrically conductive lysing elements 405 mounted in the recessions in between the protrusions 404. In the depicted embodiment, the tip 401 may alternatively be made partially or completely of concentrically laminated or annealed-in wafer layers of materials that may include plastics, silicon, glass, glass/ceramics or ceramics. Alternatively, in a further embodiment the tip may be constructed of insulation covered metals or electroconductive materials. In some embodiments, the shaft may be flat, rectangular or geometric in cross-section or substantially flattened. In some embodiments, smoothing of the edges of the shaft may reduce friction on the tissues surrounding the entrance wound. In some further embodiments, the shaft may be made of metal or plastic or other material with a completely occupied or hollow interior that can contain insulated wires, electrical conductors, fluid/gas pumping or suctioning conduits, fiber-optics, or insulation.

In some embodiments, the tip may be constructed of a support matrix of an insulating material (e.g., ceramic or glass material such as alumina, zirconia). The tip shown in this embodiment has four relative protrusions and three relative recessions and provides for a monopolar tip conductive element. All of the axes of the relative protrusions of the tip depicted in this embodiment extend at least substantially parallel to the axis of the shaft of the TDM (as viewed from Top). In embodiments of tips of such axial placement of protrusions and or relative recessions, surgeons may use methods of defining and or dissecting a target area by entering through an incision and then moving the TDM tip in a primarily axial direction forward and backward and reorienting the TDM after the backstroke in a spokewheel pattern the TDM to access tissues adjacent to earlier strokes.

In an embodiment, the tip may measure about 1 cm in width and about 1-2 mm in thickness. Sizes of about one-fifth to about five times these dimensions may also have possible uses. In some embodiments, the tip can be a separate piece that is secured to shaft by a variety of methods such as a snap mechanism, mating grooves, plastic sonic welding, etc. Alternatively, in some other embodiments, the tip can be integral or a continuation of shaft made of similar metal or materials. In some embodiments, the tip may also be constructed of materials that are both electrically non-conductive and of low thermal conductivity; such materials might comprise, for example, porcelain, ceramics, glass-ceramics, plastics, varieties of polytetrafluoroethylene, carbon, graphite, and graphite-fiberglass composites. In some embodiments the geometry of the tip area may comprise protrusions that are not oriented along the axis of the shaft (as seen from a top view); some of these alternative embodiments for tip area geometries are depicted in FIGS. 5a,b,c,d,e,f,g,h and FIGS. 6a,b,c,d.

In some embodiments, shaft plastics, such as polytetrafluoroethylene may act as insulation about wire or electrically conductive elements. In some embodiments, the shaft may alternatively be made partially or completely of concentrically laminated or annealed-in wafer layers of materials that may include plastics, silicon, glass, glass/ceramics, ceramics carbon, graphite, graphite-fiberglass composites.

The conduit may also contain electrical control wires to aid in device operation. Partially hidden from direct view in FIGS. 4a & 4b, and located in the grooves defined by protrusions 404 are electrically conductive tissue lysing elements 405, which, when powered by an electrosurgical generator, effects lysing of tissue planes on forward motion of the device. The lysing segments may be located at the termini of conductive elements.

In some embodiments, one or more sensors such as for example sensors 410 and 414 may be positioned on the device. The sensors 410 and 414 may comprise any of the sensors described in the specification herein. Other embodiments may comprise one or more sensors on any other suitable location on the TDM, including but not limited to on the protrusions or otherwise on the tip, and on the shaft. Sensors that may be useful include thermal sensors, photoelectric or photo optic sensors, cameras, etc. In some embodiments, one or more sensors may be used to monitor the local post passage electrical impedance or thermal conditions that may exist near the distal tip of the shaft or on the tip. Some embodiments may also comprise one or more sensors incorporating MEMS (Micro Electro-Mechanical Systems) technology, such as MEMS gyroscopes, accelerometers, and the like. Such sensors may be positioned at any number of locations on the TDM, including within the handle in some embodiments. In some embodiments, sensor 414 may comprise fiberoptic elements. In an embodiment, the sensor can be configured to sense a temperature of tissue adjacent to the apparatus. The temperature sensor may alternatively be configured or sense a temperature of one or more fluids adjacent to the apparatus such as for example tissue fluids and/or fluids introduced by the surgeon.

Examples of sensors that may be provided with one or more embodiments disclosed herein include electromagnetic sensors, electrical sensors, and temperature sensors. Examples of electromagnetic sensors may include colorimeter, electro-optical sensor, infrared sensor, photodetector, fiberoptic sensor, and/or LEDs as sensors, etc.; also LEDs can be multiplexed in such a circuit, such that it can be used for both light emission and sensing at different times. Examples of electrical sensors may include oxygen sensor, $CO_2$ sensor, pH glass electrode, and/or a current sensor, etc. Examples, of thermal sensors may include Infrared thermometer, resistance temperature detector, resistance temperature detector, resistance thermometer, thermistor, thermocouple, thermometer, etc.

In some embodiments, temperature and impedance values may be tracked on a display screen or directly linked to a microprocessor capable of signaling control electronics to alter the energy delivered to the tip when preset values are approached or exceeded. Typical instrumentation paths are widely known, such as thermal sensing thermistors, and may feed to analog amplifiers which, in turn, feed analog digital converters leading to a microprocessor. In some embodiments, internal or external ultrasound measurements may also provide information which may be incorporated into a feedback circuit. In an embodiment, an optional mid and low frequency ultrasound transducer may also be activated to transmit energy to the tip and provide additional heating and may additionally improve lysing. In some embodiments, a flashing visible light source, for example, an LED, can be mounted on the tip may show through the tissues and/or organs to identify the location of the device.

In some embodiments, one or more electromagnetic delivery elements 415 may be positioned on tip or shaft. Other embodiments may comprise one or more electromagnetic delivery elements on any other suitable location on the TDM, including but not limited to on the protrusions or otherwise on the tip, and on the shaft. Electromagnetic delivery elements that may be useful include: LEDs, LASERs, fiberoptics, filaments, photoelectric materials, infrared emitters, etc.

Alternatively, in some embodiments, since cutting or electrical current may cause an effect at a distance without direct contact, the lysing element may be recessed into the relative recessions or grooves defined by the protrusions 404 or, alternatively, may be flush with protrusions 404. In some further adjustable embodiments, locations of the electrically conductive lysing elements with respect to the protrusions may be adjusted by diminutive screws or ratchets. In some further adjustable embodiments, locations of the electrically conductive lysing elements with respect to the protrusions may be adjusted by MEMS or microelectronics.

Some embodiments may comprise a low cost, disposable, and one-time-use device. However, in some embodiments intended for multiple uses, the tip's electrically conductive tissue lysing elements be protected or coated with materials that include, but are not limited to, Silverglide™ non-stick surgical coating, platinum, palladium, gold and rhodium. Varying the amount of protective coating allows for embodiments of varying potential for obsolescence capable of either prolonging or shortening instrument life.

In some embodiments, the electrically conductive lysing element portion of the tip may arise from a plane or plate of varying shapes derived from the aforementioned materials by methods known in the manufacturing art, including but not limited to cutting, stamping, pouring, molding, additive manufacturing, filing and sanding. In some embodiments, the electrically conductive lysing element 405 may comprise an insert attached to a conductive element in the shaft or continuous with a formed conductive element coursing all or part of the shaft. In some embodiments, an electrically conductive element or wiring in conduit 411 brings RF electrosurgical energy down the shaft to electrically conductive lysing elements 405 associated in part with the recessions. In an embodiment, the electrosurgical energy via conduit 411 is predominately electro-cutting.

In some embodiments, the electrically conductive element or wiring may be bifurcated to employ hand switching if an optional finger switch is located on handle. The electrically conductive element or wiring leading from the shaft into the handle may be bundled with other electrical conduits or energy delivering cables, wiring and the like and may exit the proximal handle as insulated general wiring to various generators (including electrosurgical), central processing units, lasers and other sources as have been described herein. In some embodiments, the plate making up lysing segments 405 may be sharpened or scalloped or made to slightly extend outwardly from the tip recessions into which the plate will fit.

Alternatively, in some embodiments, since cutting or electrical current may cause an effect at a distance without direct contact, the lysing element may be recessed into the relative recessions or grooves defined by protrusions 404 or, alternatively, may be flush with protrusions 404. In some further adjustable embodiments, locations of the electrically conductive lysing elements with respect to the protrusions may be adjusted by diminutive screws or ratchets. The plate, which in some embodiments is between 0.01 mm and 1 mm thick, can be sharpened to varying degrees on its forward facing surface.

It is possible that plate sharpness may increase the efficiency with which electricity will pass from the edge cutting the target tissue. Sometimes, however, proper function even when variably dull or unsharpened may be unhampered since electrosurgical cutting current may cut beyond the electroconductive edge by a distance of over 1 mm.

In some embodiments, the electrically conductive lysing element may also exist in the shape of a simple wire of 0.01 mm to 3 mm. In some embodiments, the wire may measure between 0.1 mm and 1 mm. Such a wire may be singly or doubly insulated as was described for the plate and may have the same electrical continuities as was discussed for the planar (plate) version. In some embodiments, an electrosurgical current for the electrically conductive lysing element is of the monopolar "cutting" variety and setting and may be delivered to the tip lysing conductor in a continuous fashion or, alternatively, a pulsed fashion. The surgeon can control the presence of current by a foot pedal control of the electrosurgical generator or by button control on the shaft (forward facing button). The amount of cutting current may be modified by standard interfaces or dials on the electro surgical generator. In some embodiments, the electrosurgically energized tip current can be further pulsed at varying rates by interpolating gating circuitry at some point external to the electrosurgical generator by standard mechanisms known in the art, that may range from about 1 per second to about 60 per second. In some embodiments, the rate may vary from about 1 per second to about 150 per second. In some embodiments, the electrosurgically energized tip current can be further pulsed at varying rates by gating circuitry within the electrosurgical generator by standard mechanisms known in the art. For some embodiments, the electrically conductive lysing element is a monopolar tip in contact with conductive elements in the shaft leading to external surgical cable leading to an electrosurgical generator from which emanates a grounding or dispersive plate which may be placed elsewhere in contact with the patient's body, such as the thigh.

Such circuitry may be controlled and gated/wired from the cutting current delivery system of the electro surgical generator. Acceptable electrosurgical generators may include Valley Lab Force 1B™ with maximum P-P voltage of 2400 on "cut" with a rated load of 300 Ohms and a maximum power of 200 Watts, 35 maximum P-P voltage of 5000 on "coagulate" with a rated load of 300 Ohms, and a maximum power of 75 Watts ValleyLab Force 4 has a maximum P-P voltage of 2500 on "cut" with a rated load of 300 Ohms and a maximum power of 300 Watts, 750 kHz sinusoidal waveform output, maximum P-P voltage of 9000 on "coagulate" with a rated load of 300 Ohms and a maximum power of 120 Watts using a 750 kHz damped sinusoidal with a repetition frequency of 31 kHz. In an embodiment, the tip may also be manufactured from multilayer wafer substrates comprised of bonded conductive strips and ceramics. Suitable conductive materials include but are not limited to those already described for tip manufacture. In some embodiments, electrically non-conductive portions of the tip may comprise ceramics. In some embodiments, electrically conductive portions of the tip may comprise cermets.

In alternative embodiments the geometry of the tip area may comprise protrusions that are not oriented along the axis of the shaft (as seen from a top view); some of these alternative embodiments for tip area geometries are depicted in FIGS. 5a,b,c,d,e,f,g,h and FIGS. 6a,b,c,d. Some embodiments may be configured to be modular and/or comprise disposable tips such that a surgeon can place an appropriate tip for a particular surgery on the shaft. Alternatively or additionally one or more of the tips may be disposable such that a surgeon may dispose of the tip after performing surgery and install a new tip for subsequent surgeries or a continuation of the current surgery with a new tip.

In some embodiments, a vibration means 470b may be positioned in the handle. Other embodiments may comprise one or more vibration means on any other suitable location on the TDM, including but not limited to on the protrusions or otherwise on the tip, and on the shaft. Examples of suitable vibration means may include piezoelectric materials, ultrasonic motors with stators, piezoelectric actuators, vibration motor such as an off-center weight mounted on a gear, etc. Some vibration means may be configured to emit ultrasound in the 20-40 kHz range. Yet other vibration means may include electromagnet drivers with a frequency of operation in the range of 150-400 Hz. In some embodiments, one or more vibration means may be used to provide additional forces which may facilitate passage of the TDM. In some embodiments, one or more vibration means may be used to reduce debris on the electrosurgical or other components of the TDM. In a further embodiment, a vibration means may be directly or indirectly connected to one or more of the lysing segments.

Figure 4B:
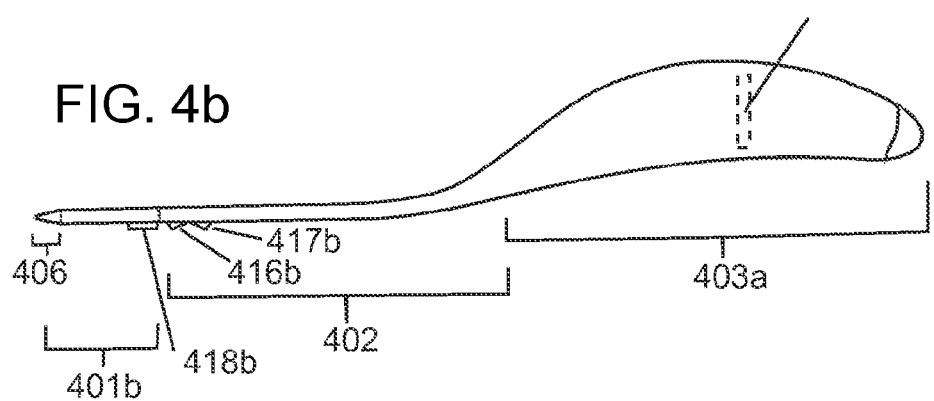

In alternative embodiments, the electrically conductive lysing elements may be bifurcated or divided into even numbers at the relative recessions, insulated and energized by wiring to an even number of electrical conduits in a bipolar fashion and connected to the bipolar outlets of the aforementioned electrosurgical generators. Rings partly or completely encircling the shaft of the hand unit can be linked to a partner bipolar electrode at the tip or on the energy window. Such bipolar versions may decrease the available power necessary to electrically modify certain tissues, especially thicker tissues In alternative embodiments, the lysing elements may be divided into odd numbers yet still allow for bipolar flow between two or more elements as those of ordinary skill in the art would appreciate. FIG. 4b is a side elevation view of the embodiment previously depicted in FIG. 4a. In the depicted embodiment, tip 401b may be made of materials that are both electrically non-conductive and of low thermal conductivity such as porcelain, epoxies, ceramics, glass-ceramics, plastics, or varieties of polytetrafluoroethylene. Alternatively, the tip may be made from metals or electroconductive materials that are completely or partially insulated. Note the relative protrusions and relative recessions are not completely visible from this viewing angle. The tip shown in this embodiment has four relative protrusions and three relative recessions and provides for a monopolar tip conductive element. In some embodiments, the relative recessions of the tip is the electrically conductive tissue lysing element 405 (usually hidden from view at most angles) which may have any geometric shape including a thin cylindrical wire; the electrically conductive lysing element can be in the shape of a plate or plane or wire and made of any metal or alloy that does not melt under operating conditions or give off toxic residua. Optimal materials may include but are not limited to steel, nickel, alloys, palladium, gold, tungsten, silver, copper, and platinum. Metals may become oxidized thus impeding electrical flow and function. In an embodiment, the lysing element may comprise a cermet.

In some embodiments, one or more suction/vacuum ports 417b may be provided on or about the tip or distal shaft. The port(s) may be fluidly coupled with a vacuum; the vacuum may comprise a pump or a negative pressure chamber or a syringe at the end of a fluid conduit. Other embodiments may comprise one or more suction/vacuum ports on any other suitable location on the TDM, including but not limited to on the protrusions or otherwise on the tip, and on the shaft. In some embodiments, a fluid delivery port 416b may be provided. In some embodiments the fluid delivery port may be coupled with a pump or high pressure fluid. In some embodiments the port may be perpetually open such that fluid may be delivered therethrough upon actuation of a pump or fluid pressure system. In other embodiments the port may be closed and selectively opened to deliver fluid therethrough. Other embodiments may comprise one or more fluid ports on any other suitable location on the TDM, including but not limited to on the protrusions or otherwise on the tip, and on the shaft. Fluid ports that may be useful may comprise channels within the TDM, polymer lines, hoses, etc. Fluids that may emanate from the outlet may comprise ionic fluids such as saline, medicines (including but not limited to antibiotics, anesthetics, antineoplastic agents, bacteriostatic agents, etc.), non-ionic fluids, and or gasses (including but not limited to nitrogen, argon, air, etc.). In some embodiments fluids may be under higher pressures or sprayed. It should be understood that although these elements (416b & 417b) are not depicted in every one of the other figures, any of the embodiments described herein may include one or more such elements.

In the depicted embodiment, 418b represents an antenna, such as an RFID TAG. In embodiments in which antenna 418b comprises an RFID tag, the RFID tag may comprise an RFID transponder. In other embodiments the RFID tag may comprise a passive tag. It should be understood that antenna 418b is not depicted in every one of the other figures, any of the embodiments described herein may comprise one or more such elements. Other embodiments may comprise one or more antennas on any other suitable location on the TDM, including but not limited to on the protrusions or otherwise on the tip, and on the shaft. In some embodiments an RFID transponder or another antenna may comprise a microchip, such as a microchip having a rewritable memory. In some embodiments, the tag may measure less than a few millimeters. In some embodiments a reader may generate an alternating electromagnetic field which activates the RFID transponder/antenna and data may be sent via frequency modulation. In an embodiment, the position of the RFID tag/antenna may be determined by an alternating electromagnetic field in the ultra-high frequency range. The position may be related to a 3 dimensional mapping of the subject. In an embodiment the reader may generate an alternating electromagnetic field. In some such embodiments, the alternating electromagnetic field may be in the shortwave (13.56 MHz) or UHF (865-869 MHz) frequency.

In some embodiments tip 401 may be attached to a robotic arm. In some embodiments, tip 401 and portion of shaft 402 may be attached to a robotic arm. In some embodiments tip 401 and/or a portion of shaft 402 and/or a portion shaft and/or portion of handle 403 may be attached to a robotic arm. In some embodiments, the robotic arm may comprise one or more motors such as a screw-drive motor, gear motor, hydraulic motors, etc. In some embodiments the robotic arm system may comprise worm gearheads, video cameras, motor control circuits, monitors, remote control devices, illumination sources, tactile interface, etc.

FIG. 5a is an upper plan view illustrating the protrusions and lysing segments of an embodiment of a tissue dissector and modifier, wherein some of the protrusions and lysing segments are oriented in a non-axial direction and the non-axial protrusions do not extend beyond the width of the distal shaft (and the axis of comparison is that of the shaft as seen from a top view). In some embodiments, the tip may measure about 1 cm in width and about 1-2 mm in thickness. Sizes of about one-fifth to about five times these dimensions may also have possible uses.

In the embodiment depicted in FIG. 5a, the non-axial protrusions 551a of tip 501a do not extend beyond the width of the distal shaft 502a, which leads to handle 503a. In this embodiment, non-axial protrusions 551a extend in a direction that is at least substantially perpendicular to the direction in which axial protrusions 504a extend. More particularly, there are two sets of non-axial protrusions 551a (one depicted on the right side and one on the left side of the embodiment of FIG. 5a). Both sets of non-axial protrusions 551a extend in directions that are at least substantially perpendicular to the direction in which axial protrusions 504a extend (namely, along a longitudinal axis of the TDM shaft). In addition, it can be seen in FIG. 5a that the two sets of non-axial protrusions 551a extend in directions that are at least substantially opposite from one another.

In some embodiments, axial protrusions 504a may extend at least substantially along a longitudinal axis of the shaft, as described above, and non-axial protrusions 551a may extend at an angle of between zero degrees and 30 degrees of a normal to the direction in which the axial protrusions 504a extend. It is contemplated that it may be desirable for some implementations and embodiments to provide non-axial tips extending in a direction or directions falling within this range in order to, for example, allow a surgeon to effectively perform both a to and fro, and a side-to-side ("windshield wiper") motion using the TDM.

In some embodiments, the tip can be a separate piece that is secured to the shaft by a variety of methods such as a snap mechanism, mating grooves, plastic sonic welding, etc. Alternatively, in some other embodiments, the tip can be integral or a continuation of a shaft made of similar metal or materials. In some embodiments, the tip may also be constructed of materials that are both electrically non-conductive and of low thermal conductivity; such materials might comprise, for example, porcelain, ceramics, glass-ceramics, plastics, varieties of polytetrafluoroethylene, carbon, graphite, and graphite-fiberglass composites. In some embodiments, the tip may be constructed of a support matrix of an insulating material (e.g., ceramic or glass material such as alumina, zirconia). External power control bundles as previously described in other embodiments may connect to electrically conductive elements to bring RF electrosurgical energy from an electrosurgical generator down the shaft 502a to electrically conductive lysing elements 552a mounted in the recessions in between the protrusions 551a. In some embodiments, the protrusions may comprise bulbous protrusions. The tip shown in this embodiment has two relative protrusions and three relative recessions pointing along the main axis of the TDM and provides for a monopolar tip conductive element; the tip shown also has fourteen protrusions pointing in non-axial directions as well as fourteen relative recessions pointing in non-axial directions. In other embodiments the tip may have one or more non-axial protrusions and one or more non-axial relative recessions. In some embodiments the tip may have between 3 and 100 non-axial protrusions and relative recessions. In the depicted embodiment, the tip 501a may alternatively be made partially or completely of concentrically laminated or annealed-in wafer layers of materials that may include plastics, silicon, glass, glass/ceramics, cermets or ceramics. Lysing elements 552a may also be made partially or completely of a cermet material. Alternatively, in a further embodiment the tip may be constructed of insulation covered metals or electroconductive materials. The lysing segments may be located at the termini of conductive elements.

In the depicted embodiment, tip 501a which terminates in protrusions such as 504a and 551a may be made of materials that are both electrically non-conductive and of low thermal conductivity such as porcelain, epoxies, ceramics, glass-ceramics, plastics, or varieties of polytetrafluoroethylene. Alternatively, the tip may be made from metals or electroconductive materials that are completely or partially insulated. In some embodiments, the electrically conductive tissue lysing element(s) $552a$ may have any geometric shape including a thin cylindrical wire, and may be positioned within the relative recessions of the tip. The electrically conductive lysing element can be in the shape of a plate or plane or wire and made of any metal or alloy that does not melt under operating conditions or give off toxic residua. Optimal materials may include but are not limited to steel, nickel, alloys, palladium, gold, tungsten, silver, copper, and platinum. Metals may become oxidized thus impeding electrical flow and function.

In some embodiments, the shaft may be flat, rectangular or geometric in cross-section and/or substantially flattened. In some embodiments, smoothing of the edges of the shaft may reduce friction on the tissues surrounding the entrance wound. In some further embodiments, the shaft may be made of metal or plastic or other material with a completely occupied or hollow interior that can contain insulated wires, electrical conductors, fluid/gas pumping or suctioning conduits, fiber-optics, or insulation.

In some embodiments, shaft plastics, such as polytetrafluoroethylene, may act as insulation about wire or electrically conductive elements. In some embodiments, the shaft may alternatively be made partially or completely of concentrically laminated or annealed-in wafer layers of materials that may include plastics, silicon, glass, glass/ceramics, ceramics carbon, graphite, and/or graphite-fiberglass composites.

In FIG. 5$a$ the depicted view of an embodiment of a TDM with an alternative energy window $507a$ on the upper side of the device may be configured to hold an ultrasound energy emitter. It should be noted that the term "energy window" is intended to encompass what is referred to as a planar-tissue-altering-window/zone in U.S. Pat. No. 7,494,488 and, as described herein, need not contain a ultrasonic energy emitter in all embodiments. Additionally, the "energy window" may comprise a variety of other energy emitting devices, including but not limited to radiofrequency, microwave, light, intense pulsed light, LASER, and thermal. Certain components of the energy window, such as the electro-conductive components of the energy window, could comprise a cermet. A second energy window $508a$ may also be included in some embodiments, and may comprise yet another ultrasonic energy emitter or another variety of energy emitting device. In some embodiments, energy windows $507a$ and/or $508a$ may only be substantially planar, or may take on other cross-sectional shapes that may correspond with a portion of the shape of the shaft, such as arced, stair-step, or other geometric shapes/curvatures. In the embodiment depicted in FIG. 5$a$, energy window $507a$ is adjacent to protrusions $504a$ and $551a$, however other embodiments are contemplated in which an energy window may be positioned elsewhere on the shaft $502a$ or tip $501a$ of the wand, and still be considered adjacent to protrusions $504a$ or $551a$. For example, in an embodiment lacking energy window $507a$, but still comprising energy window $508a$, energy window $508a$ would still be considered adjacent to protrusions $504a$ and $551a$. However, if an energy window was placed on handle $503a$, such an energy window would not be considered adjacent to protrusions $504a$ or $551a$.

In some embodiments, one or more sensors such as for example sensors $510a$ and $514a$ may be positioned on the device. The sensors $510a$ and $514a$ may comprise any of the sensors described in the specification herein. Other embodiments may comprise one or more sensors on any other suitable location on the TDM, including but not limited to on the protrusions or otherwise on the tip, and on the shaft. Sensors that may be useful include thermal sensors, photoelectric or photo optic sensors, cameras, etc. In some embodiments, one or more sensors may be used to monitor the local post passage electrical impedance or thermal conditions that may exist near the distal tip of the shaft or on the tip. Some embodiments may also comprise one or more sensors incorporating MEMS (Micro Electro-Mechanical Systems) technology, such as MEMS gyroscopes, accelerometers, and the like. Such sensors may be positioned at any number of locations on the TDM, including within the handle in some embodiments. In some embodiments, sensor $514a$ may comprise fiberoptic elements. In an embodiment, the sensor can be configured to sense a temperature of tissue adjacent to the apparatus during one or methods described herein. The temperature sensor may alternatively be configured or sense a temperature of one or more fluids adjacent to the apparatus such as for example tissue fluids and/or fluids introduced by the surgeon.

Temperature and impedance values may be tracked on a display screen or directly linked to a microprocessor capable of signaling control electronics to alter the energy delivered to the tip when preset values are approached or exceeded. Typical instrumentation paths are widely known, such as thermal sensing thermistors, and may feed to analog amplifiers which, in turn, feed analog digital converters leading to a microprocessor. In some embodiments, internal or external ultrasound measurements may also be taken during a procedure with the TDM. Sensors that may be useful include thermal sensors, photoelectric or photo optic sensors, cameras, etc. Temperature sensors that may be useful in connection with embodiments disclosed herein include, but are not limited to, resistance temperature sensors, such as carbon resistors, film thermometers, wire-wound thermometers, or coil elements. Some embodiments may comprise thermocouples, pyrometers, or non-contact temperature sensors, such as total radiation or photoelectric sensors.

In some embodiments, one or more electromagnetic delivery elements $515a$ may be positioned on tip or shaft. Other embodiments may comprise one or more electromagnetic delivery elements on any other suitable location on the TDM, including but not limited to on the protrusions or otherwise on the tip, and on the shaft. Electromagnetic delivery elements that may be useful include: LEDs, LASERs, fiberoptics, filaments, photoelectric materials, infrared emitters, etc.

In embodiments of tips with at least some non-axial placement of protrusion and or relative recessions, surgeons may implement the use of a fanning motion which may comprise a 'windshield wiper' motion.

FIG. 5$b$ is an upper plan view illustrating the protrusions and lysing segments of an alternative embodiment of a tissue dissector and modifier, wherein some of the protrusions and lysing segments are oriented in a non-axial direction and some of the non-axial protrusions extend beyond the width of the distal shaft. In the depicted embodiment $501b$ represents the tip area which lies adjacent to shaft area $502b$ which is connected to handle area $503b$; $504b$ represents an axially aligned protrusion; $551b$ represents a non-axially aligned protrusion; $552b$ represents a non-axially aligned relative recession; $507b$ represents a first energy window; $508b$ represents a second energy window; $510b$ and $514b$ represent sensor elements; $515b$ represents an electromagnetic radiation delivery element.

FIG. 5$b$ is an upper plan view illustrating the protrusions and lysing segments of an alternative embodiment of a tissue dissector and modifier, wherein some of the protrusions and lysing segments are oriented in a non-axial direction and some of the non-axial protrusions extend beyond the width of the distal shaft. In the depicted embodiment 501b represents the tip area which lies adjacent to shaft area 502b which is connected to handle area 503b; 504b represents an axially aligned protrusion; 551b represents a non-axially aligned protrusion; 552b represents a non-axially aligned relative recession; 507b represents a first energy window; 508b represents a second energy window; 510b and 514b represent sensor elements similar to those previously discussed in other embodiments; 515b represents an electromagnetic radiation delivery element similar to those previously discussed in other embodiments.

FIG. 5c is a lower plan view of the embodiment of FIG. 5a illustrating the protrusions and lysing segments of a tissue dissector and modifier, wherein some of the protrusions and lysing segments are oriented in a non-axial direction and the non-axial protrusions do not extend beyond the width of the distal shaft. In the depicted embodiment 501a represents the tip area which lies adjacent to shaft area 502a which is connected to handle area 503a; 516a represents a fluid port; 517a represents a suction and/or vacuum port; 518a represents an antenna, such as an RFID TAG. In embodiments in which antenna 518a comprises an RFID tag, the RFID tag may comprise a RFID transponder. In other embodiments the RFID tag may comprise a passive tag. It should be understood that although antenna 518a is not depicted in every one of the other figures, any of the embodiments described herein may include one or more such locations. Other embodiments may comprise one or more antennas on any other suitable location on the TDM, including but not limited to on the protrusions or otherwise on the tip, and on the shaft. In some embodiments an RFID transponder or other antenna may comprise a microchip such as a microchip having a rewritable memory. In an embodiment the tag is millimeter sized. In some embodiments a reader generates an alternating electromagnetic field which activates the antenna/RFID transponder and data is sent via frequency modulation. In an embodiment, the position of the antenna/RFID tag is determined by an alternating electromagnetic field in the ultra-high frequency range. The position may be related to a 3 dimensional mapping of the subject. In an embodiment the reader may generate an alternating electromagnetic field. In a further embodiment the alternating electromagnetic field may be in the shortwave (13.56 MHz) or UHF (865-869 MHz) frequency.

In some embodiments, a suction/vacuum port 517a may be provided on or about the tip or distal shaft. The port may be fluidly coupled with a vacuum; the vacuum may comprise a pump or a negative pressure chamber or a syringe at the end of a fluid conduit. Other embodiments may comprise one or more suction/vacuum ports on any other suitable location on the TDM, including but not limited to on the protrusions or otherwise on the tip, and on the shaft. In some embodiments, a fluid delivery port 516a may be provided. In some embodiments the fluid delivery port may be coupled with a pump or high pressure fluid. In some embodiments the port may be perpetually open such that fluid may be delivered therethrough upon actuation of a pump or fluid pressure system. In other embodiments the port may be closed and selectively opened to deliver fluid therethrough. Other embodiments may comprise one or more fluid ports on any other suitable location on the TDM, including but not limited to on the protrusions or otherwise on the tip, and on the shaft. Fluid ports that may be useful include channels within the TDM, polymer lines, etc. Fluids that may emanate from the port may include ionic fluids such as saline, medicines (including but not limited to antibiotics, anesthetics, antineoplastic agents, bacteriostatic agents, etc.), non-ionic fluids, and or gasses (including but not limited to nitrogen, argon, air, etc.). In some embodiments fluids and or gasses may be under pressure or sprayed. It should be understood that although elements 516a and/or 517a are not depicted in every one of the other figures, any of the embodiments described herein may include one or more such elements.

In some embodiments tip 501a may be attached to a robotic arm. In some embodiments tip 501a and portion of shaft 502a may be attached to a robotic arm. In some embodiments tip 501a and a portion of shaft 502a and or a portion of handle 503a may be attached to a robotic arm.

FIG. 5d is a lower plan view of the embodiment of FIG. 5b illustrating the protrusions and lysing segments of a tissue dissector and modifier, wherein some of the protrusions and lysing segments are oriented in one or more non-axial directions and at least some of the non-axial protrusions extend beyond the width of the distal shaft. In the depicted embodiment tip area 501b represents the tip area which lies adjacent to shaft area 502b which is connected to handle area 503b; this particular embodiment also comprises fluid port 516b; suction port 517b; 518b represents an antenna, such as an RFID TAG. In embodiments in which the antenna comprises an RFID tag, the RFID tag may comprise a RFID transponder. In other embodiments the RFID tag may comprise a passive tag. It should be understood that although antenna 518b is not depicted in every one of the other figures, any of the embodiments described herein may include one or more such locations FIG. 5e is an upper plan view illustrating the protrusions and lysing segments of an embodiment of a tip area of a tissue dissector and modifier. This embodiment comprises a plurality of axial protrusions 504e (axially meaning at least substantially parallel to an axis of a corresponding TDM shaft). This embodiment further comprises a plurality of non-axial protrusions 551e along the right side of the tip and a plurality of non-axial protrusions positioned along the left side of the tip. The tip further comprises two non-axial corner protrusions 554e. The tip further comprises a plurality of recessions 552e. One or more of the recessions may further comprise a lysing segment 553e. 556e is an edge of the tip not populated with protrusions or relative recessions. 507e is a first energy window located in the base 555e of tip 501a; 557e is a tab that extends from base 555e and may be used to secure the tip within a corresponding shaft of a TDM device. Tab 557e may be made up of a ceramic material in some embodiments. Tab 557e may further comprise cut-out regions 558e to allow for a snap or fixation of the tip inside a corresponding TDM shaft.

FIG. 5f is an upper plan view illustrating the protrusions and lysing segments of another embodiment of a tip area of a tissue dissector and modifier. This embodiment may comprise a plurality of axial protrusions 504f and a plurality of non-axial protrusions 551f. In addition, this embodiment comprises two transitional or corner protrusions 554f. A plurality of recessions 552f are also depicted, one or more of which may comprise corresponding lysing segments 553f. 556f is an edge of the tip not populated with protrusions or relative recessions. 555f is the base of tip 501f; a first energy window, may be at least partially located in a space 507f of hollow tab 557f of tip 501f. 557f is a tab that, as described above, may be used to secure the tip inside a corresponding shaft of a TDM device. The embodiment of FIG. 5f may further comprise a slot 558f in tab 557f to allow for a snap or fixation of the tip inside the shaft. In other embodiments, the base of the tip may also have a cavity or space to accommodate a portion of the distal shaft; also, the distal shaft may have a cavity or space to accommodate a portion of a tab of a tip.

FIG. 5g is an upper plan view illustrating the protrusions and lysing segments of an embodiment of a tip area of a tissue dissector and modifier. This embodiment comprises a plurality of axial protrusions; this embodiment further comprises a plurality of non-axial protrusions 551g along the right side of the tip and a plurality of non-axial protrusions positioned along the left side of the tip. The tip further comprises two non-axial corner protrusions. The tip further comprises a plurality of recessions 552g. One or more of the recessions may further comprise a lysing segment 553g. 560g is a space within the base of the tip that may be used to secure a portion of a shaft within this TDM device tip.

FIG. 5h is a lower plan view illustrating the protrusions and lysing segments of another embodiment of a tip area of a tissue dissector and modifier. This embodiment may comprise a plurality of axial protrusions and a plurality of non-axial protrusions 551h. In addition, this embodiment comprises two transitional or corner protrusions. A plurality of recessions 552h are also depicted, one or more of which may comprise corresponding lysing segments. A first energy window, may be at least partially located within a hollow space 507h which is in turn located between the legs of tab 557h of tip 501h. Tab 557h may be used to secure the tip inside a corresponding shaft of a TDM device. The embodiment of FIG. 5h may further comprise one or more slots in tab 557h to allow for a snap or fixation of the tip inside the shaft. The tip of FIG. 5h further comprises antenna 518h, such as an RFID tag.

The tips depicted in FIGS. 5a,b,c,d,e,f,g,h and FIGS. 6a,b, c,d are contemplated to be able to be used with any of the embodiments discussed herein. Said tips are not intended to be restricted to symmetry and/or pattern and/or dimension. In other embodiments said tips may be asymmetrical or lacking protrusions and/or lysing segments on one side or another.

FIG. 6a is an upper plan view illustrating an embodiment of a tissue dissector and modifier with an asymmetrical tip area. More particularly, the embodiment of FIG. 6a comprises a plurality of axial protrusions 604a along the distal end of the tip 601a, and a plurality of non-axial protrusions 651a along a left side of the tip 601a. The right side of the tip 601a lacks any protrusions and thus also lacks recessions. Instead, the right side of the tip 601a comprises an at least substantially flat surface 659a. Since the left and right sides of tip 601a differ, the embodiment of FIG. 6a comprises an asymmetrical tip 601a. In addition, the non-axial protrusions 651a do not extend beyond the width of the distal shaft 602a, as shown in the figure. The embodiment of FIG. 6a further comprises a first energy window 607a positioned on tip 601a and a second energy window 608a positioned on shaft 602a. In addition, the embodiment of FIG. 6a comprises an electromagnetic delivery element 615a, a first sensor 610a and a second sensor 614a. Each of these three components is positioned on the shaft 602a. However, as previously described, in alternative embodiments, one or more such components may be located elsewhere on the device, such as on the tip 601a and/or handle 603a.

Figure 6B:
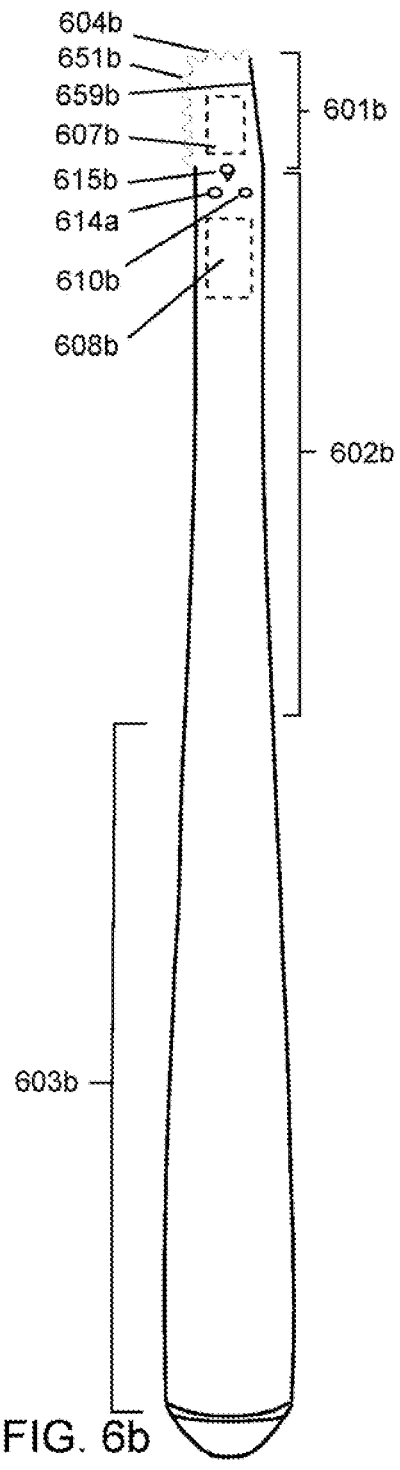
FIG. 6b is an upper plan view illustrating another embodiment of a tissue dissector and modifier with an asymmetrical tip area, wherein some of the protrusions and lysing segments are oriented in a non-axial direction and some the non-axial protrusions extend beyond the width of the distal shaft.

FIG. 6b is an upper plan view illustrating another embodiment of a tissue dissector and modifier with an asymmetrical tip area. Like the embodiment of FIG. 6a, this embodiment comprises both axial and non-axial protrusions. However, unlike the embodiment of FIG. 6a, this embodiment comprises non-axial protrusions that extend beyond the width of the distal shaft 602b.

More particularly, the embodiment of FIG. 6b comprises a plurality of axial protrusions 604b positioned along the distal end of the tip 601b, and a plurality of non-axial protrusions 651b positioned along a left side of the tip 601b. The right side of the tip 601b lacks any protrusions and thus also lacks recessions. Like the embodiment of FIG. 6a, the right side of the tip 601b comprises an at least substantially flat surface 659b. Since the left and right sides of tip 601b differ, the embodiment of FIG. 6b also comprises an asymmetrical tip 601b. As previously mentioned, the non-axial protrusions 651b extend beyond the width of the distal shaft 602b.

Like the embodiment of FIG. 6a, the embodiment of FIG. 6b further comprises a first energy window 607b positioned on tip 601b and a second energy window 608b positioned on shaft 602b. In addition, the embodiment of FIG. 6b comprises an electromagnetic delivery element 615b, a first sensor 610b and a second sensor 614b. Each of these three components is positioned on the shaft 602b. However, as previously described, in alternative embodiments, one or more such components may be located elsewhere on the device, such as on the tip 601b and/or handle 603b.

Figures 6C, 6D:
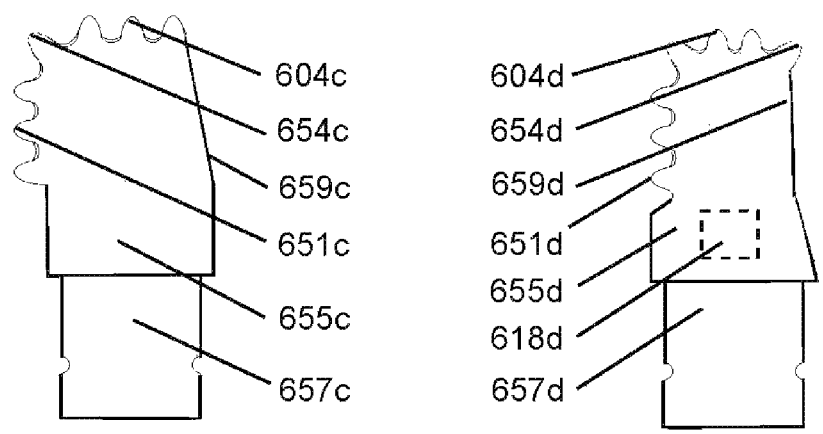
FIG. 6c is an upper plan view illustrating the protrusions and lysing segments of an embodiment of a tip area of a tissue dissector and modifier, wherein the tip is asymmetrical.
FIG. 6d is an upper plan view illustrating the protrusions and lysing segments of an embodiment of a tip area of a tissue dissector and modifier, wherein the tip is asymmetrical.

FIG. 6c is an upper plan view illustrating the protrusions and lysing segments of an embodiment of a tip area of a tissue dissector and modifier. The tip depicted in this figure is asymmetrical since side 659c lacks protrusions and the opposite side comprises non-axial protrusions 651c. This embodiment also comprises a corner protrusion 654c that extends at a transitional angle relative to axial protrusions 604c and non-axial side protrusions 651c. In some embodiments, one or more transitional angle is acute. In some embodiments, one or more transitional angles may be obtuse. As shown in the figure, protrusions 651c extend beyond the profile of the tip, and therefore may extend beyond a width of a corresponding shaft.

In some embodiments, the tip depicted in FIG. 6c may be modular such that the tip may be selectively added to, and removed from, a corresponding shaft of a TDM device. Such a modular system may allow a surgeon to, for example, dispose of the tip after or during a surgery due to debris build-up. Additionally, or alternatively, such a modular tip may allow a surgeon to use a variety of different tips useful for a variety of different types of surgical procedures. Tab 657c, which extends from base 655c of the tip, may be used to secure the tip to a corresponding TDM shaft. For example, some embodiments of TDM shafts may be configured with a slot configured to receive tab 657c. One or more clips, recesses, protrusions, or the like, may be used to secure the tab 657c within its corresponding slot, such as by way of a snap-fit engagement, for example. Alternatively, tab 657c may be configured to fit within a corresponding slot with a friction fit, adhesive, screws, bolts, rivets, or other fasteners.

FIG. 6d is a lower plan view illustrating the protrusions and lysing segments of another embodiment of a tip area of a tissue dissector and modifier, wherein the tip is asymmetrical. The tip of FIG. 6d also comprises a tab 657d extending from base 655d and therefore, as described above in connection with the embodiment of FIG. 6c, may be modular such that the tip can be removed from and/or selectively coupled with a corresponding TDM shaft.

The tip of FIG. 6d further comprises a plurality of axial protrusions 604d, a plurality of side, non-axial protrusions 651d, and two corner protrusions 654d extending from opposing corners of the distal end of the tip. Unlike the embodiment of FIG. 6c, the side, non-axial protrusions 651d of the embodiment of FIG. 6d do not extend beyond the profile of the tip, and therefore may be configured so as to avoid extending beyond a width of a distal portion of a corresponding shaft of a TDM. The tip of FIG. 6d further comprises an antenna 618d, such as an RFID tag.

Figures 7A, 7B:
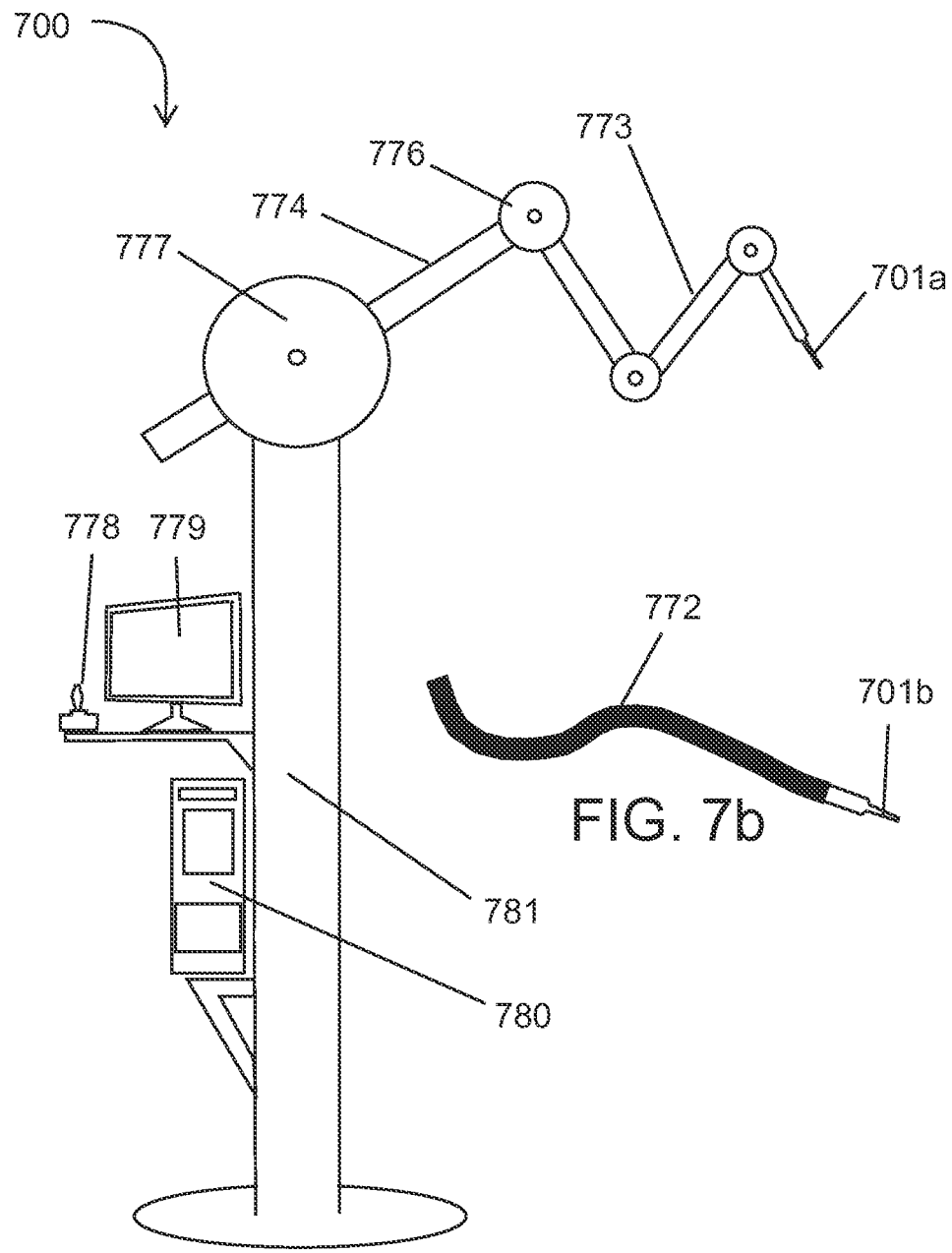
FIG. 7a is a side view of a robotic surgery system comprising a TDM.
FIG. 7b depicts an alternative robotic arm that may be used with the system of FIG. 7a FIG. 8 is a flow chart illustrating one implementation of a method for energy delivery modulation via temperature measurements.

An embodiment of a system 700 for performing robotic surgery using a TDM is depicted in FIG. 7a. System 700 may comprise a tissue dissecting and modifying wand (TDM) 701. TDM 701 may comprise a tissue dissecting and modifying wand (TDM) that may, as described elsewhere herein, comprise a plurality of protrusions with one or more recessions positioned therebetween. TDM 701 may be coupled with one or more robotic surgery components, such as a surgical arm.

In some embodiments, TDM 701 may comprise a shaft, a tip, and/or a handle, as described elsewhere in this disclosure. In such embodiments, TDM 701 may be selectively coupled to a robotic arm such that the TDM 701 can either be used by hand, or coupled with one or more robotic surgery components to allow a surgeon to perform a surgical procedure with the TDM 701 remotely and/or indirectly. In other embodiments, the TDM may be configured to be integrally coupled with, or otherwise non-selectively coupled with, one or more robotic surgery components. In such embodiments, it may not be necessary to configure the TDM 701 with a handle and/or shaft. In other words, in some embodiments, the TDM 701 may comprise only a tip.

In some embodiments, the robotic surgery system 700 may comprise one or more motors, such as a screw-drive motor, gear motor, hydraulic motors, etc. In some embodiments, the robotic surgery system 700 may comprise worm gearheads, video cameras, motor control circuits, monitors, remote control devices, illumination sources, tactile interface, etc. In the embodiment depicted in FIG. 7a, TDM 700 comprises a TDM tip 701a that is positioned at the end of a robotic arm. This robotic arm comprises a plurality of arm segments 773 with corresponding joints 776 positioned therebetween. A primary joint 777 may be positioned to support and articulate together each of the arm segments 773 and smaller joints 776. Primary joint has a primary arm segment 774 that extends therefrom. Finer movements of the robotic arm may then be accomplished using one or more of the smaller joints 776. A stand 781 may also be provided to support the various robotic arms. In some embodiments, stand 781 may also be configured to support a monitor 779 and/or other display, input, or control components, such as a control element 778. In some embodiments, control element 778 may comprise a hand control toggle 778. In other embodiments, control element 778 may comprise a keyboard, mouse, touchscreen display, virtual reality system, control pad, or the like. Monitor 779 and/or control element 778 may be communicatively coupled with a central processing unit 780.

Central processing unit 780 may comprise, for example, one or more microprocessors and/or other electronic components, such as data connectivity elements, memory, non-transitory computer readable media, etc. In some embodiments, central processing unit 780 may comprise a general-purpose computer. Central processing unit 780 may further comprise a machine-readable storage device, such as non-volatile memory, static RAM, dynamic RAM, ROM, CD-ROM, disk, tape, magnetic storage, optical storage, flash memory, or another machine-readable storage medium.

FIG. 7b illustrates an alternative embodiment of a robotic arm 772 that may be used with system 700. Robotic arm 772 comprises an endoscopic snake-like robotic arm 772 and also comprises a TDM 701b positioned at its distal end. As with the embodiment of FIG. 7a, TDM 701b may be selectively coupled to robotic arm 772 or, alternatively, may be integrally or otherwise non-selectively coupled to robotic arm 772. Further details regarding robotic surgery components that may be useful in connection with the various embodiments disclosed herein may be found in the following U.S. patent Nos., each of which is hereby incorporated by reference in its entirety: U.S. Pat. No. 4,259,876 titled Mechanical Arm, U.S. Pat. No. 4,221,997 titled Articulated Robot Arm and Method Of Moving Same, U.S. Pat. No. 4,462,748 titled Industrial Robot, U.S. Pat. No. 4,494,417 titled Flexible Arm, Particularly a Robot Arm, U.S. Pat. No. 4,631,689 titled Multi-Joint Arm Robot Apparatus, U.S. Pat. No. 4,806,066 titled Robotic Arm, U.S. Pat. No. 5,791,231 titled Surgical Robotic System and Hydraulic Actuator Therefor, U.S. Pat. No. 7,199,545 titled Robot For Surgical Applications, U.S. Pat. No. 7,316,681 titled Articulated Surgical Instrument For Performing Minimally Invasive Surgery With Enhanced Dexterity and Sensitivity, U.S. Pat. No. 8,182,418 titled Systems and Methods for Articulating An Elongate Body, U.S. Pat. No. 8,224,485 titled Snaking Robotic Arm With Movable Shapers.

Any of the embodiments of TDM discussed herein including, but not limited to, the embodiments discussed with FIGS. 1a-g, FIGS. 2a-b, FIGS. 3a-c, FIGS. 4a-b, FIGS. 5a,b,c,d,e,f,g,h and FIGS. 6a,b,c,d, etc. may be used in conjunction with one or more of the robotic surgery elements disclosed in connection with FIGS. 7a-b.

Figure 8:
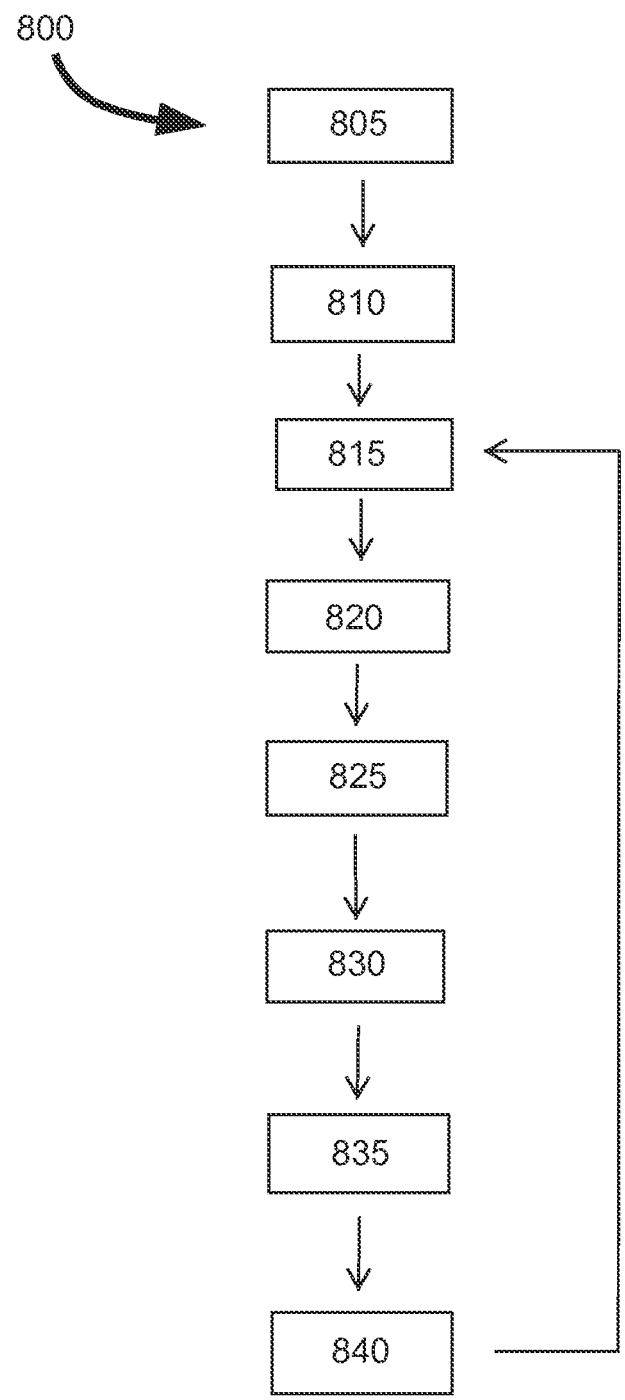

FIG. 8 depicts a flow chart of an implementation of an energy emission—sensor feedback loop 800 according to this disclosure: Step 805 may comprise: setting one or more temperatures (a desired maximal temperature threshold, or a range). In other implementations one or more such temperatures may be preset by the manufacturer. Step 810 may comprise setting one or more energy levels to lysing area and/or energy windows (a desired maximal energy threshold, or a range). In other implementations energy levels may be preset by the manufacturer. Step 815 may comprise passing the TDM through or by the target tissue area. Step 820 may comprise applying electrosurgical energy at lysing areas. Step 825 may comprise applying energy at the energy window(s). In some implementations energy may be only applied at the lysing segments. In other implementations, energy may only be applied to the energy window(s). Step 830 may comprise gathering sensor data, such as temperature data. Step 835 may comprise comparing sensor data to one or more set temperature levels. Step 840 may comprise, if the sensed temperature exceeds the threshold, reducing the amount of energy delivered through the lysing segments and/or the energy window(s).

Figure 9:
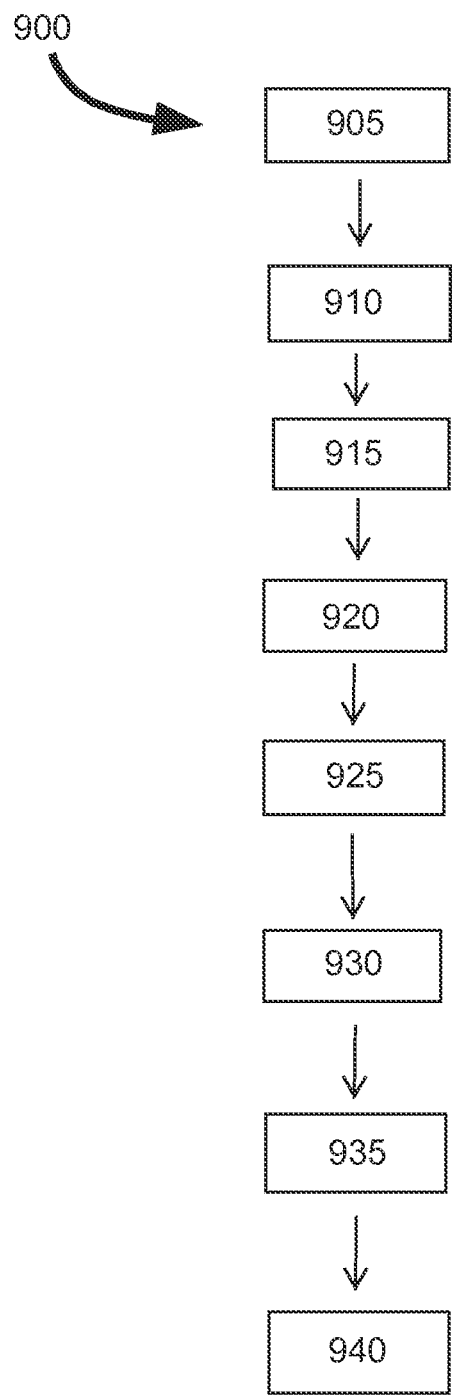
FIG. 9 is a flow chart illustrating one implementation of a method for accessing an organ using the TDM.

One implementation of a method 900 according to this disclosure for accessing an organ with the assistance of a TDM is shown in FIG. 9. In some implementations, surgeon(s) may need to access tissue and/or an organ to repair or treat it. In some implementations, the skin surrounding the anticipated entrance wound for the surgical area may be cleansed by, for example, with isopropyl alcohol (degreaser) followed by germicidal chlorhexidine scrub. Then, a local anesthetic may be applied (such as by injecting) 1% lidocaine+1:10,000 adrenaline to the skin.

Step 905 may comprise, for minimally invasive procedures or minimally invasive entrance wounds, performing a limited incision to allow passage of the maximal width of the tip or shaft of the TDM. Step 905 may be performed with, for example, a #15 Bard-Parker™ Scalpel. This incision may be deepened by scalpel, scissors or other surgical instrument to enter the desired body structure or cavity. For larger approaches, such as open abdominal surgery or trauma surgery step 905 may comprise the initial skin opening or body cavity opening steps of such a procedure. In some implementations, step 905 may comprise making the skin incision using the lysing segments of the TDM. Step 910 may comprise: applying one or more fluids to the tissues. In some implementations, step 910 may comprise applying fluids to the target tissue(s). In some implementations, step 910 may comprise applying fluids to the tissues to be traversed en route to the target tissue, in addition to, or as an alternative to applying fluids directly to the target tissue(s). In some implementations, the fluid(s) may comprise water. In some implementations, the fluid(s) may comprise an ionic fluid, such as a saline solution. The fluid(s) may be applied to the tissue via, for example, injection, or TDM fluid port or via a separate cannula or catheter or via pouring or via spray. In some implementations, the fluid(s) may comprise an ionic fluid and an anesthetic, such as a tumescent anesthesia. Non-ionic fluids may be used in other implementations; such fluids may become more ionic by diffusion of some of the patients' ions present in the surgical field. In some implementations step 910 may comprise applying one or more fluids that serve as an ionic fluid, and/or an anesthetic, and/or adrenaline. In some such implementations, the fluid(s) may comprise a Klein Formula. In some implementations, the Klein formula and amount used may be about 100 cc of Klein Formula with saline, 0.1% lidocaine, epinephrine 1:1,000,000, and $NaHCO_3$ @5 meq/L of saline).

Step 915 may comprise: passing the TDM through the various layers of tissue to create a path to a target organ. In some implementations, creating a path to a target organ or other target tissue may comprise creating a path from the incision to the target organ or other target tissue and/or creating a path around the target organ or other target tissue to allow for access to other regions of the target organ or other target tissue. In some implementations step 915 may further comprise activating the lysing segments and/or energy window to reduce bleeding or tissues traversed on the way to the target organ. In some implementations, the lysing segments and/or energy window may be used to induce fibrosis along the path, including along a path that may traverse the perimeter of the target organ/tissue. In some implementations, the TDM and/or the anticipated path may be visualized using for example an endoscope, a fiberoptic or camera, an RFID tag or other antenna. In some implementations, such a device or devices may be positioned on the TDM. In other implementations such a device or devices may be separate from the TDM. In some implementations, heat may be produced or energy may otherwise be released in the tissues through which the TDM is passed. In some implementations, heating portions of the tissues the TDM passes by may be undesirable. As such, in some implementations, undesirable heating of such layers may be mitigated by applying a cooling step antecedent and or concurrent with energy delivery with the TDM. Such steps may comprise use of one or more cooling fluids delivered via the TDM or one or more separate catheters or cannulas or endoscopes. Such cooling mechanism(s) may comprise for example, a closed water bag. Such a bag may be at a temperature of less than 37° C. In some implementations, cooling objects such as fluid or gel filled bags may be used that may range in temperature between about 1° C. to about 20° C. In some such implementations, the fluid or gel may be about 15° C. Other cooling mechanisms may comprise a dynamic cooling system wherein a cool liquid or gel is actively pumped into or through a contact cooling object. Step 920 may comprise identifying important blood vessels, nerves, ducts, organs or other anatomy in the area surrounding the target tissue. Step 925 may comprise: adding additional fluids of the types previously described to the target and/or surrounding tissues via the TDM port(s) or via one or more separate catheters or cannulas or endoscopes. Step 930 may comprise: expanding one or more regions of the path to the target tissue. In some implementations, step 930 may comprise expanding one or more path(s) from the incision to the target tissue. In some implementations, step 930 may comprise expanding a region around the target tissue such as for example, via a fanning motion. In some implementations, one or more of the other steps described herein using the TDM may also be performed with a fanning motion. In implementations using TDMs with axially oriented protrusions, such a fanning motion may comprise a to and fro spokewheel pattern. In implementations using TDMs with nonaxially oriented protrusions, such a fanning motion may comprise a side-to-side fanning motion; one example of a fanning motion using a TDM having at least one nonaxially oriented protrusion may comprise a 'windshield wiper' motion. In some implementations, step 930 may further comprise activating the energy to the TDM for example the energy to the lysing segments and/or one or more energy windows. Step 935 may comprise: observing for bleeding from larger vessels and achieving hemostasis as needed. In some implementations achieving hemostasis may be accomplished by cautery, electrifying, ligating, or chemical methods. In some implementations, the lysing segment and/or the energy window can be used to achieve the hemostasis. In some implementations, one or more other devices and/or suture and/or surgeon's hands may be used to achieve hemostasis for larger vessels. Step 940 may comprise: removing the TDM with power off and suturing the wound in the standard fashion. In some implementations, the tissues traversed may require closure by suturing and/or stapling. In some implementations, organs and/or organ systems that the TDM may be useful to access may include but not limited to muscle, and/or parotid, and/or salivary gland, and/or thyroid, and/or lung, and/or heart, and/or gastrointestinal, and/or liver, and/or pancreas, and/or spleen, and/or gallbladder, and/or kidney, and/or adrenal, and/or prostate, and/or ovary, and/or uterus, and/or bladder, and/or vascular, and/or lymph nodes and/or skeleton, and/or lung.

In some implementations, the TDM may also aid in the treatment of herniated tissues; for example, once the surgeon has stabilized and/or repositioned herniated tissue in an acceptable anatomic location and/or removed a portion and/or all of the herniated tissues, the tissues peripheral to the hernia, which may have been weak and/or allowed the herniation of the adjacent tissue to take place, may be strengthened by such things as sutures and/or postoperative fibrosis and/or a mesh implant and/or a combination of the aforementioned things. Energy from the TDM's lysing segments and/or energy windows may induce such postoperative fibrosis and may contribute to tissue strengthening in the surgically repaired area of herniation.

In some implementations, the TDM may also aid in the treatment of trauma victims; for example, gunshot and/or blast injuries and/blunt force trauma. Such patients may be in shock and bleed to a greater degree than normal due to systemic changes, some changes of which may consume and/or alter platelets and/or clotting proteins in the blood. It may be beneficial for surgeons to reach a vigorously bleeding area more rapidly while achieving a degree of hemostasis by coagulating smaller vessels along the path to reaching said vigorously bleeding area (likely due to trauma to a larger blood vessel). The TDM may have smaller vessel hemostatic capabilities when energy is applied to lysing segments and/or an energy window. Having a field of surgery with less bleeding may be beneficial to the surgeon who is working to find and repair a larger blood vessel (for example, a femoral or brachial artery). The size of the TDM's lysing areas may be such that a larger vessel will not fit into the TDM and thus not be affected by the TDM; thus, the surgeon may feel more confident that the TDM will not risk traumatizing a larger blood vessel further.

Figure 10:
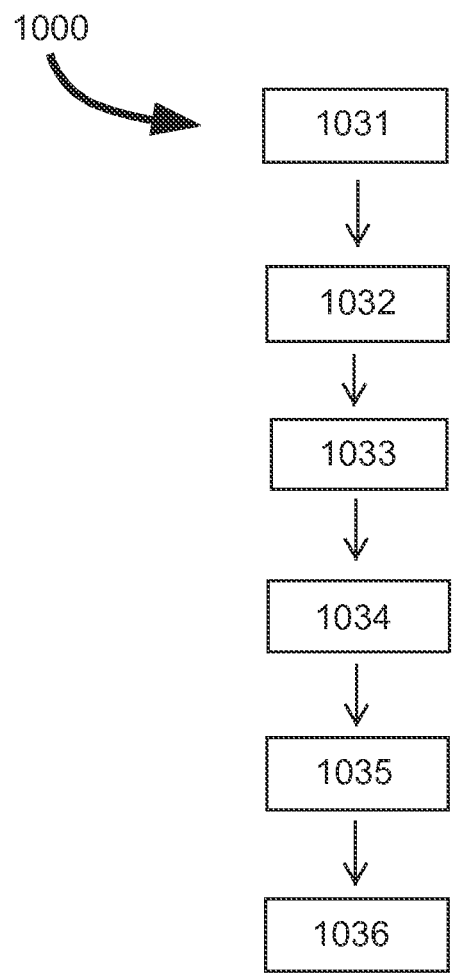
FIG. 10 is a flow chart illustrating one implementation of a method for repairing herniation using the TDM.

One implementation of a method 1000 according to this disclosure for repairing herniated tissue with the assistance of a TDM is shown in FIG. 10. Although method 1000 is shown in the figure beginning with step 1031, it should be understood that any of the preliminary steps described above in connection with other implementations may be performed in method 1000 as well. For example, one or more of steps (905-930) may be performed in method 1000 if desired. Similarly, one or more other steps of any of the other implementations described herein such as for example, steps (935-940), of the method depicted in FIG. 9 may also be included in the method depicted in FIG. 10. Step 1031 may comprise using additional instrumentation to put force upon and/or pull and/or stretch and/or make taught the herniated tissues and/or associated fibrous tissues and/or the surrounding tissue(s). In some implementations step 1031 may be performed concurrently with step 1032. Step 1031 may be performed using, for example, needles, sutures, hooks, clamps, retractors, probes, bars, endoscopes, rakes, tubes, TDM and/or by hand. Step 1032 may comprise passing the TDM to at least substantially free the herniated tissues and/or associated fibrous tissues from the surrounding tissues. In some implementations, step 1032 may further comprise applying energy to the lysing segments and/or energy windows during this TDM passage. Step 1033 may comprise heating the tissue surrounding the herniated tissue and/or associated fibrous tissues and/or tissue(s) that a surgeon intends to incorporate into the region to secure and/or restrain the herniated tissue into its intended and/or original place. Step 1034 may comprise (if further freeing appears necessary) using additional instrumentation to put force upon and/or pull and/or stretch and/or make taught target tissue(s) while the TDM may be passed to more uniformly apply energy to the target tissue via the lysing segments and/or energy windows (in order to attempt hemostasis and/or induce postoperative fibrosis). Step 1035 may comprise sewing, stapling or binding the support tissues and/or herniated tissues into place. Step 1036 may comprise passing the TDM adjacent to those tissues that have been sewn and/or otherwise bound. In some implementations, step 1036 may comprise activation of the lysing segments and/or energy window to induce supportive fibrosis. In some implementations, organs and/or organ systems that the TDM may be useful to assist in remedying a herniated state may include but not limited to muscle, and/or parotid, and/or salivary gland, and/or gastrointestinal, and/or uterus, and/or bladder, and/or vascular, and/or genitourinary.

Figure 11:
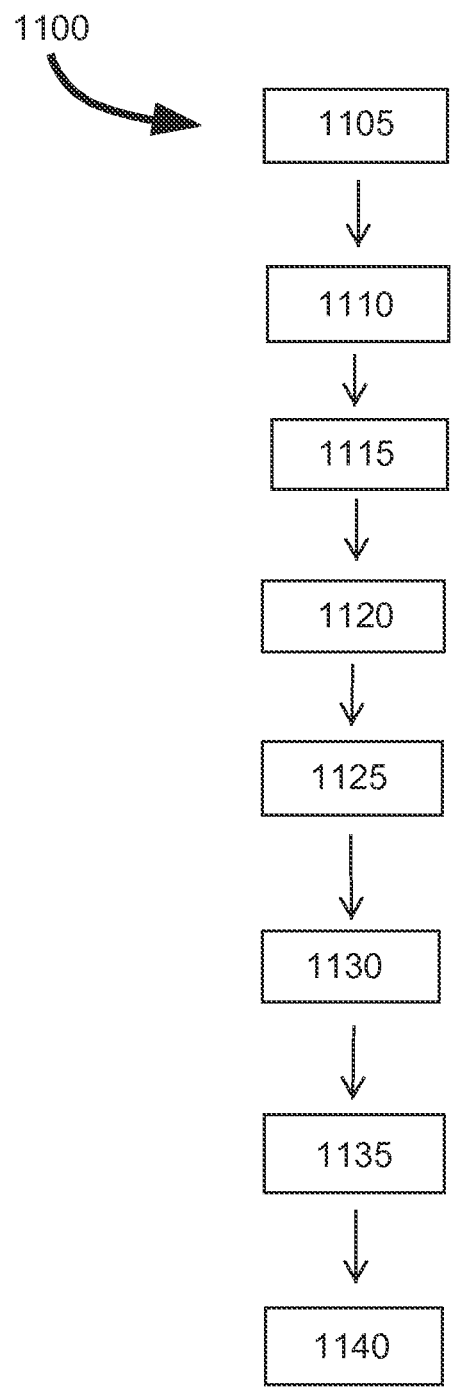
FIG. 11 is a flow chart illustrating one implementation of a method for accessing the central nervous system using the TDM.

One implementation of a method 1100 according to this disclosure for accessing the central nervous system (CNS) with the assistance of a TDM is shown in FIG. 11. In some implementations, the skin surrounding the anticipated entrance wound for the surgical area may be cleansed by, for example, with isopropyl alcohol (degreaser) followed by germicidal chlorhexidine scrub. Then, a local anesthetic may be applied (such as by injecting) 1% lidocaine+1:10,000 adrenaline to the skin.

Step 1105 may comprise, making an entrance wound in, for example the scalp via a #15 Bard-Parker™ Scalpel. This incision may be deepened by scalpel, scissors or other surgical instrument to enter subgaleal layer. Step 1110 may comprise: applying one or more fluids to subgaleal tissues. In some implementations, the fluid(s) may comprise water. In some implementations, the fluid(s) may comprise an ionic fluid, such as a saline solution. The fluid(s) may be applied to the tissue via, for example, injection, or TDM fluid port or via a separate cannula or catheter or via pouring or via spray. In some implementations, the fluid(s) may comprise an ionic fluid and an anesthetic, such as a tumescent anesthesia. Non-ionic fluids may be used in other implementations; such fluids may become more ionic by diffusion of some of the patients' ions present in the surgical field. In some implementations step 1110 may comprise applying one or more fluids that serve as an ionic fluid, and/or an anesthetic, and/or adrenaline. In some such implementations, the fluid(s) may comprise a Klein Formula. In some implementations, the Klein formula and amount used may be about 100 cc of Klein Formula with saline, 0.1% lidocaine, epinephrine 1:1,000, 000, and NaHCO3@5 meq/L of saline). Step 1115 may comprise: moving the TDM through the subgaleal layer; this may allow the scalp to be retracted for better access to open the skull via bone saw and/or other tools known in the art. In some implementations, such movement may comprise a fanning motion. In some implementations step 1115 may further comprise activating the lysing segments and/or energy window to reduce bleeding from emissary blood vessels. Step 1120 may comprise dissecting the dura using the TDM and/or identifying important blood vessels, and/or other anatomy in the area surrounding the target tissue. Step 1125 may comprise: adding additional fluids of the types previously described to the target and/or surrounding tissues via the TDM port(s) or via one or more separate catheters or cannulas or endoscopes prior to and/or during the application of energy by TDM. Step 1130 may comprise: activating the energy to the TDM for example the energy to the lysing segments and/or one or more energy windows. Step 1130 may further comprise passing the TDM through and around the target tissue in the CNS such as for example, via a delicate fanning motion. In some implementations, the TDM and/or the anticipated path may be visualized using for example an endoscope, a fiberoptic or camera, an RFID tag or other antenna. In some implementations, such a device or devices may be positioned on the TDM. In other implementations such a device or devices may be separate from the TDM. In some implementations, heat may be produced or energy may otherwise be released in the tissues through which the TDM is passed. In some implementations, heating portions of the tissues the TDM passes by may be undesirable. As such, in some implementations, undesirable heating of such layers may be mitigated by applying a cooling step antecedent and or concurrent with energy delivery with the TDM. Such steps may comprise use of one or more cooling fluids delivered via the TDM or one or more separate catheters or cannulas or endoscopes. Step 1135 may comprise: observing for bleeding from larger vessels and achieving hemostasis as needed. In some implementations achieving hemostasis may be accomplished by cautery, electrifying, ligating, or chemical methods. In some implementations, the lysing segment and/or the energy window can be used to achieve the hemostasis. In some implementations, one or more other devices and/or suture and/or surgeon's hands may be used to achieve hemostasis for larger vessels. Step 1140 may comprise: removing the TDM with power off and suturing the wound in the standard fashion.

Figure 12:
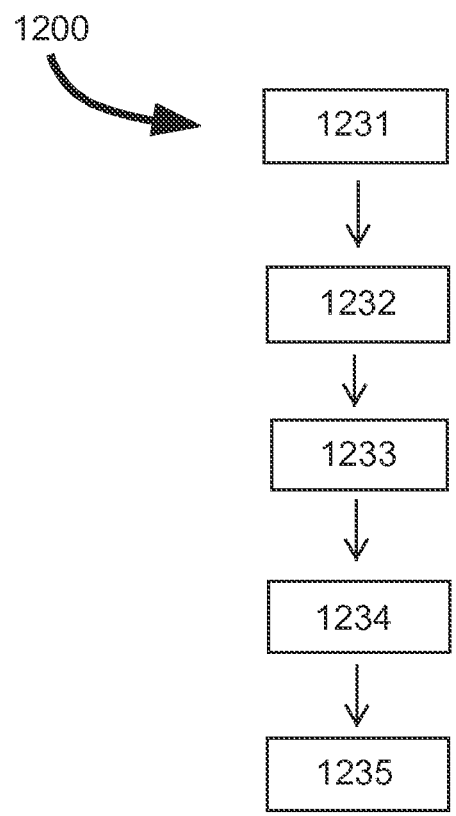
FIG. 12 is a flow chart illustrating one implementation of a method for removing tissue from a peripheral nerve such as for example tumor and/or scar tissue and/or fibrosis with the assistance of a TDM.

One implementation of a method 1200 according to this disclosure for removing tissue from a peripheral nerve such as for example tumor and/or scar tissue and/or fibrosis with the assistance of a TDM is shown in FIG. 12. Although method 1200 is shown in the figure beginning with step 1231, it should be understood that any of the preliminary steps described above in connection with other implementations may be performed in method 1200 as well. For example, one or more of steps (905-930) may be performed in method 1200 if desired. Similarly, one or more other steps of any of the other implementations described herein such as for example, steps (935-940), of the method depicted in FIG. 9 may also be included in the method depicted in FIG. 12. Step 1231 may comprise using additional instrumentation to put force upon and/or pull and/or stretch and/or make taught the nerve and/or tissue adjacent a peripheral nerve (such as for example tumor and/or scar tissue and/or fibrosis) and/or surrounding tissue(s). Step 1231 may be performed using, for example, needles, sutures, hooks, clamps, retractors, probes, bars, endoscopes, rakes, tubes, TDM and/or by hand. In some implementations step 1231 may be performed concurrently with step 1232. Step 1232 may comprise passing the TDM to at least substantially free the tumor(s) and/or scar tissue and/or fibrosis from the nerve and/or surrounding tissues. In some implementations, step 1232 may further comprise applying energy to the lysing segments and/or energy windows during this TDM passage. Step 1233 may comprise identifying and/or testing the tissue (such as for example tumor and/or scar tissue and/or fibrosis) to determine if it has been sufficiently freed from the nerve and/or surrounding tissues for uncomplicated removal. In some implementations endoscopes and/or blunt probes and/or TDM and/or surgeon's hands may be passed around the tumor and/or scar tissue and/or fibrosis to test the degree of freedom the tumor and/or scar tissue and/or fibrosis has from the nerve and/or surrounding tissues. Step 1234 may comprise (if further freeing appears necessary) using additional instrumentation to put force upon and/or pull and/or stretch and/or make taught the nerve and/or tumor and/or scar tissue and/or fibrosis. Step 1235 may comprise passing the TDM to further free the nerve; energy may be applied to the lysing segments and/or energy windows during this TDM passage (in order to attempt hemostasis and/or induce postoperative fibrosis). Step 1235 may be repeated as necessary until the tumor and/or scar tissue and/or fibrosis is sufficiently freed for removal. In an implementation the TDM is passed longitudinally along the nerve in a 'stripping' fashion, such that a longitudinal axis of the TDM is at least substantially parallel to a longitudinal axis of the nerve during step 1233.

Figure 13:
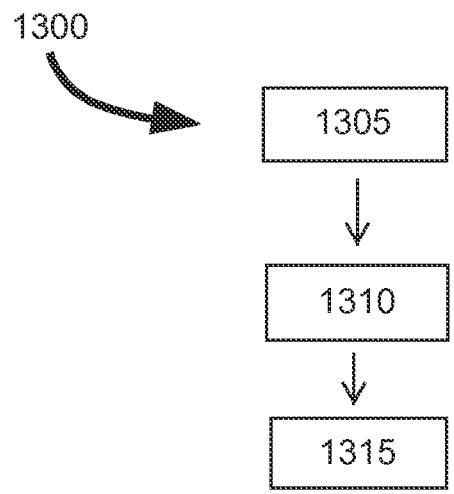
FIG. 13 is a flow chart of an implementation of a method for separating and/or modifying tissue using a TDM.

FIG. 13 depicts a flow chart of an implementation of a method for separating and/or modifying tissue using a TDM. In this particular implementation, the use of combined data from the tissue dissecting and modifying wand generated from at least the temperature sensor and the antenna(s) may be used to provide suitable feedback to a user during treatment. In some implementations, the TDM Wand may comprise a tip comprising a plurality of protrusions. One or more lysing segments may be positioned between at least two adjacent protrusions among the plurality of protrusions. A temperature sensor may be positioned on the TDM. The temperature sensor may be configured to sense a temperature of at least one of tissue and fluid adjacent to the tissue dissecting and modifying wand during an operation. The fluid of which a temperature reading is taken may comprise, for example, fluid from adjacent tissue(s) and/or fluid introduced during the procedure by way of the TDM and/or another device or procedure. The TDM may also comprise an antenna(s) such as an RFID tag positioned on the TDM. In some implementations, the antenna(s) may be positioned on the tip and/or distal end of the shaft, such as on a bottom surface of the tip and/or distal end of the shaft. The antenna(s) may be configured to provide location data regarding a location of the TDM, such as a particular portion or region of the TDM for example, during an operation or procedure. Although method 1300 is shown in the figure beginning with step 1305, it should be understood that any of the preliminary steps described above in connection with other implementations may be performed in method 1300 as well. For example, one or more of steps (905-930) from method 900 may be performed in method 1300 if desired. Similarly, one or more other steps of any of the other implementations described herein may also be included in the method depicted in FIG. 13. In some implementations, step 1305 may comprise: receiving data from the tissue dissecting and modifying wand temperature sensor. Step 1310 may comprise receiving data from the antenna(s) such as RFID tag data. Step 1315 may comprise combining the data generated from at least the temperature sensor and the antenna(s). In some implementations, the data from the temperature sensor and the antenna(s) may be combined before it is received. In other words, a step of "receiving combined data from the tissue dissecting and modifying wand generated from at least the temperature sensor and the antenna(s)" may comprise receiving precombined data (data from the temperature sensor and the antenna(s) that was combined before it was received) or, alternatively, may comprise separately receiving temperature data and antenna(s) data that may be combined to allow for one or more particular features or functionalities. The combined data may be used to allow a surgeon or other user to determine one or more regions within a patient's body that have been adequately treated using the TDM wand. For example, in some implementations, the combined data may allow a user to visualize one or more regions within a patient's body, such as one or more regions that have been sufficiently treated. This may be accomplished, for example, by creating an image corresponding with one or more regions of a patient's body. Such image or images may be highlighted, receive color changes, or otherwise modified on a display to indicate to the user which regions have been adequately treated. In some implementations, such regions may correspond with regions comprising tissue that has reached a predetermined threshold temperature.

In a more general implementation of a method according to this disclosure for dissection and modification of tissues, a first step may comprise creating an incision into a patient's skin.

A second step may comprise inserting a Tissue Dissecting and Modifying Wand into the incision and positioning the Tissue Dissecting and Modifying Wand within the body. The Tissue Dissecting and Modifying Wand may comprise a tip having a plurality of protrusions with lysing segments positioned between the protrusions. The Tissue Dissecting and Modifying Wand may also comprise an energy window positioned on top of the Tissue Dissecting and Modifying Wand that is configured to deliver energy to modify tissues.

A third step may comprise fanning out the Tissue Dissecting and Modifying Wand to define a target region within which to dissect and modify tissues. This step may comprise separating tissue using the lysing segment(s) to define the target region. During this step, in some implementations, the patient's target tissue may be placed under tension by stretching/tightening the target tissue at the target region during the fanning/tissue separation.

A fourth step may comprise activating the energy window and moving the energy window around within the target region for hemostasis and/or to induce postoperative fibrosis. Alternatively, the energy window may be activated prior to the third step such that the step of fanning out the Tissue Dissecting and Modifying Wand to define the target region also comprises heating tissues to induce fibrosis and/or hemostasis within the target region.

In another embodiment of a method for separating and modifying tissue using a tissue dissecting and modifying wand, the method may comprise creating an incision into a patient's skin. A tissue dissecting and modifying wand may be inserted into the incision. The tissue dissecting and modifying wand may comprise a tip comprising a plurality of protrusions; at least one lysing segment positioned between at least two adjacent protrusions among the plurality of protrusions; and an energy window configured to deliver energy to tissue adjacent to the tissue dissecting and modifying wand during a procedure. The energy window may comprise an ultrasonic energy emitter, wherein the ultrasonic energy emitter is configured to use electrical energy and emit ultrasonic energy from the energy window, and wherein the energy window is positioned and configured to deliver the ultrasonic energy from the tissue dissecting and modifying wand to tissue adjacent to the tissue dissecting and modifying wand during a procedure.

The tissue dissecting and modifying wand may further comprise a radiofrequency identification tag positioned on the tissue dissecting and modifying wand and configured to provide location data regarding a location of the tissue dissecting and modifying wand during a procedure. In such implementations, data may be received from the tissue dissecting and modifying wand generated from the radiofrequency identification tag, wherein the data allows a user to determine one or more regions within a patient's body that have been treated using energy from the ultrasonic energy window.

In alternative implementations, the energy window may comprise an impedance-matched microwave emission system. In such implementations, date may be received from the tissue dissecting and modifying wand generated from the radiofrequency identification tag, wherein the data allows a user to determine one or more regions within a patient's body that have been treated using energy from the energy window.

In another implementation of a method for separating and modifying tissue using a tissue dissecting and modifying wand, the tissue dissecting and modifying wand may comprise a tip comprising a first plurality of protrusions and a second plurality of protrusions, wherein the first plurality of protrusions is positioned to at least substantially extend in a first direction, and wherein the second plurality of protrusions is positioned to at least substantially extend in a second direction distinct from the first direction; at least one lysing segment positioned between at least two adjacent protrusions in the first plurality of protrusions; at least one lysing segment positioned between at least two adjacent protrusions in the second plurality of protrusions; and a radiofrequency identification tag positioned on the tissue dissecting and modifying wand and configured to provide location data regarding a location of the tissue dissecting and modifying wand during a procedure. In such implementations, the method may comprise a step of receiving data from the tissue dissecting and modifying wand generated from the radiofrequency identification tag, wherein the data allows a user to locate the tissue dissecting and modifying wand during a procedure. In this manner, the RFID tag data may allow a user to, for example, visualize a current location of the TDM, view information sufficient to guide a user toward a target area within a patient, and/or view information sufficient to determine one or more locations within a patient that have been sufficiently treated using the TDM (such as the energy window, for example).

An example of an embodiment of an apparatus according to this disclosure for tissue dissection and modification may comprise:
 a handle;
 a tip comprising a plurality of protrusions having one or more lysing segments positioned between the protrusions; and
 an energy window positioned on an upper side of the apparatus, wherein the energy window comprises a ultrasonic energy emitter, and wherein the ultrasonic energy emitter is configured to absorb electrical energy and emit ultrasonic energy from the energy window.

In some embodiments as described above, the energy window may comprise a electrical elements that are configured to deliver electrical energy to the ultrasonic energy emitter such that the ultrasonic energy emitter can then emit ultrasonic energy from the energy window.

An example of an embodiment of an apparatus according to this disclosure for tissue dissection and modification may comprise:
 a handle;
 a tip comprising a plurality of protrusions having one or more lysing segments positioned between the protrusions; and
 an energy window positioned on an upper side of the apparatus, wherein the energy window comprises an ultrasonic energy emitter, and wherein the ultrasonic energy emitter is configured to use electrical energy and emit ultrasonic energy from the energy window.

In some embodiments as described above, the energy window may comprise a electrical elements that are configured to deliver energy to the ultrasound media such that the ultrasonic energy emitter can then emit ultrasonic energy from the energy window.

Another example of an embodiment of an apparatus according to this disclosure for tissue dissection and modification may comprise:
 a handle;
 a tip comprising a plurality of protrusions having one or more lysing segments positioned between the protrusions; and
 an energy window positioned on an upper side of the apparatus, wherein the energy window comprises an target-tissue-impedance-matched-microwave-based energy window.

Another example of an embodiment of an apparatus according to this disclosure for tissue dissection and modification may comprise:
 a handle;
 a tip comprising a plurality of protrusions having one or more lysing segments positioned between the protrusions; and
 an energy window positioned on an upper side of the apparatus, wherein the energy window comprises a LASER based energy window.

Another example of an embodiment of an apparatus according to this disclosure for tissue dissection and modification may comprise:
 a handle;
 a tip comprising a plurality of protrusions having one or more lysing segments positioned between the protrusions; and
 an energy window positioned on an upper side of the apparatus, wherein the energy window comprises an intense pulsed light based energy window.

Another example of an embodiment of an apparatus according to this disclosure for tissue dissection and modification may comprise:
 a handle;
 a tip comprising a plurality of protrusions having one or more lysing segments positioned between the protrusions; and
 an energy window positioned on an upper side of the apparatus, wherein the energy window comprises a microwave based energy window.

Another example of an embodiment of an apparatus according to this disclosure for tissue dissection and modification may comprise:
 a handle;
 a tip comprising a plurality of protrusions having one or more lysing segments positioned between the protrusions; and an energy window positioned on an upper side of the apparatus, wherein the energy window comprises an ultrasound based energy window.

Another example of an embodiment of an apparatus according to this disclosure for tissue dissection and modification may comprise:
　a handle;
　a tip comprising a plurality of protrusions having one or more lysing segments positioned between the protrusions; and
　an energy window positioned on an upper side of the apparatus, wherein the energy window comprises an electrosurgical based energy window.

Another example of an embodiment of an apparatus according to this disclosure for tissue dissection and modification may comprise:
　a handle;
　a tip comprising a plurality of protrusions having one or more lysing segments positioned between the protrusions; and
　an energy window positioned on an upper side of the apparatus, wherein the energy window comprises a light from filament based energy window.

Another example of an embodiment of an apparatus according to this disclosure for tissue dissection and modification may comprise:
　a handle;
　a tip comprising a plurality of protrusions having one or more lysing segments positioned between the protrusions; and
　an energy window positioned on an upper side of the apparatus, wherein the energy window comprises a thermal based energy window.

It will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

Furthermore, the described features, components, structures, steps, or characteristics may be combined in any suitable manner in one or more alternative embodiments and/or implementations. In other words, any of the features, components, structures, steps, or characteristics disclosed in any one disclosed embodiment may be combined with features, components, structures, steps, or characteristics of other disclosed embodiments.

The invention claimed is:

1. A method for removing fibrous tissue in a patient using a tissue dissecting and modifying wand, the method comprising the steps of:
　creating an incision into a patient's skin;
　inserting a tissue dissecting and modifying wand into the incision, wherein the tissue dissecting and modifying wand comprises:
　　a shaft;
　　a tip positioned at a distal end of the shaft, wherein the tip comprises a plurality of protrusions; and
　　at least one lysing segment positioned between at least two adjacent protrusions among the plurality of protrusions;
　passing the tissue dissecting and modifying wand through tissue to create a path to a target fibrous tissue;
　positioning the tissue dissecting and modifying wand adjacent to the target fibrous tissue within the patient; and
　removing the target fibrous tissue using the tissue dissecting and modifying wand.

2. The method of claim 1, wherein the step of passing the tissue dissecting and modifying wand through tissue to create a path to a target fibrous tissue comprises passing the tissue dissecting and modifying wand through tissue in a fanning motion to create least a portion of the path the path to the target fibrous tissue.

3. The method of claim 1, wherein the step of passing the tissue dissecting and modifying wand through tissue to create a path to a target fibrous tissue comprises activating the at least one lysing segment to apply energy to the tissue defining the path.

4. The method of claim 3, wherein the step of passing the tissue dissecting and modifying wand through tissue to create a path to a target fibrous tissue comprises activating the at least one lysing segment to apply electrical energy to the tissue defining the path.

5. The method of claim 1, wherein the tissue dissecting and modifying wand further comprises an energy window, wherein the energy window is configured to deliver energy to tissue adjacent to the energy window during operations with the tissue dissecting and modifying wand.

6. The method of claim 5, wherein the step of passing the tissue dissecting and modifying wand through tissue to create a path to a target fibrous tissue comprises activating the energy window to at least one of reduce bleeding within the path and induce fibrosis within tissues defining the path.

7. The method of claim 1, wherein the tissue dissecting and modifying wand further comprises:
　a second plurality of protrusions positioned along the tip; and
　at least one lysing segment positioned between at least two adjacent protrusions in the second plurality of protrusions, wherein the plurality of protrusions is positioned to at least substantially extend in a first direction, and wherein the second plurality of protrusions is positioned to at least substantially extend in a second direction distinct from the first direction.

8. The method of claim 7, wherein the first direction is at least substantially perpendicular to the second direction.

9. The method of claim 7, wherein the first direction extends at an acute angle relative to the second direction.

10. The method of claim 7, further comprising a third plurality of protrusions positioned on the tip, wherein the third plurality of protrusions is positioned to at least substantially extend in a third direction distinct from the first and second directions.

11. The method of claim 10, wherein the first direction extends at least substantially along a longitudinal axis of the tissue dissecting and modifying wand, wherein the second direction is at least substantially perpendicular to the first direction, and wherein the third direction extends at an acute angle relative to both the first and second directions.

12. The method of claim 1, wherein the step of removing the target fibrous tissue from an organ using the tissue dissecting and modifying wand comprises removing the target fibrous tissue from at least one of a muscle, lung, heart, gastrointestinal, and gallbladder tissue.

13. The method of claim 1, wherein the step of passing the tissue dissecting and modifying wand through tissue to create a path to a target fibrous tissue comprises applying at least one fluid to the tissue defining the path while creating the path.

14. A method for repairing herniated tissue in a patient using a tissue dissecting and modifying wand, the method comprising the steps of:
creating an incision into a patient's skin;
inserting a tissue dissecting and modifying wand into the incision, wherein the tissue dissecting and modifying wand comprises:
a shaft;
a tip positioned at a distal end of the shaft, wherein the tip comprises a plurality of protrusions; and
at least one lysing segment positioned between at least two adjacent protrusions among the plurality of protrusions;
passing the tissue dissecting and modifying wand through tissue to create a path to a target herniated tissue;
positioning the tissue dissecting and modifying wand adjacent to the target herniated tissue within the patient; and
removing the target herniated tissue using the tissue dissecting and modifying wand.

15. The method of claim 14, wherein the step of passing the tissue dissecting and modifying wand through tissue to create a path to a target herniated tissue comprises passing the tissue dissecting and modifying wand through tissue in a fanning motion to create least a portion of the path the path to the target herniated tissue.

16. The method of claim 14, wherein the step of passing the tissue dissecting and modifying wand through tissue to create a path to a target herniated tissue comprises activating the at least one lysing segment to apply energy to the tissue defining the path.

17. The method of claim 16, wherein the step of passing the tissue dissecting and modifying wand through tissue to create a path to a target herniated tissue comprises activating the at least one lysing segment to apply electrical energy to the tissue defining the path.

18. The method of claim 14, wherein the tissue dissecting and modifying wand further comprises an energy window, wherein the energy window is configured to deliver energy to tissue adjacent to the energy window during operations with the tissue dissecting and modifying wand.

19. The method of claim 18, wherein the step of passing the tissue dissecting and modifying wand through tissue to create a path to a target herniated tissue comprises activating the energy window to at least one of reduce bleeding within the path and induce fibrosis within tissues defining the path.

20. The method of claim 14, wherein the tissue dissecting and modifying wand further comprises:
a second plurality of protrusions positioned along the tip; and
at least one lysing segment positioned between at least two adjacent protrusions in the second plurality of protrusions, wherein the plurality of protrusions is positioned to at least substantially extend in a first direction, and wherein the second plurality of protrusions is positioned to at least substantially extend in a second direction distinct from the first direction.

21. The method of claim 20, wherein the first direction is at least substantially perpendicular to the second direction.

22. The method of claim 20, wherein the first direction extends at an acute angle relative to the second direction.

23. The method of claim 20, further comprising a third plurality of protrusions positioned on the tip, wherein the third plurality of protrusions is positioned to at least substantially extend in a third direction distinct from the first and second directions.

24. The method of claim 23, wherein the first direction extends at least substantially along a longitudinal axis of the tissue dissecting and modifying wand, wherein the second direction is at least substantially perpendicular to the first direction, and wherein the third direction extends at an acute angle relative to both the first and second directions.

25. The method of claim 14, wherein the step of repairing herniated tissue using the tissue dissecting and modifying wand comprises repairing herniated tissue from at least one of a muscle, gastrointestinal, and genitourinary tissue.

26. The method of claim 14, wherein the step of passing the tissue dissecting and modifying wand through tissue to create a path to a target herniated tissue comprises applying at least one fluid to the tissue defining the path while creating the path.

27. The method of claim 14, wherein the step of repairing herniated tissue using the tissue dissecting and modifying wand comprises separating at least one of herniated and tissues adjacent to the herniated tissue.

28. The method of claim 14, wherein the step of repairing herniated tissue using the tissue dissecting and modifying wand comprises inducing fibrosis to at least one of herniated and tissues adjacent to the herniated tissue.

29. A method for accessing a portion of the Central Nervous System in a patient using a tissue dissecting and modifying wand, the method comprising the steps of:
creating an incision into a patient's skin;
inserting a tissue dissecting and modifying wand into the incision, wherein the tissue dissecting and modifying wand comprises:
a shaft;
a tip positioned at a distal end of the shaft, wherein the tip comprises a plurality of protrusions; and
at least one lysing segment positioned between at least two adjacent protrusions among the plurality of protrusions;
passing the tissue dissecting and modifying wand through tissue to create a path to a target portion of the Central Nervous System; and
positioning the tissue dissecting and modifying wand adjacent to the target portion of the Central Nervous System within the patient.

30. The method of claim 29, wherein the step of passing the tissue dissecting and modifying wand through tissue to create a path to a target portion of the Central Nervous System comprises passing the tissue dissecting and modifying wand through tissue in a fanning motion to create at least a portion of the path to the target portion of the Central Nervous System.

31. The method of claim 29, wherein the step of passing the tissue dissecting and modifying wand through tissue to create a path to a target portion of the Central Nervous System comprises activating the at least one lysing segment to apply energy to the tissue defining the path.

32. The method of claim 31, wherein the step of passing the tissue dissecting and modifying wand through tissue to create a path to a target portion of the Central Nervous System comprises activating the at least one lysing segment to apply electrical energy to the tissue defining the path.

33. The method of claim 29, wherein the tissue dissecting and modifying wand further comprises an energy window, wherein the energy window is configured to deliver energy to tissue adjacent to the energy window during operations with the tissue dissecting and modifying wand.

34. The method of claim 33, wherein the step of passing the tissue dissecting and modifying wand through tissue to create a path to a target portion of the Central Nervous System comprises activating the energy window to reduce bleeding within the path.

35. The method of claim 29, wherein the tissue dissecting and modifying wand further comprises:
a second plurality of protrusions positioned along the tip; and
at least one lysing segment positioned between at least two adjacent protrusions in the second plurality of protrusions, wherein the plurality of protrusions is positioned to at least substantially extend in a first direction, and wherein the second plurality of protrusions is positioned to at least substantially extend in a second direction distinct from the first direction.

36. The method of claim 35, wherein the first direction is at least substantially perpendicular to the second direction.

37. The method of claim 35, wherein the first direction extends at an acute angle relative to the second direction.

38. The method of claim 35, further comprising a third plurality of protrusions positioned on the tip, wherein the third plurality of protrusions is positioned to at least substantially extend in a third direction distinct from the first and second directions.

39. The method of claim 38, wherein the first direction extends at least substantially along a longitudinal axis of the tissue dissecting and modifying wand, wherein the second direction is at least substantially perpendicular to the first direction, and wherein the third direction extends at an acute angle relative to both the first and second directions.

40. The method of claim 29, wherein the target portion of the Central Nervous System comprises a portion of the patient's brain.

41. The method of claim 29, wherein the step of passing the tissue dissecting and modifying wand through tissue to create a path to a target portion of the Central Nervous System comprises applying at least one fluid to the tissue defining the path while creating the path.

42. A method for removing tissue from a nerve in a patient using a tissue dissecting and modifying wand, the method comprising the steps of:
creating an incision into a patient's skin;
inserting a tissue dissecting and modifying wand into the incision, wherein the tissue dissecting and modifying wand comprises:
a shaft;
a tip positioned at a distal end of the shaft, wherein the tip comprises a plurality of protrusions; and
at least one lysing segment positioned between at least two adjacent protrusions among the plurality of protrusions;
passing the tissue dissecting and modifying wand through tissue to create a path to a target tissue from a nerve;
positioning the tissue dissecting and modifying wand adjacent to the target tissue from a nerve within the patient; and
removing the target tissue from a nerve using the tissue dissecting and modifying wand.

43. The method of claim 42, wherein the step of passing the tissue dissecting and modifying wand through tissue to create a path to a target tissue from a nerve comprises passing the tissue dissecting and modifying wand through tissue in a fanning motion to create least a portion of the path the path to the target tissue from a nerve.

44. The method of claim 42, wherein the step of passing the tissue dissecting and modifying wand through tissue to create a path to a target tissue from a nerve comprises activating the at least one lysing segment to apply energy to the tissue defining the path.

45. The method of claim 44, wherein the step of passing the tissue dissecting and modifying wand through tissue to create a path to a target tissue from a nerve comprises activating the at least one lysing segment to apply electrical energy to the tissue defining the path.

46. The method of claim 42, wherein the tissue dissecting and modifying wand further comprises an energy window, wherein the energy window is configured to deliver energy to tissue adjacent to the energy window during operations with the tissue dissecting and modifying wand.

47. The method of claim 46, wherein the step of passing the tissue dissecting and modifying wand through tissue to create a path to a target tissue from a nerve comprises activating the energy window to at least one of reduce bleeding within the path and induce fibrosis within tissues defining the path.

48. The method of claim 42, wherein the tissue dissecting and modifying wand further comprises:
a second plurality of protrusions positioned along the tip; and
at least one lysing segment positioned between at least two adjacent protrusions in the second plurality of protrusions, wherein the plurality of protrusions is positioned to at least substantially extend in a first direction, and wherein the second plurality of protrusions is positioned to at least substantially extend in a second direction distinct from the first direction.

49. The method of claim 48, wherein the first direction is at least substantially perpendicular to the second direction.

50. The method of claim 48, wherein the first direction extends at an acute angle relative to the second direction.

51. The method of claim 48, further comprising a third plurality of protrusions positioned on the tip, wherein the third plurality of protrusions is positioned to at least substantially extend in a third direction distinct from the first and second directions.

52. The method of claim 51, wherein the first direction extends at least substantially along a longitudinal axis of the tissue dissecting and modifying wand, wherein the second direction is at least substantially perpendicular to the first direction, and wherein the third direction extends at an acute angle relative to both the first and second directions.

53. The method of claim 42, wherein the step of passing the tissue dissecting and modifying wand through tissue to create a path to a target tissue from a nerve comprises applying at least one fluid to the tissue defining the path while creating the path.

* * * * *